United States Patent
Albelda et al.

(10) Patent No.: US 12,116,418 B2
(45) Date of Patent: *Oct. 15, 2024

(54) DISRUPTING TUMOR TISSUES BY TARGETING FIBROBLAST ACTIVATION PROTEIN (FAP)

(71) Applicant: The Trustees of the University of Pennsylvania, Philadelphia, PA (US)

(72) Inventors: Steven A. Albelda, Philadelphia, PA (US); Ellen Puré, Bryn Mawr, PA (US); Leslie Todd, Conshohocken, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 481 days.

This patent is subject to a terminal disclaimer.

(21) Appl. No.: 17/029,702

(22) Filed: Sep. 23, 2020

(65) Prior Publication Data

US 2021/0087295 A1 Mar. 25, 2021

Related U.S. Application Data

(60) Provisional application No. 62/904,340, filed on Sep. 23, 2019.

(51) Int. Cl.
| | | |
|---|---|---|
| *C12N 15/13* | (2006.01) |
| *A61K 35/17* | (2015.01) |
| *A61K 45/06* | (2006.01) |
| *A61P 35/00* | (2006.01) |
| *C07K 14/705* | (2006.01) |
| *C07K 14/725* | (2006.01) |
| *C07K 16/40* | (2006.01) |
| *C12N 5/0783* | (2010.01) |

(52) U.S. Cl.
CPC ............ *C07K 16/40* (2013.01); *A61K 35/17* (2013.01); *A61K 45/06* (2013.01); *A61P 35/00* (2018.01); *C07K 14/7051* (2013.01); *C07K 14/70521* (2013.01); *C07K 14/70578* (2013.01); *C12N 5/0638* (2013.01); *C07K 2317/33* (2013.01); *C07K 2317/53* (2013.01); *C07K 2317/565* (2013.01); *C07K 2317/622* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 9,365,641 B2 | 6/2016 | June |
| 11,447,570 B2 | 9/2022 | June |
| 2004/0137513 A1 | 7/2004 | Devaux |
| 2007/0135998 A1 | 6/2007 | Van Vlijmen |
| 2011/0052606 A1 | 3/2011 | Spee |
| 2014/0099340 A1 | 4/2014 | June |
| 2016/0060356 A1 | 3/2016 | Bacac |
| 2016/0176964 A1 | 6/2016 | Arathoon |
| 2016/0194402 A1 | 7/2016 | Van Eenennaam |
| 2016/0326265 A1 | 11/2016 | June |
| 2017/0081411 A1 | 3/2017 | Engels |
| 2017/0226225 A1 | 8/2017 | Chen |
| 2018/0022822 A1* | 1/2018 | Brokopp ............... A61P 43/00 |
| | | | 435/328 |
| 2019/0167721 A1 | 6/2019 | Fan |
| 2019/0202902 A1 | 7/2019 | Chen |

FOREIGN PATENT DOCUMENTS

| | | |
|---|---|---|
| WO | 2000029584 | 5/2000 |
| WO | 2005011376 | 2/2005 |
| WO | 2011040972 A1 | 4/2011 |
| WO | 2013117761 | 8/2013 |
| WO | 2014055442 A2 | 4/2014 |
| WO | 2014184194 | 11/2014 |
| WO | 2015032906 | 3/2015 |
| WO | 2015090229 A1 | 6/2015 |
| WO | 2016070050 | 5/2016 |
| WO | 2017181119 | 10/2017 |
| WO | 2018105560 | 6/2018 |
| WO | 2018148440 A1 | 8/2018 |
| WO | 2019067425 | 4/2019 |
| WO | 2019126724 | 6/2019 |
| WO | 2019173291 | 9/2019 |
| WO | 2021061708 | 4/2021 |
| WO | 2021061778 | 4/2021 |
| WO | 2022081694 | 4/2022 |

OTHER PUBLICATIONS

Tillmanns, J. et al., "Fibroblast activation protein alpha expression identifies activated fibroblasts after myocardial infarction," J Mol Cell Cardiol, 87:194-203 (2015).
Wang, Liang-Chuan et al., "Targeting Fibroblast Activation Protein in Tumor Stroma with Chimeric Antigen Receptor T Cells Can Inhibit Tumor Growth and Augment Host Immunity Without Severe Toxicity<" Cancer Immunol Res 2 (2):154-166 (Feb. 2014).
Lo, A. et al., "Tumor-Promoting Desmoplasia Is Disrupted by Depleting FAP-Expressing Stromal Cells," Cancer Res, 75(14): 2800-2810 (2015).
Aghajanian, H. et al., "Targeting cardiac fibrosis with engineered T cells," Nature, 573:430-433 (Sep. 19, 2019).
International Search Report for PCT/US20/52227 (Jan. 27, 2021).
International Search Report for PCT/US20/52121 (Feb. 10, 2021).

(Continued)

*Primary Examiner* — Michael D Pak
(74) *Attorney, Agent, or Firm* — Saul Ewing LLP; Kathryn Doyle

(57) ABSTRACT

The present invention relates to compositions and methods comprising a chimeric antigen receptor (CAR) capable of binding fibroblast activation protein (FAP) for use in treating diseases, disorders or conditions associated with the expression of FAP on canine, mouse, or human tumor-associated cells.

12 Claims, 21 Drawing Sheets

Specification includes a Sequence Listing.

(56) References Cited

OTHER PUBLICATIONS

Roberts, E. W., et al., "Depletion of stromal cells expressing fibroblast activation protein-[alpha] from skeletal muscle and bone marrow results in cachexia and anemia," J. Exp. Med., vol. 210, No. 6 :1137-1151 (2013).
Cartellier et al., "Chimeric Antigen Receptor-Engineered T Cells for Immunotherapy of Cancer," J Biomed Biotechnol, vol. 2010, Articel ID 956304, pp. 1-13 (2010).
Petrausch, Ulf et al., "Re-directed T cells for the treatment of fibroblast activation protein (FAP)-positive malignant pleural mesothelioma (FAPME-1)," BMC Cancer, 12:615, pp. 1-7 (Dec. 22, 2012).
Shah, Ami et al., "Heart Failure: A Class Review of Pharmacotherapy," P&T, vol. 42, No. 7, pp. 464-472 (Jul. 1, 2017).
Geyer, Mark B. et al. Review: Current clinical applications of chimeric antigen receptor (CAR) modified T cells,' Cytotherapy, vol. 18, No. 11, pp. 1393-1409 (Nov. 2016).
Extended European Search Report, dated of completion Dec. 13, 2021, for European Application No. 18861807.8.
Sun, S. et al., "Immunotherapy with CAR-Modified T Cells: Toxicities and Overcoming Strategies", Immunotherapy and Vaccine Development, vol. 2018, pp. 1-10 (Apr. 17, 2018,).
Wang, L-C. S. et al., "Targeting fibroblast activation protein in tumor stroma with chimeric antigen receptor T cells can inhibit tumor growth and augment host immunity without severe toxicity", Cancer Immunol Res, 2(2):154-166 (2014).
Kaur, H. et al., "Targeted Ablation of Periostin-Expressing Activated Fibroblasts Prevents Adverse Cardiac Remodeling in Mice", Circ Res, 118(12):1906-1917 (2016).
International Search Report and Written Opinion dated Mar. 4, 2019, of counterpart International Application No. PCT/US18/52605.
Xia, A-L, et al., "Chimeric-antigen receptor T (CAR-T) cell therapy for solid tumors: challenges and opportunities", vol. 8, No. 52, pp. 90521-09531, 2017.
Giuliano, A. et al., "Expression of Fibroblast Activating Protein and Correlation with Histological Grade, Mitotic Index and Ki67 Expression in Canine Mast Cell Tumours," J. Comp. Path., vol. 156, p. 14-20 (2017).
Mata, M. et al., "Adapting the Spontaneous Canine Osteosarcoma Model for T-Cell Therapy," Molecular Therapy, vol. 21, Suppl.1, S154, 400 (2013).

* cited by examiner

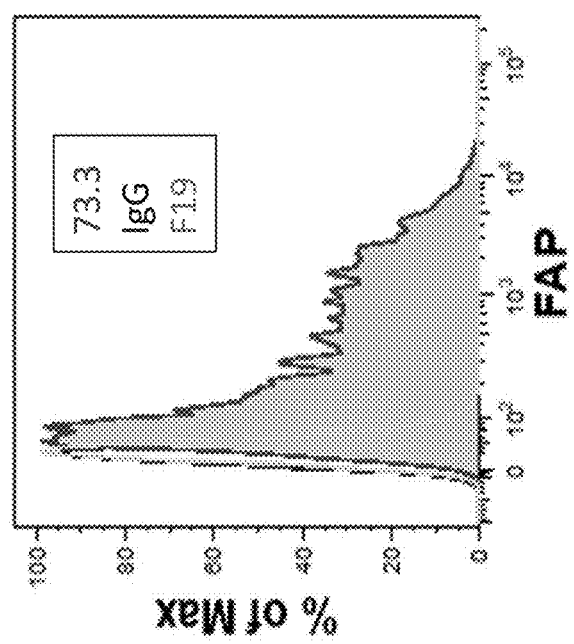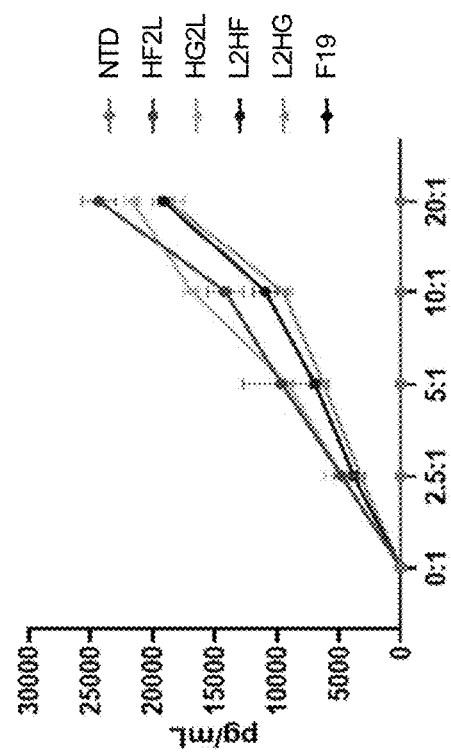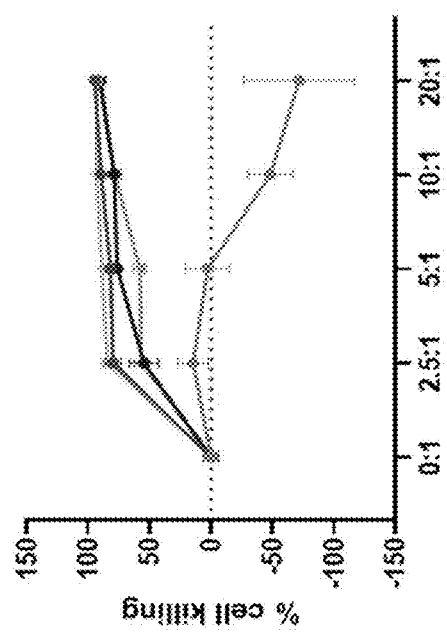
FIG. 6A
FIG. 6B
FIG. 6C

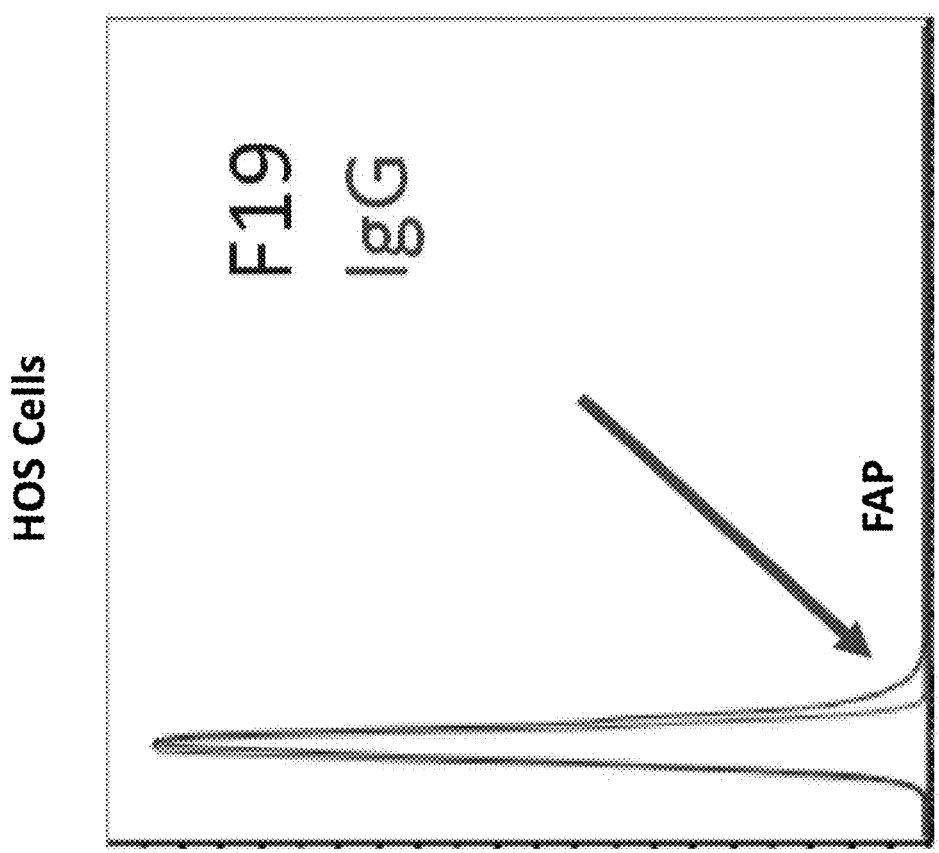

SEQUENCE LISTING

```
<160> NUMBER OF SEQ ID NOS: 60

<210> SEQ ID NO 1
<211> LENGTH: 9
<212> TYPE: PRT
<213> ORGANISM: Artificial Sequence
<220> FEATURE:
<223> OTHER INFORMATION: 4G5 HCDR1

<400> SEQUENCE: 1

Tyr Thr Ile Thr Ser Tyr Ser Leu His
1               5

<210> SEQ ID NO 2
<211> LENGTH: 18
<212> TYPE: PRT
<213> ORGANISM: Artificial Sequence
<220> FEATURE:
<223> OTHER INFORMATION: 4G5 HCDR2

<400> SEQUENCE: 2

Glu Ile Asn Pro Ala Asn Gly Asp His Asn Phe Ser Glu Lys Phe Glu
1               5                   10                  15
```

-continued

Ile Lys

<210> SEQ ID NO 3
<211> LENGTH: 12
<212> TYPE: PRT
<213> ORGANISM: Artificial Sequence
<220> FEATURE:
<223> OTHER INFORMATION: 4G5 HCDR3

<400> SEQUENCE: 3

```
Leu Asp Asp Ser Arg Phe His Trp Tyr Phe Asp Val
1               5                   10
```

<210> SEQ ID NO 4
<211> LENGTH: 10
<212> TYPE: PRT
<213> ORGANISM: Artificial Sequence
<220> FEATURE:
<223> OTHER INFORMATION: 4G5 LCDR1

<400> SEQUENCE: 4

```
Thr Ala Ser Ser Ser Val Ser Tyr Met Tyr
1               5                   10
```

<210> SEQ ID NO 5
<211> LENGTH: 6
<212> TYPE: PRT
<213> ORGANISM: Artificial Sequence
<220> FEATURE:
<223> OTHER INFORMATION: 4G5 LCDR2

<400> SEQUENCE: 5

```
Leu Thr Ser Asn Leu Ala
1               5
```

<210> SEQ ID NO 6
<211> LENGTH: 10
<212> TYPE: PRT
<213> ORGANISM: Artificial Sequence
<220> FEATURE:
<223> OTHER INFORMATION: 4G5 LCDR3

<400> SEQUENCE: 6

```
Gln Gln Trp Ser Gly Tyr Pro Pro Ile Thr
1               5                   10
```

<210> SEQ ID NO 7
<211> LENGTH: 121
<212> TYPE: PRT
<213> ORGANISM: Artificial Sequence
<220> FEATURE:
<223> OTHER INFORMATION: 4G5 VH

<400> SEQUENCE: 7

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Ile Thr Ser Tyr
            20                  25                  30

Ser Leu His Trp Val Lys Gln Arg Pro Gly Gln Gly Leu Glu Trp Ile
        35                  40                  45

Gly Glu Ile Asn Pro Ala Asn Gly Asp His Asn Phe Ser Glu Lys Phe
    50                  55                  60

Glu Ile Lys Ala Thr Leu Thr Val Asp Ser Ser Ser Asn Thr Ala Phe
65                  70                  75                  80
```

```
Met Gln Leu Ser Arg Leu Thr Ser Glu Asp Ser Ala Val Tyr Tyr Cys
            85                  90                  95

Thr Arg Leu Asp Asp Ser Arg Phe His Trp Tyr Phe Asp Val Trp Gly
        100                 105                 110

Ala Gly Thr Thr Val Thr Val Ser Ser
        115                 120

<210> SEQ ID NO 8
<211> LENGTH: 363
<212> TYPE: DNA
<213> ORGANISM: Artificial Sequence
<220> FEATURE:
<223> OTHER INFORMATION: 4G5 VH

<400> SEQUENCE: 8
caggtccaac tgcagcagcc tggggctgaa ctggtaaagc ctggggcttc agtgaagttg      60
tcctgcaagg cgtctggcta caccatcacc agctactctc tgcactgggt gaagcagagg     120
cctggacaag cccttgagtg gattggagag attaatcctg ccaatggtga tcataacttc     180
agtgagaagt tcgagatcaa ggccacactg actgtagaca gctcctccaa cacagcattc     240
atgcaactca gcaggctgac atctgaggac tctgcggtct attactgtac aagattggac     300
gatagtaggt tccactggta cttcgatgtc tggggcgcag ggaccacggt caccgtctcc     360
tca                                                                    363

<210> SEQ ID NO 9
<211> LENGTH: 107
<212> TYPE: PRT
<213> ORGANISM: Artificial Sequence
<220> FEATURE:
<223> OTHER INFORMATION: 4G5 VL

<400> SEQUENCE: 9

Gln Ile Val Leu Thr Gln Ser Pro Ala Leu Met Ser Ala Ser Pro Gly
1               5                   10                  15

Glu Lys Val Thr Met Thr Cys Thr Ala Ser Ser Ser Val Ser Tyr Met
            20                  25                  30

Tyr Trp Tyr Gln Gln Lys Pro Arg Ser Ser Pro Lys Pro Trp Ile Phe
        35                  40                  45

Leu Thr Ser Asn Leu Ala Ser Gly Val Pro Ala Arg Phe Ser Gly Arg
    50                  55                  60

Gly Ser Gly Thr Ser Phe Ser Leu Thr Ile Ser Ser Met Glu Ala Glu
65                  70                  75                  80

Asp Ala Ala Thr Tyr Tyr Cys Gln Gln Trp Ser Gly Tyr Pro Pro Ile
                85                  90                  95

Thr Phe Gly Ser Gly Thr Lys Leu Glu Ile Lys
            100                 105

<210> SEQ ID NO 10
<211> LENGTH: 321
<212> TYPE: DNA
<213> ORGANISM: Artificial Sequence
<220> FEATURE:
<223> OTHER INFORMATION: 4G5 VL

<400> SEQUENCE: 10
caaattgttc tcacccagtc tccagcgctc atgtctgctt ctccagggga gaaggtcacc      60
atgacctgca ctgccagctc aagtgttagt tacatgtact ggtaccagca gaagccacga     120
tcctccccca aaccctggat ttttctcacc tccaacctgg cttctggagt ccctgctcgc     180
```

```
ttcagtggcc gtgggtctgg gacctctttc tctctcacaa tcagcagcat ggaggctgaa      240
gatgctgcca cttattactg ccagcagtgg agtggttacc cacccatcac attcggctcg      300
gggacaaagt tggaaataaa a                                                321
```

<210> SEQ ID NO 11
<211> LENGTH: 243
<212> TYPE: PRT
<213> ORGANISM: Artificial Sequence
<220> FEATURE:
<223> OTHER INFORMATION: 4G5 scFv VLVH

<400> SEQUENCE: 11

```
Gln Ile Val Leu Thr Gln Ser Pro Ala Leu Met Ser Ala Ser Pro Gly
1               5                   10                  15

Glu Lys Val Thr Met Thr Cys Thr Ala Ser Ser Val Ser Tyr Met
            20                  25                  30

Tyr Trp Tyr Gln Gln Lys Pro Arg Ser Ser Pro Lys Pro Trp Ile Phe
        35                  40                  45

Leu Thr Ser Asn Leu Ala Ser Gly Val Pro Ala Arg Phe Ser Gly Arg
    50                  55                  60

Gly Ser Gly Thr Ser Phe Ser Leu Thr Ile Ser Ser Met Glu Ala Glu
65                  70                  75                  80

Asp Ala Ala Thr Tyr Tyr Cys Gln Gln Trp Ser Gly Tyr Pro Pro Ile
                85                  90                  95

Thr Phe Gly Ser Gly Thr Lys Leu Glu Ile Lys Gly Gly Gly Ser
            100                 105                 110

Gly Gly Gly Gly Ser Gly Gly Gly Ser Gln Val Gln Leu Gln Gln
        115                 120                 125

Pro Gly Ala Glu Leu Val Lys Pro Gly Ala Ser Val Lys Leu Ser Cys
    130                 135                 140

Lys Ala Ser Gly Tyr Thr Ile Thr Ser Tyr Ser Leu His Trp Val Lys
145                 150                 155                 160

Gln Arg Pro Gly Gln Gly Leu Glu Trp Ile Gly Glu Ile Asn Pro Ala
                165                 170                 175

Asn Gly Asp His Asn Phe Ser Glu Lys Phe Glu Ile Lys Ala Thr Leu
            180                 185                 190

Thr Val Asp Ser Ser Asn Thr Ala Phe Met Gln Leu Ser Arg Leu
        195                 200                 205

Thr Ser Glu Asp Ser Ala Val Tyr Tyr Cys Thr Arg Leu Asp Asp Ser
    210                 215                 220

Arg Phe His Trp Tyr Phe Asp Val Trp Gly Ala Gly Thr Thr Val Thr
225                 230                 235                 240

Val Ser Ser
```

<210> SEQ ID NO 12
<211> LENGTH: 729
<212> TYPE: DNA
<213> ORGANISM: Artificial Sequence
<220> FEATURE:
<223> OTHER INFORMATION: 4G5 scFv VLVH

<400> SEQUENCE: 12

```
caaattgttc tcacccagtc tccagcgctc atgtctgctt ctccagggga agaggtcacc      60
atgacctgca ctgccagctc aagtgttagt tacatgtact ggtaccagca gaagccacga     120
tcctccccca aaccctggat ttttctcacc tccaacctgg cttctggagt ccctgctcgc     180
```

```
ttcagtggcc gtgggtctgg gacctctttc tctctcacaa tcagcagcat ggaggctgaa    240
gatgctgcca cttattactg ccagcagtgg agtggttacc cacccatcac attcggctcg    300
gggacaaagt tggaaataaa aggtggaggt ggcagcggag gaggtgggtc cggcggtgga    360
ggaagccagg tccaactgca gcagcctggg gctgaactgg taaagcctgg ggcttcagtg    420
aagttgtcct gcaaggcgtc tggctacacc atcaccagct actctctgca ctgggtgaag    480
cagaggcctg gacaaggcct tgagtggatt ggagagatta tcctgccaa tggtgatcat    540 aacttcagtg agaagttcga gatcaaggcc acactgactg tagacagctc ctccaacaca    600
gcattcatgc aactcagcag gctgacatct gaggactctg cggtctatta ctgtacaaga    660
ttggacgata taggttcca ctggtacttc gatgtctggg gcgcaggga cacggtcacc    720 gtctcctca                                                            729
```

<210> SEQ ID NO 13
<211> LENGTH: 243
<212> TYPE: PRT
<213> ORGANISM: Artificial Sequence
<220> FEATURE:
<223> OTHER INFORMATION: 4G5 scFv VHVL
<400> SEQUENCE: 13

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Ile Thr Ser Tyr
            20                  25                  30

Ser Leu His Trp Val Lys Gln Arg Pro Gly Gln Gly Leu Glu Trp Ile
        35                  40                  45

Gly Glu Ile Asn Pro Ala Asn Gly Asp His Asn Phe Ser Glu Lys Phe
    50                  55                  60

Glu Ile Lys Ala Thr Leu Thr Val Asp Ser Ser Ser Asn Thr Ala Phe
65                  70                  75                  80

Met Gln Leu Ser Arg Leu Thr Ser Glu Asp Ser Ala Val Tyr Tyr Cys
                85                  90                  95

Thr Arg Leu Asp Asp Ser Arg Phe His Trp Tyr Phe Asp Val Trp Gly
            100                 105                 110

Ala Gly Thr Thr Val Thr Val Ser Ser Gly Gly Gly Ser Gly Gly
        115                 120                 125

Gly Gly Ser Gly Gly Gly Ser Gln Ile Val Leu Thr Gln Ser Pro
    130                 135                 140

Ala Leu Met Ser Ala Ser Pro Gly Glu Lys Val Thr Met Thr Cys Thr
145                 150                 155                 160

Ala Ser Ser Ser Val Ser Tyr Met Tyr Trp Tyr Gln Gln Lys Pro Arg
                165                 170                 175

Ser Ser Pro Lys Pro Trp Ile Phe Leu Thr Ser Asn Leu Ala Ser Gly
            180                 185                 190

Val Pro Ala Arg Phe Ser Gly Arg Gly Ser Gly Thr Ser Phe Ser Leu
        195                 200                 205

Thr Ile Ser Ser Met Glu Ala Glu Asp Ala Ala Thr Tyr Tyr Cys Gln
    210                 215                 220

Gln Trp Ser Gly Tyr Pro Pro Ile Thr Phe Gly Ser Gly Thr Lys Leu
225                 230                 235                 240

Glu Ile Lys
```

```
<210> SEQ ID NO 14
<211> LENGTH: 729
<212> TYPE: DNA
<213> ORGANISM: Artificial Sequence
<220> FEATURE:
<223> OTHER INFORMATION: 4G5 scFv VHVL

<400> SEQUENCE: 14
caggtccaac tgcagcagcc tggggctgaa ctggtaaagc ctggggcttc agtgaagttg      60
tcctgcaagg cgtctggcta caccatcacc agctactctc tgcactgggt gaagcagagg     120
cctggacaag ccttgagtg gattggagag attaatcctg ccaatggtga tcataacttc      180
agtgagaagt tcgagatcaa ggccacactg actgtagaca gctcctccaa cacagcattc     240
atgcaactca gcaggctgac atctgaggac tctgcggtct attactgtac aagattggac     300
gatagtaggt tccactggta cttcgatgtc tggggcgcag ggaccacggt caccgtctcc     360
tcaggtggag gtggcagcgg aggaggtggg tccggcggtg aggaagccaa aattgttctc     420
acccagtctc cagcgctcat gtctgcttct caggggagat aggtcaccat gacctgcact     480
gccagctcaa gtgttagtta catgtactgg taccagcaga agccacgatc ctcccccaaa     540
ccctggattt ttctcacctc caacctggct tctggagtcc ctgctcgctt cagtggccgt     600
gggtctggga cctctttctc tctcacaatc agcagcatgg aggctgaaga tgctgccact     660
tattactgcc agcagtggag tggttaccca cccatcacat cggctcggg acaaagttg      720 gaaataaaa                                                             729

<210> SEQ ID NO 15
<211> LENGTH: 15
<212> TYPE: PRT
<213> ORGANISM: Artificial Sequence
<220> FEATURE:
<223> OTHER INFORMATION: Linker

<400> SEQUENCE: 15

Gly Gly Gly Gly Ser Gly Gly Gly Gly Ser Gly Gly Gly Gly Ser
1               5                   10                  15

<210> SEQ ID NO 16
<211> LENGTH: 45
<212> TYPE: PRT
<213> ORGANISM: Artificial Sequence
<220> FEATURE:
<223> OTHER INFORMATION: CD8 alpha hinge

<400> SEQUENCE: 16

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 17
<211> LENGTH: 23
<212> TYPE: PRT
<213> ORGANISM: Artificial Sequence
<220> FEATURE:
<223> OTHER INFORMATION: CD8 transmembrane domain

<400> SEQUENCE: 17

Ile Tyr Ile Trp Ala Pro Leu Ala Gly Thr Cys Gly Val Leu Leu Leu
1               5                   10                  15
```

-continued

Ser Leu Val Ile Thr Leu Tyr
            20

<210> SEQ ID NO 18
<211> LENGTH: 41
<212> TYPE: PRT
<213> ORGANISM: Artificial Sequence
<220> FEATURE:
<223> OTHER INFORMATION: 41BB ICD

<400> SEQUENCE: 18

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu
        35                  40

<210> SEQ ID NO 19
<211> LENGTH: 41
<212> TYPE: PRT
<213> ORGANISM: Artificial Sequence
<220> FEATURE:
<223> OTHER INFORMATION: CD28 ICD

<400> SEQUENCE: 19

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 20
<211> LENGTH: 39
<212> TYPE: PRT
<213> ORGANISM: Artificial Sequence
<220> FEATURE:
<223> OTHER INFORMATION: DAP12 ICD

<400> SEQUENCE: 20

Glu Arg Trp Cys Ser Asn Lys Lys Asn Ala Ala Val Met Asp Gln Glu
1               5                   10                  15

Pro Ala Gly Asn Arg Thr Val Asn Ser Glu Asp Ser Asp Glu Gln Asp
            20                  25                  30

His Gln Glu Val Ser Tyr Ala
        35

<210> SEQ ID NO 21
<211> LENGTH: 112
<212> TYPE: PRT
<213> ORGANISM: Artificial Sequence
<220> FEATURE:
<223> OTHER INFORMATION: CD3 zeta ICD

<400> SEQUENCE: 21

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

```
Pro Arg Arg Lys Asn Pro Gln Glu Gly Leu Tyr Asn Glu Leu Gln Lys
     50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

<210> SEQ ID NO 22
<211> LENGTH: 1476
<212> TYPE: DNA
<213> ORGANISM: Artificial Sequence
<220> FEATURE:
<223> OTHER INFORMATION: 4G5HG2LCD8HBBCD3Z CAR

<400> SEQUENCE: 22

```
atggccctgc ctgtgacagc cctgctgctg cctctggctc tgctgctgca tgccgctaga      60
cccggatccc aggtccaact gcagcagcct ggggctgaac tggtaaagcc tggggcttca     120
gtgaagttgt cctgcaaggc gtctggctac accatcacca gctactctct gcactgggtg     180
aagcagaggc ctggacaagg ccttgagtgg attggagaga ttaatcctgc caatggtgat     240
cataacttca gtgagaagtt cgagatcaag gccacactga ctgtagacag ctcctccaac     300
acagcattca tgcaactcag caggctgaca tctgaggact ctgcggtcta ttactgtaca     360
agattggacg atagtaggtt ccactggtac ttcgatgtct ggggcgcagg gaccacggtc     420
accgtctcct caggtggagg tggcagcgga ggaggtgggt ccggcggtgg aggaagccaa     480
attgttctca cccagtctcc agcgctcatg tctgcttctc aggggagaa  ggtcaccatg     540
acctgcactg ccagctcaag tgttagttac atgtactggt accagcagaa gccacgatcc     600
tcccccaaac cctggatttt tctcacctcc aacctggctt ctggagtccc tgctcgcttc     660
agtggccgtg gatctgggac ctctttctct ctcacaatca gcagcatgga ggctgaagat     720
gctgccactt attactgcca gcagtggagt ggttacccac ccatcacatt cggctcgggg     780
acaaagttgg aaataaaatc cggaaccacg acgccagcgc cgcgaccacc aacaccggcg     840
cccaccatcg cgtcgcagcc cctgtccctg cgcccagagg cgtgccggcc agcggcgggg     900
ggcgcagtgc acacgagggg gctggacttc gcctgtgata tctacatctg ggcgcccttg     960
gccgggactt gtggggtcct tctcctgtca ctggttatca cccttactgc aaacgggcc     1020
agaaagaaac tcctgtatat attcaaacaa ccatttatga gaccagtaca aactactcaa     1080
gaggaagatg gctgtagctg ccgatttcca gaagaagaag aaggaggatg tgaactgaga     1140
gtgaagttca gcaggagcgc agacgccccc gcgtacaagc agggccagaa ccagctctat     1200
aacgagctca atctaggacg aagagaggag tacgatgttt tggacaagag acgtggccgg     1260
gacccgaga  tggggggaaa gccgagaagg aagaaccctc aggaaggcct gtacaatgaa     1320
ctgcagaaag ataagatggc ggaggcctac agtgagattg gcatgaaagg cgagcgccgg     1380
aggggcaagg ggcacgatgg cctttaccag ggtctcagta cagccaccaa ggacacctac     1440
gacgccttc  acatgcaggc cctgccccct cgctaa                                1476
```

<210> SEQ ID NO 23
<211> LENGTH: 491
<212> TYPE: PRT
<213> ORGANISM: Artificial Sequence
<220> FEATURE:

<223> OTHER INFORMATION: 4G5HG2LCD8HBBCD3Z CAR

<400> SEQUENCE: 23

```
Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Pro Gly Ala
            20                  25                  30

Glu Leu Val Lys Pro Gly Ala Ser Val Lys Leu Ser Cys Lys Ala Ser
        35                  40                  45

Gly Tyr Thr Ile Thr Ser Tyr Ser Leu His Trp Val Lys Gln Arg Pro
50                  55                  60

Gly Gln Gly Leu Glu Trp Ile Gly Glu Ile Asn Pro Ala Asn Gly Asp
65                  70                  75                  80

His Asn Phe Ser Glu Lys Phe Glu Ile Lys Ala Thr Leu Thr Val Asp
            85                  90                  95

Ser Ser Ser Asn Thr Ala Phe Met Gln Leu Ser Arg Leu Thr Ser Glu
            100                 105                 110

Asp Ser Ala Val Tyr Tyr Cys Thr Arg Leu Asp Asp Ser Arg Phe His
        115                 120                 125

Trp Tyr Phe Asp Val Trp Gly Ala Gly Thr Thr Val Thr Val Ser Ser
130                 135                 140

Gly Gly Gly Gly Ser Gly Gly Gly Ser Gly Gly Gly Gly Ser Gln
145                 150                 155                 160

Ile Val Leu Thr Gln Ser Pro Ala Leu Met Ser Ala Ser Pro Gly Glu
            165                 170                 175

Lys Val Thr Met Thr Cys Thr Ala Ser Ser Ser Val Ser Tyr Met Tyr
        180                 185                 190

Trp Tyr Gln Gln Lys Pro Arg Ser Ser Pro Lys Pro Trp Ile Phe Leu
            195                 200                 205

Thr Ser Asn Leu Ala Ser Gly Val Pro Ala Arg Phe Ser Gly Arg Gly
210                 215                 220

Ser Gly Thr Ser Phe Ser Leu Thr Ile Ser Ser Met Glu Ala Glu Asp
225                 230                 235                 240

Ala Ala Thr Tyr Tyr Cys Gln Gln Trp Ser Gly Tyr Pro Pro Ile Thr
            245                 250                 255

Phe Gly Ser Gly Thr Lys Leu Glu Ile Lys Ser Gly Thr Thr Thr Pro
        260                 265                 270

Ala Pro Arg Pro Pro Thr Pro Ala Pro Thr Ile Ala Ser Gln Pro Leu
            275                 280                 285

Ser Leu Arg Pro Glu Ala Cys Arg Pro Ala Ala Gly Gly Ala Val His
290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
            325                 330                 335

Cys Lys Arg Gly Arg Lys Lys Leu Leu Tyr Ile Phe Lys Gln Pro Phe
        340                 345                 350

Met Arg Pro Val Gln Thr Thr Gln Glu Glu Asp Gly Cys Ser Cys Arg
            355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Lys Gln Gly Gln Asn Gln Leu Tyr
385                 390                 395                 400
```

```
Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 24
<211> LENGTH: 1476
<212> TYPE: DNA
<213> ORGANISM: Artificial Sequence
<220> FEATURE:
<223> OTHER INFORMATION: 4G5L2HGCD8HBBCD3Z CAR

<400> SEQUENCE: 24
atggccctgc ctgtgacagc cctgctgctg cctctggctc tgctgctgca tgccgctaga      60
cccggatccc aaattgttct cacccagtct ccagcgctca tgtctgcttc tccaggggag     120
aaggtcacca tgacctgcac tgccagctca agtgttagtt acatgtactg gtaccagcag     180
aagccacgat cctcccccaa accctggatt tttctcacct ccaacctggc ttctggagtc     240
cctgctcgct tcagtggccg tgggtctggg acctctttct ctctcacaat cagcagcatg     300
gaggctgaag atgctgccac ttattactgc cagcagtgga gtggttaccc acccatcaca     360
ttcggctcgg gacaaagtt ggaaataaaa ggtggaggtg gcagcggagg aggtgggtcc     420
ggcggtggag gaagccaggt ccaactgcag cagcctgggg ctgaactggt aaagcctggg     480
gcttcagtga agttgtcctg caaggcgtct ggctacacca tcaccagcta ctctctgcac     540
tgggtgaagc agaggcctgg acaaggcctt gagtggattg agagattaa tcctgccaat     600 ggtgatcata acttcagtga aagttcgag atcaaggcca cactgactgt agacagctcc     660
tccaacacag cattcatgca actcagcagg ctgacatctg aggactctgc ggtctattac     720
tgtacaagat ggacgatag taggttccac tggtacttcg atgtctgggg cgcagggacc     780
acggtcaccg tctcctcatc cggaaccacg acgccagcgc cgcgaccacc aacaccggcg     840
cccaccatcg cgtcgcagcc cctgtccctg cgcccagagg cgtgccggcc agcggcgggg     900
ggcgcagtgc acacgagggg gctggacttc gcctgtgata tctacatctg ggcgcccttg     960
gccgggactt gtggggtcct tctcctgtca ctggttatca ccctttactg caaacggggc    1020
agaaagaaac tcctgtatat attcaaacaa ccatttatga ccagtacaa aactactcaa    1080 gaggaagatg gctgtagctg ccgatttcca gaagaagaag aaggaggatg tgaactgaga    1140
gtgaagttca gcaggagcgc agacgccccc gcgtacaagc agggccagaa ccagctctat    1200
aacgagctca atctaggacg aagagaggag tacgatgttt tggacaagag acgtggccgg    1260
gaccctgaga tggggggaaa gccgagaagg aagaaccctc aggaaggcct gtacaatgaa    1320
ctgcagaaag ataagatggc ggaggcctac agtgagattg gatgaaagg cgagcgccgg    1380 aggggcaagg ggcacgatgg cctttaccag ggtctcagta cagccaccaa ggacacctac    1440
gacgcccttc acatgcaggc cctgcccct cgctaa                              1476
```

<210> SEQ ID NO 25
<211> LENGTH: 491
<212> TYPE: PRT
<213> ORGANISM: Artificial Sequence
<220> FEATURE:
<223> OTHER INFORMATION: 4G5L2HGCD8HBBCD3Z CAR

<400> SEQUENCE: 25

```
Met Ala Leu Pro Val Thr Ala Leu Leu Leu Pro Leu Ala Leu Leu Leu
1               5                   10                  15

His Ala Ala Arg Pro Gly Ser Gln Ile Val Leu Thr Gln Ser Pro Ala
            20                  25                  30

Leu Met Ser Ala Ser Pro Gly Glu Lys Val Thr Met Thr Cys Thr Ala
        35                  40                  45

Ser Ser Ser Val Ser Tyr Met Tyr Trp Tyr Gln Gln Lys Pro Arg Ser
    50                  55                  60

Ser Pro Lys Pro Trp Ile Phe Leu Thr Ser Asn Leu Ala Ser Gly Val
65                  70                  75                  80

Pro Ala Arg Phe Ser Gly Arg Gly Ser Gly Thr Ser Phe Ser Leu Thr
                85                  90                  95

Ile Ser Ser Met Glu Ala Glu Asp Ala Ala Thr Tyr Tyr Cys Gln Gln
            100                 105                 110

Trp Ser Gly Tyr Pro Pro Ile Thr Phe Gly Ser Gly Thr Lys Leu Glu
        115                 120                 125

Ile Lys Gly Gly Gly Gly Ser Gly Gly Gly Gly Ser Gly Gly Gly Gly
    130                 135                 140

Ser Gln Val Gln Leu Gln Gln Pro Gly Ala Glu Leu Val Lys Pro Gly
145                 150                 155                 160

Ala Ser Val Lys Leu Ser Cys Lys Ala Ser Gly Tyr Thr Ile Thr Ser
                165                 170                 175

Tyr Ser Leu His Trp Val Lys Gln Arg Pro Gly Gln Gly Leu Glu Trp
            180                 185                 190

Ile Gly Glu Ile Asn Pro Ala Asn Gly Asp His Asn Phe Ser Glu Lys
        195                 200                 205

Phe Glu Ile Lys Ala Thr Leu Thr Val Asp Ser Ser Ser Asn Thr Ala
    210                 215                 220

Phe Met Gln Leu Ser Arg Leu Thr Ser Glu Asp Ser Ala Val Tyr Tyr
225                 230                 235                 240

Cys Thr Arg Leu Asp Asp Ser Arg Phe His Trp Tyr Phe Asp Val Trp
                245                 250                 255

Gly Ala Gly Thr Thr Val Thr Val Ser Ser Ser Gly Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
```

```
              370                 375                 380
Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
                420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
            450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 26
<211> LENGTH: 2283
<212> TYPE: DNA
<213> ORGANISM: Artificial Sequence
<220> FEATURE:
<223> OTHER INFORMATION: Full Length Canine FAP

<400> SEQUENCE: 26
atgaagacgt ggttaaaaat tgtatttgga gttgccacct ctgctgtgct tgctttattg      60
gtgatgtgca ttgtcttacg tccttcaaga gttcatgact ccgaaggagg tacaacaaga     120
gcactcacac tggaggatat tttaaatggg acatttacct ataaaacatt ttttccaaac     180
tggatttcag acaagaata tcttcatcag tctacagata tggatatagt atattacaat     240
attgaaacag agaatcata taccattttg agtaatgcca ccatgaaaag tgtgaatgct     300
tcaaattatg gctatcacc tgatcgtcaa tttgcatatc tagaaagtga ttattcaaag     360
ctttggagat actcttacac tgcaacatat cacatctata acctcaataa tggagagttt     420
ataagaagaa atgagcttcc tcgtccaatt cagtatttat gctggtcgcc tgttgggagt     480
aaattagcat atgtctatca aaacaatatc tatttgaaac aaagaccaga agacccacct     540
tttcaaataa catataatgg aagagaaaat aaaatattca atggaatccc agactgggta     600
tatgaagagg aaatgcttgc tacaaaacat gctctctggt ggtctcctaa ggaaaatttt     660
ttggcatatg cagaatttaa tgatacagag ataccagtta ttgcctattc ctattatggt     720
gatgaacaat atcctagaac aataaatatt ccatacccaa aggctggagc taagaaccct     780
gttgttcgga tctttattat cgataccact tatcctcagc agacaggtcc cagagaagtg     840
ccagttccag caatgatagc atcaagtgat tattatttca gttggctcac atgggttact     900
gatgaacgag tatgtttgca gtggctaaaa agaatccaga acgtttcagt tctgtccata     960
tgtgatttca gggaaggctg gcagacatgg gattgtccaa aggcccagga acatatagaa    1020
gaaagcagaa ctggatgggc tggtggattc tttgtttcaa caccagtttt cagctatgat    1080
gccatttcat actacaaaat atttagcgac aaggatggct acaaacatat tcactatatc    1140
aaagacactg tggaaaatgc tattcaaatt acaagtggca gtgggaggc cataaatata    1200 ttcagagtaa cacaggattc actgttttat tctagcaatg aatttgaaga ctacccagga    1260
agaagaaata tctatagaat tagcattgga agctctcctc caagcaaaaa gtgcattact    1320
tgccatctaa ggaaagaaag gtgccaatat tacacagcaa gtttcagtga ctacgccaag    1380
```

```
tactatgcac ttatctgcta tggcccaggc ctccccattt ccaccttca tgacggccac    1440 actgatcaag aaattaaaat cctggaagaa aacaaagaat tggaaaatgc tttgaaaaat    1500
atccagctgc ctaaagagga aattaagaaa cttgaagtgg atgatattac tttatggtac    1560
aagatgatga ttcctccccg gtttgacaga tcaaagaagt atcccttgct aattcaagtg    1620
tatggtggtc cctgcagtca gagcgtaaag tctgtattca gtattaattg gatttcttat    1680
cttgcaagta aggaagggat agtcattgcc ttggtggatg gccgaggaac agcttaccaa    1740
ggtgacaaac tcctgtatgc agtatatcga aagctgggtg tttatgaagt tgaggaccag    1800
atcacagccg tcagaaaatt catagaaatg ggtttcattg atgaaaaag aatagccata    1860 tggggctggt cctatggagg ctatgtttca tcactggccc ttgcttcagg aactggtctt    1920
ttcaaatgtg ggatagcagt ggctcctgtc tccagctggg aatattacgc atctatctac    1980
acagaacgat tcatgggcct cccaacaaag aacgataatc tcgagcacta caaaaattca    2040
actgtgatgg caagagcaga atatttcaga aatgtagact atcttctcat ccacggaaca    2100
gcagatgata atgtgcactt tcaaaactca gcacagattg ctaaagctct ggttaatgca    2160
caagtggatt ccaggcaat gtggtactct gaccagaacc atggcatacc cggcctgtcc    2220
tcgaagcact atatacccg catgacccac ttcctaaagc agtgttttc tttgtccgac    2280 tga                                                                  2283

<210> SEQ ID NO 27
<211> LENGTH: 10
<212> TYPE: PRT
<213> ORGANISM: Artificial Sequence
<220> FEATURE:
<223> OTHER INFORMATION: 4G5 HCDR1

<400> SEQUENCE: 27

Gly Tyr Thr Ile Thr Ser Tyr Ser Leu His
1               5                   10

<210> SEQ ID NO 28
<211> LENGTH: 20
<212> TYPE: PRT
<213> ORGANISM: Artificial Sequence
<220> FEATURE:
<223> OTHER INFORMATION: 4G5 HCDR2

<400> SEQUENCE: 28

Glu Ile Asn Pro Ala Asn Gly Asp His Asn Phe Ser Glu Lys Phe Glu
1               5                   10                  15

Ile Lys Ala Thr
            20

<210> SEQ ID NO 29
<211> LENGTH: 14
<212> TYPE: PRT
<213> ORGANISM: Artificial Sequence
<220> FEATURE:
<223> OTHER INFORMATION: 4G5 HCDR3

<400> SEQUENCE: 29

Thr Arg Leu Asp Asp Ser Arg Phe His Trp Tyr Phe Asp Val
1               5                   10

<210> SEQ ID NO 30
<211> LENGTH: 7
<212> TYPE: PRT
<213> ORGANISM: Artificial Sequence
```

```
<220> FEATURE:
<223> OTHER INFORMATION: 4G5 LCDR2

<400> SEQUENCE: 30

Leu Thr Ser Asn Leu Ala Ser
1               5

<210> SEQ ID NO 31
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: repeat n times, where n represents an integer
      of at least 1

<400> SEQUENCE: 31

Gly Ser Gly Gly Ser
1               5

<210> SEQ ID NO 32
<211> LENGTH: 4
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(4)
<223> OTHER INFORMATION: repeat n times, where n represents an integer
      of at least 1

<400> SEQUENCE: 32

Gly Gly Gly Ser
1

<210> SEQ ID NO 33
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: repeat n times, where n represents an integer
      of at least 1

<400> SEQUENCE: 33

Gly Gly Gly Gly Ser
1               5

<210> SEQ ID NO 34
<211> LENGTH: 4
<212> TYPE: PRT
<213> ORGANISM: Artificial Sequence
<220> FEATURE:
<223> OTHER INFORMATION: Linker

<400> SEQUENCE: 34

Gly Gly Ser Gly
1

<210> SEQ ID NO 35
<211> LENGTH: 5
<212> TYPE: PRT
```

```
<213> ORGANISM: Artificial Sequence
<220> FEATURE:
<223> OTHER INFORMATION: Linker

<400> SEQUENCE: 35

Gly Gly Ser Gly Gly
1               5

<210> SEQ ID NO 36
<211> LENGTH: 5
<212> TYPE: PRT
<213> ORGANISM: Artificial Sequence
<220> FEATURE:
<223> OTHER INFORMATION: Linker

<400> SEQUENCE: 36

Gly Ser Gly Ser Gly
1               5

<210> SEQ ID NO 37
<211> LENGTH: 5
<212> TYPE: PRT
<213> ORGANISM: Artificial Sequence
<220> FEATURE:
<223> OTHER INFORMATION: Linker

<400> SEQUENCE: 37

Gly Ser Gly Gly Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Linker

<400> SEQUENCE: 38

Gly Gly Gly Ser Gly
1               5

<210> SEQ ID NO 39
<211> LENGTH: 5
<212> TYPE: PRT
<213> ORGANISM: Artificial Sequence
<220> FEATURE:
<223> OTHER INFORMATION: Linker

<400> SEQUENCE: 39

Gly Ser Ser Ser Gly
1               5

<210> SEQ ID NO 40
<211> LENGTH: 5
<212> TYPE: PRT
<213> ORGANISM: Artificial Sequence
<220> FEATURE:
<223> OTHER INFORMATION: Linker

<400> SEQUENCE: 40

Gly Gly Gly Gly Ser
1               5

<210> SEQ ID NO 41
<211> LENGTH: 45
<212> TYPE: DNA
<213> ORGANISM: Artificial Sequence
```

-continued

<220> FEATURE:
<223> OTHER INFORMATION: Linker

<400> SEQUENCE: 41
ggtggcggtg gctcgggcgg tggtgggtcg ggtggcggcg gatct          45

<210> SEQ ID NO 42
<211> LENGTH: 5
<212> TYPE: PRT
<213> ORGANISM: Artificial Sequence
<220> FEATURE:
<223> OTHER INFORMATION: Hinge

<400> SEQUENCE: 42

Asp Lys Thr His Thr
1               5

<210> SEQ ID NO 43
<211> LENGTH: 4
<212> TYPE: PRT
<213> ORGANISM: Artificial Sequence
<220> FEATURE:
<223> OTHER INFORMATION: Hinge

<400> SEQUENCE: 43

Cys Pro Pro Cys
1

<210> SEQ ID NO 44
<211> LENGTH: 15
<212> TYPE: PRT
<213> ORGANISM: Artificial Sequence
<220> FEATURE:
<223> OTHER INFORMATION: Hinge

<400> SEQUENCE: 44

Cys Pro Glu Pro Lys Ser Cys Asp Thr Pro Pro Cys Pro Arg
1               5                   10                  15

<210> SEQ ID NO 45
<211> LENGTH: 12
<212> TYPE: PRT
<213> ORGANISM: Artificial Sequence
<220> FEATURE:
<223> OTHER INFORMATION: Hinge

<400> SEQUENCE: 45

Glu Leu Lys Thr Pro Leu Gly Asp Thr Thr His Thr
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Hinge

<400> SEQUENCE: 46

Lys Ser Cys Asp Lys Thr His Thr Cys Pro
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Hinge

<400> SEQUENCE: 47

Lys Cys Cys Val Asp Cys Pro
1               5

<210> SEQ ID NO 48
<211> LENGTH: 7
<212> TYPE: PRT
<213> ORGANISM: Artificial Sequence
<220> FEATURE:
<223> OTHER INFORMATION: Hinge

<400> SEQUENCE: 48

Lys Tyr Gly Pro Pro Cys Pro
1               5

<210> SEQ ID NO 49
<211> LENGTH: 15
<212> TYPE: PRT
<213> ORGANISM: Artificial Sequence
<220> FEATURE:
<223> OTHER INFORMATION: Hinge

<400> SEQUENCE: 49

Glu Pro Lys Ser Cys Asp Lys Thr His Thr Cys Pro Pro Cys Pro
1               5                   10                  15

<210> SEQ ID NO 50
<211> LENGTH: 12
<212> TYPE: PRT
<213> ORGANISM: Artificial Sequence
<220> FEATURE:
<223> OTHER INFORMATION: Hinge

<400> SEQUENCE: 50

Glu Arg Lys Cys Cys Val Glu Cys Pro Pro Cys Pro
1               5                   10

<210> SEQ ID NO 51
<211> LENGTH: 17
<212> TYPE: PRT
<213> ORGANISM: Artificial Sequence
<220> FEATURE:
<223> OTHER INFORMATION: Hinge

<400> SEQUENCE: 51

Glu Leu Lys Thr Pro Leu Gly Asp Thr Thr His Thr Cys Pro Arg Cys
1               5                   10                  15

Pro

<210> SEQ ID NO 52
<211> LENGTH: 12
<212> TYPE: PRT
<213> ORGANISM: Artificial Sequence
<220> FEATURE:
<223> OTHER INFORMATION: Hinge

<400> SEQUENCE: 52

Ser Pro Asn Met Val Pro His Ala His His Ala Gln
1               5                   10

<210> SEQ ID NO 53
<211> LENGTH: 15
<212> TYPE: PRT
<213> ORGANISM: Artificial Sequence
<220> FEATURE:

<223> OTHER INFORMATION: Hinge

<400> SEQUENCE: 53

Glu Pro Lys Ser Cys Asp Lys Thr Tyr Thr Cys Pro Pro Cys Pro
1               5                   10                  15

<210> SEQ ID NO 54
<211> LENGTH: 22
<212> TYPE: DNA
<213> ORGANISM: Artificial Sequence
<220> FEATURE:
<223> OTHER INFORMATION: Primer

<400> SEQUENCE: 54
atgtagacgt ggttaaaaat tg                                                    22

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
cgtcatcttc agtcggacaa                                                       20

<210> SEQ ID NO 56
<211> LENGTH: 760
<212> TYPE: PRT
<213> ORGANISM: Canis lupus familiaris
<220> FEATURE:
<223> OTHER INFORMATION: FAP protein

<400> SEQUENCE: 56

Met Lys Thr Trp Leu Lys Ile Val Phe Gly Val Ala Thr Ser Ala Val
1               5                   10                  15

Leu Ala Leu Leu Val Met Cys Ile Val Leu Arg Pro Ser Arg Val His
                20                  25                  30

Asp Ser Glu Gly Gly Thr Thr Arg Ala Leu Thr Leu Glu Asp Ile Leu
            35                  40                  45

Asn Gly Thr Phe Thr Tyr Lys Thr Phe Phe Pro Asn Trp Ile Ser Gly
        50                  55                  60

Gln Glu Tyr Leu His Gln Ser Thr Asp Asn Asp Ile Val Tyr Tyr Asn
65                  70                  75                  80

Ile Glu Thr Gly Glu Ser Tyr Thr Ile Leu Ser Asn Ala Thr Met Lys
                85                  90                  95

Ser Val Asn Ala Ser Asn Tyr Gly Leu Ser Pro Asp Arg Gln Phe Ala
                100                 105                 110

Tyr Leu Glu Ser Asp Tyr Ser Lys Leu Trp Arg Tyr Ser Tyr Thr Ala
            115                 120                 125

Thr Tyr His Ile Tyr Asn Leu Asn Asn Gly Glu Phe Ile Arg Arg Asn
        130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Glu Asp Pro Pro Phe Gln Ile Thr Tyr Asn Gly Arg Glu Asn Lys Ile
            180                 185                 190

Phe Asn Gly Ile Pro Asp Trp Val Tyr Glu Glu Glu Met Leu Ala Thr
        195                 200                 205

```
Lys His Ala Leu Trp Trp Ser Pro Asn Gly Lys Phe Leu Ala Tyr Ala
210                 215                 220

Glu Phe Asn Asp Thr Glu Ile Pro Val Ile Ala Tyr Ser Tyr Tyr Gly
225                 230                 235                 240

Asp Glu Gln Tyr Pro Arg Thr Ile Asn Ile Pro Tyr Pro Lys Ala Gly
                245                 250                 255

Ala Lys Asn Pro Val Val Arg Ile Phe Ile Ile Asp Thr Thr Tyr Pro
            260                 265                 270

Gln Gln Thr Gly Pro Arg Glu Val Pro Val Pro Ala Met Ile Ala Ser
        275                 280                 285

Ser Asp Tyr Tyr Phe Ser Trp Leu Thr Trp Val Thr Asp Glu Arg Val
290                 295                 300

Cys Leu Gln Trp Leu Lys Arg Ile Gln Asn Val Ser Val Leu Ser Ile
305                 310                 315                 320

Cys Asp Phe Arg Glu Gly Trp Gln Thr Trp Asp Cys Pro Lys Ala Gln
                325                 330                 335

Glu His Ile Glu Glu Ser Arg Thr Gly Trp Ala Gly Phe Phe Val
            340                 345                 350

Ser Thr Pro Val Phe Ser Tyr Asp Ala Ile Ser Tyr Tyr Lys Ile Phe
        355                 360                 365

Ser Asp Lys Asp Gly Tyr Lys His Ile His Tyr Ile Lys Asp Thr Val
370                 375                 380

Glu Asn Ala Ile Gln Ile Thr Ser Gly Lys Trp Glu Ala Ile Asn Ile
385                 390                 395                 400

Phe Arg Val Thr Gln Asp Ser Leu Phe Tyr Ser Asn Glu Phe Glu
                405                 410                 415

Asp Tyr Pro Gly Arg Arg Asn Ile Tyr Arg Ile Ser Ile Gly Ser Ser
            420                 425                 430

Pro Pro Ser Lys Lys Cys Ile Thr Cys His Leu Arg Lys Glu Arg Cys
        435                 440                 445

Gln Tyr Tyr Thr Ala Ser Phe Ser Asp Tyr Ala Lys Tyr Tyr Ala Leu
        450                 455                 460

Ile Cys Tyr Gly Pro Gly Leu Pro Ile Ser Thr Leu His Asp Gly His
465                 470                 475                 480

Thr Asp Gln Glu Ile Lys Ile Leu Glu Glu Asn Lys Glu Leu Glu Asn
                485                 490                 495

Ala Leu Lys Asn Ile Gln Leu Pro Lys Glu Ile Lys Lys Leu Glu
            500                 505                 510

Val Asp Ile Thr Leu Trp Tyr Lys Met Met Leu Pro Pro Arg Phe
            515                 520                 525

Asp Arg Ser Lys Lys Tyr Pro Leu Leu Ile Gln Val Tyr Gly Gly Pro
530                 535                 540

Cys Ser Gln Ser Val Lys Ser Val Phe Ser Ile Asn Trp Ile Ser Tyr
545                 550                 555                 560

Leu Ala Ser Lys Glu Gly Ile Val Ile Ala Leu Val Asp Gly Arg Gly
                565                 570                 575

Thr Ala Tyr Gln Gly Asp Lys Leu Leu Tyr Ala Val Tyr Arg Lys Leu
            580                 585                 590

Gly Val Tyr Glu Val Glu Asp Gln Ile Thr Ala Val Arg Lys Phe Ile
        595                 600                 605

Glu Met Gly Phe Ile Asp Glu Lys Arg Ile Ala Ile Trp Gly Trp Ser
610                 615                 620
```

-continued

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Ala Ser Ile Tyr Thr Glu Arg Phe Met Gly Leu Pro Thr Lys Asn Asp
            660                 665                 670

Asn Leu Glu His Tyr Lys Asn Ser Thr Val Met Ala Arg Ala Glu Tyr
        675                 680                 685

Phe Arg Asn Val Asp Tyr Leu Leu Ile His Gly Thr Ala Asp Asp Asn
690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Ile
                725                 730                 735

Pro Gly Leu Ser Ser Lys His Leu Tyr Thr Arg Met Thr His Phe Leu
            740                 745                 750

Lys Gln Cys Phe Ser Leu Ser Asp
755                 760

<210> SEQ ID NO 57
<211> LENGTH: 30
<212> TYPE: DNA
<213> ORGANISM: Artificial Sequence
<220> FEATURE:
<223> OTHER INFORMATION: T127

<400> SEQUENCE: 57
ctttggagat actcttacac agcaacatat                                    30

<210> SEQ ID NO 58
<211> LENGTH: 30
<212> TYPE: DNA
<213> ORGANISM: Artificial Sequence
<220> FEATURE:
<223> OTHER INFORMATION: T127

<400> SEQUENCE: 58
ctttggagat actcttacac tgcaacatat                                    30

<210> SEQ ID NO 59
<211> LENGTH: 28
<212> TYPE: DNA
<213> ORGANISM: Artificial Sequence
<220> FEATURE:
<223> OTHER INFORMATION: A603

<400> SEQUENCE: 59
atcacagctg tcagaaaatt catagaaa                                      28

<210> SEQ ID NO 60
<211> LENGTH: 28
<212> TYPE: DNA
<213> ORGANISM: Artificial Sequence
<220> FEATURE:
<223> OTHER INFORMATION: A603

<400> SEQUENCE: 60
atcacagccg tcagaaaatt catagaaa                                      28

DISRUPTING TUMOR TISSUES BY TARGETING FIBROBLAST ACTIVATION PROTEIN (FAP)

CROSS-REFERENCE TO RELATED APPLICATION

The present application is entitled to priority under 35 U.S.C. § 119(e) to U.S. Provisional Patent Application No. 62/904,340 filed Sep. 23, 2019, which is hereby incorporated by reference in its entirety herein.

STATEMENT REGARDING FEDERALLY SPONSORED RESEARCH OF DEVELOPMENT

This invention was made with government support under CA172921 and CA217805 awarded by the National Institutes of Health. The government has certain rights in the invention.

REFERENCE TO AN ELECTRONIC SEQUENCE LISTING

The contents of the electronic sequence listing (File Name: 046483-7273US1 Sequence Listing.txt; Size: 43,469 bytes; and Date of Creation: Sep. 25, 2023) is incorporated herein by reference in its entirety.

BACKGROUND OF THE INVENTION

Tumors are composed of heterogeneous populations of cells, including transformed cells and a multitude of untransformed cells. Although the prevalence of different cell types varies among tumors and at different stages of tumor progression, they include infiltrating inflammatory and immune cells, endothelial cells and mesenchymal-derived smooth muscle cells, pericytes, and tumor-associated fibroblasts (TAFs). TAFs are a heterogeneous population that can be phenotypically distinguished from normal fibroblasts. Fibroblast activation protein (FAP) has emerged as a marker of reactive fibroblasts in tumors as well as granulation tissue and in fibrotic lesions.

FAP is a type II transmembrane cell surface protein belonging to the post-proline dipeptidyl aminopeptidase family, sharing the highest similarity with dipeptidyl peptidase IV (DPPIV/CD26). FAP is expressed selectively by TAFs and pericytes in more than 90% of human epithelial cancers examined. It is also expressed during embryonic development, in tissues of healing wounds, and in chronic inflammatory and fibrotic conditions such as liver cirrhosis and idiopathic pulmonary fibrosis, as well as on bone and soft tissue sarcomas and some melanomas. Expression of FAP is not however detected in benign lesions or normal adult tissues, while DPPIV is more widely expressed in a variety of cell types. In vitro studies have shown that FAP has both dipeptidyl peptidase and endopeptidase activity, including a collagenolytic activity capable of degrading gelatin and type I collagen, but it's in vivo substrate(s) is yet to be defined.

There is a need in the art for the development of therapies that treat cancer by directly targeting FAP expressed by tumor-associated cells. The present invention addresses this need.

SUMMARY OF THE INVENTION

As described herein, the present invention relates to compositions and methods comprising a chimeric antigen receptor (CAR) capable of binding fibroblast activation protein (FAP) for use in treating diseases, disorders or conditions associated with the expression of FAP on canine, mouse, or human tumor-associated cells.

In one aspect, the invention provides a chimeric antigen receptor (CAR) comprising an antigen-binding domain capable of binding Fibroblast Activation Protein (FAP), a transmembrane domain, and an intracellular domain. The antigen-binding domain comprises a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), a LCDR2 comprises the amino acid sequence LTSNLA (SEQ ID NO: 5), and LCDR3 comprises the amino acid sequence QQWSGYPPIT (SEQ ID NO: 6).

In certain embodiments, the antigen-binding domain comprises: (a) a heavy chain variable region comprising an amino acid sequence at least 80%, 85%, 90%, 95%, 96%, 97%, 98%, 99%, or 100% identical to SEQ ID NO: 7; and/or (b) a light chain variable region comprising an amino acid sequence at least 80%, 85%, 90%, 95%, 96%, 97%, 98%, 99%, or 100% identical to SEQ ID NO: 9; and/or (c) a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9; and/or (d) an antigen-binding domain selected from the group consisting of a full-length antibody or antigen-binding fragment thereof, a Fab, a single-chain variable fragment (scFv), or a single-domain antibody; and/or (e) a single-chain variable fragment (scFv) comprising an amino acid sequence at least 80%, 85%, 90%, 95%, 96%, 97%, 98%, 99%, or 100% identical to SEQ ID NO: 11 or 13.

In certain embodiments, the CAR: (a) is capable of binding to fibroblast activation protein (FAP); and/or (b) is capable of binding human FAP; and/or (c) is capable of binding canine FAP; and/or (d) is capable of binding murine FAP; and/or (e) is capable of binding human, canine, and murine FAP; and/or (f) further comprises a hinge domain, wherein the hinge domain comprises a hinge domain of CD8 alpha.

In certain embodiments, the transmembrane domain: (a) is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), ICOS (CD278), and CD154, or a transmembrane domain derived from a killer immunoglobulin-like receptor (KIR); and/or (b) comprises a transmembrane domain of CD8; and/or (c) comprises a transmembrane domain of CD8 alpha; and/or (d) comprises a transmembrane domain derived from a killer immunoglobulin-like receptor (KIR).

In certain embodiments, the intracellular domain: (a) comprises a costimulatory signaling domain and an intracellular signaling domain; and/or (b) comprises one or more of a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS (CD278), NKG2C, and B7-H3 (CD276), or a variant thereof, or an intracellular domain derived from a killer immunoglobulin-like receptor (KIR); and/or (c) comprises a costimulatory domain of 4-1BB; and/or (d) comprises a costimulatory domain of DAP12; and/or (e) comprises a costimulatory domain of CD28; and/or (f) comprises a costimulatory domain of 4-1BB and a costimulatory domain of CD28; and/or (g) comprises a costimulatory domain of DAP12 and a costimulatory domain of CD28; and/or (h) comprises an intracellular domain selected from the group consisting of cytoplasmic signaling domains of a human CD3 zeta chain (CD3ζ), FcγRIII, FcεRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof; and/or (i) the intracellular signaling domain comprises an intracellular domain of CD3ζ.

In another aspect, the invention provides a chimeric antigen receptor (CAR) capable of binding Fibroblast Activation Protein (FAP), comprising an amino acid sequence at least 80%, 85%, 90%, 95%, 96%, 97%, 98%, 99%, or 100% identical to SEQ ID NO: 23 or 25.

In another aspect, the invention provides a nucleic acid comprising a polynucleotide sequence encoding a chimeric antigen receptor (CAR) capable of binding FAP, comprising an antigen-binding domain, a transmembrane domain, and an intracellular domain. The antigen-binding domain comprises: a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), LCDR2 comprises the amino acid sequence LTSNLA (SEQ ID NO: 5), and LCDR3 comprises the amino acid sequence QQWSGYPPIT (SEQ ID NO: 6).

In certain embodiments, the antigen-binding domain: (a) comprises a heavy chain variable region encoded by a polynucleotide sequence at least 80%, 85%, 90%, 95%, 96%, 97%, 98%, 99%, or 100% identical to SEQ ID NO: 8; and/or (b) comprises a light chain variable region encoded by a polynucleotide sequence at least 80%, 85%, 90%, 95%, 96%, 97%, 98%, 99%, or 100% identical to SEQ ID NO: 10; and/or (c) comprises a heavy chain variable region encoded by a polynucleotide sequence at least 80%, 85%, 90%, 95%, 96%, 97%, 98%, 99%, or 100% identical to SEQ ID NO: 8; and a light chain variable region encoded by a polynucleotide sequence at least 80%, 85%, 90%, 95%, 96%, 97%, 98%, 99%, or 100% identical to SEQ ID NO: 10; and/or (d) comprises a single-chain variable fragment (scFv) encoded by a polynucleotide sequence at least 80%, 85%, 90%, 95%, 96%, 97%, 98%, 99%, or 100% identical to SEQ ID NO: 12 or 14.

In certain embodiments, (a) the transmembrane domain comprises a transmembrane domain of CD8 alpha; and/or (b) the intracellular domain comprises a costimulatory signaling domain and an intracellular signaling domain; and/or (c) the intracellular domain comprises a costimulatory signaling domain comprising a costimulatory domain of 4-1BB; and/or (d) the intracellular domain comprises a costimulatory domain of DAP12; and/or (e) the intracellular domain comprises a costimulatory domain of CD28; and/or (f) the intracellular domain comprises a costimulatory domain of 4-1BB and a costimulatory domain of CD28; and/or (g) the intracellular domain comprises a costimulatory domain of DAP12 and a costimulatory domain of CD28; and/or (h) the intracellular signaling domain comprises an intracellular domain of CD3ζ.

In another aspect, the invention provides a nucleic acid comprising a polynucleotide sequence at least 80%, 85%, 90%, 95%, 96%, 97%, 98%, 99%, or 100% identical to SEQ ID NO: 22 or 24.

In another aspect, the invention provides a vector comprising any of the nucleic acids contemplated herein. In certain embodiments, the vector is an expression vector and/or the vector is selected from the group consisting of a DNA vector, an RNA vector, a plasmid, a lentiviral vector, an adenoviral vector, an adeno-associated viral vector, and a retroviral vector.

In another aspect, the invention provides a modified immune cell or precursor cell thereof, comprising any of the nucleic acids contemplated herein.

In another aspect, the invention provides a modified immune cell or precursor cell thereof, comprising a chimeric antigen receptor (CAR) capable of binding fibroblast activation protein (FAP), wherein the CAR comprises: a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), a LCDR2 comprises the amino acid sequence LTSNLA (SEQ ID NO: 5), and LCDR3 comprises the amino acid sequence QQWSGYPPIT (SEQ ID NO: 6).

In certain embodiments, the CAR comprises: (a) a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9; and/or (b) a single-chain variable fragment (scFv) comprising an amino acid sequence at least 80%, 85%, 90%, 95%, 96%, 97%, 98%, 99%, or 100% identical to SEQ ID NO: 11 or 13; and/or (c) an amino acid sequence at least 80%, 85%, 90%, 95%, 96%, 97%, 98%, 99%, or 100% identical to SEQ ID NO: 23 or 25.

In certain embodiments, the CAR: (a) is capable of binding FAP; and/or (b) is capable of binding human FAP; and/or (c) is capable of binding canine FAP; and/or (d) is capable of binding mouse FAP; and/or (e) is capable of binding human, canine, and mouse FAP.

In certain embodiments, the modified cell: (a) is a modified T cell; and/or (b) is a modified NK cell; and/or (c) is an autologous cell; and/or (d) is an autologous cell obtained from a human subject; and/or (e) is an autologous cell obtained from a canine subject; and/or (f) is an allogeneic cell.

In another aspect, the invention provides a pharmaceutical composition comprising a therapeutically effective amount of any of the modified cells contemplated herein, and a pharmaceutically acceptable excipient.

In another aspect, the invention provides a method of treating a disease in a subject in need thereof, comprising administering to the subject an effective amount of any of the modified cells contemplated herein.

In certain embodiments, (a) the disease is selected from the group consisting of an immunological disease, a hematological disease, an autoimmune disease, fibrosis, and cancer; and/or (b) the disease is cancer; and/or (c) the disease is cardiac fibrosis; and/or (d) the disease is cancer, and the cancer comprises a FAP-expressing cancer-associated cell.

In certain embodiments, (a) the FAP-expressing cancer-associated cell is a cancer-associated fibroblast (CAF); and/or (b) the FAP-expressing cancer-associated cell is a FAP-expressing adipocyte; and/or (c) the FAP-expressing cancer-associated cell is a tumor-associated macrophage (TAM); and/or (d) the FAP-expressing cancer-associated cell is a tumor-associated neutrophil (TAN); and/or (e) the FAP-expressing cancer-associated cell is a myeloid-derived suppressor cell (MDSC); and/or (f) the FAP-expressing cancer-associated cell is a cancer-initiating cell.

In another aspect, the invention provides a method of treating a cancer in a subject in need thereof, comprising administering to the subject an effective amount of a modified immune cell comprising a chimeric antigen receptor (CAR) capable of binding FAP, wherein the CAR comprises: a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9; wherein the cancer comprises fibroblast activation protein (FAP)-expressing cancer-associated cells, and wherein the CAR binds to FAP-expressing cancer-associated cells and does not bind to cells that do not express FAP.

In another aspect, the invention provides a method of treating a cancer in a subject in need thereof, wherein (a) the cancer is associated with fibroblast activation protein (FAP)-expressing cancer-associated fibroblasts; and/or (b) the cancer is associated with fibroblast activation protein (FAP)-expressing cancer-associated macrophages; and/or (c) the cancer is associated with fibroblast activation protein (FAP)-expressing cancer-associated neutrophils. The method comprises administering to the subject an effective amount of a modified T cell comprising a chimeric antigen receptor (CAR) capable of binding FAP, wherein the CAR comprises a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

In another aspect, the invention provides a method of treating a cancer in a subject in need thereof, wherein (a) the cancer is associated with fibroblast activation protein (FAP)-expressing cancer-associated fibroblasts; and/or (b) the cancer is associated with fibroblast activation protein (FAP)-expressing cancer-associated macrophages; and/or (c) the cancer is associated with fibroblast activation protein (FAP)-expressing cancer-associated neutrophils. The method comprises administering to the subject an effective amount of a modified T cell comprising a chimeric antigen receptor (CAR) capable of binding FAP, wherein the CAR comprises an amino acid sequence at least 80%, 85%, 90%, 95%, 96%, 97%, 98%, 99%, or 100% identical to SEQ ID NO: 23 or 25.

In another aspect, the invention provides a method of treating a solid tumor in a subject in need thereof, wherein (a) the tumor is associated with fibroblast activation protein (FAP)-expressing cancer-associated fibroblasts; and/or (b) the tumor is associated with fibroblast activation protein (FAP)-expressing cancer-associated macrophages; and/or (c) the tumor is associated with fibroblast activation protein (FAP)-expressing cancer-associated neutrophils. The method comprises administering to the subject an effective amount of a modified T cell comprising a chimeric antigen receptor (CAR) capable of binding FAP, wherein the CAR comprises a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

In certain embodiments, the method further comprises administering an immune checkpoint inhibitor, tumor antigen vaccine, or neoplastic cell targeted therapies.

In certain embodiments, the subject is a human or a non-human animal.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1 shows sequence alignments between the amino acid sequence (SEQ ID NO; 56; Top) of a canine FAP encoded by the gene sequence listed in the NCBI database (XM_005640252.2) and the amino acid sequence of a FAP encoded by the product of the PCR amplification of the canine FAP gene (SEQ ID NO: 26) using two primers that were created using the NCBI sequence. At the nucleotide level, the PCR gene product (SEQ ID NO: 26) possessed two mutations conservative base-pair substitutions at positions 381 (a to t) and 1809 (t to c) of SEQ ID NO: 26 (boxed residues in inset sequences, right). The top right inset discloses a sequence alignment between nucleotides 361-390 of SEQ ID NO: 26 (SEQ ID NO: 58) and SEQ ID NO: 57 (nucleotides 676 to 705 of XM_005640252.2). Bottom right inset discloses a sequence alignment between nucleotides 1801-1828 of SEQ ID NO: 26 (SEQ ID NO: 60) and SEQ ID NO: 59 (nucleotides 2116 to 2143 of XM_005640252.2). The mutations are conservative base-pair substitutions that do not affect the respective encoded threonine at position 127 (T127) or alanine at position 603 (A603) (boxed residues, left; inset sequences, right).

FIGS. 4A-4B are a sequence map illustrating the sequences and features of the HG2L version of the 4G5 canine FAP CD8H BB CD3Z CAR construct (SEQ ID NO: 22 & SEQ ID NO: 23).

FIGS. 5A-5B are a sequence map illustrating the sequence and features of the L2HG version of the 4G5 canine FAP CD8H BB CD3Z CAR construct (SEQ ID NO: 24 & SEQ ID NO: 25).

FIGS. 6A-6D are a series of graphs showing in vitro function of 4G5-based CAR T cells during co-culture cytotoxicity assays using cell lines expressing mouse and canine FAP protein as targets. The murine 3T3 cell was stained with the anti-mouse FAP 73.3 antibody to verify expression of FAP as compared to negative control stains with anti-human FAP F19 and a mouse IgG isotype control (FIG. 6A). Assays measuring cytotoxicity and activation used target cell killing, as measured by luminescence (FIG. 6B), and IFNγ production as measured by ELISA (FIG. 6C). Recognition of canine FAP was assessed by a similar co-culture study using MC KOSA cells as targets measuring IFNγ production (FIG. 6D).

FIGS. 9A-9C are a series of graphs demonstrating the cytotoxic function of anti-FAP CAR expressing T cells in in vitro assays using FAP-low expressing HOS cells as targets. Flow cytometry of FAP expression verified the low surface expression of FAP protein by these cells (FIG. 9A). These target cells were subsequently used in in vitro co-culture cytotoxic function assays with various anti-FAP CAR T cells or non-transduced control T cells (NTD). Cytotoxicity of labeled target cells was assessed by luminescence (FIG. 9B) and production of IFNγ by T cells was assessed by ELISA of supernatant (FIG. 9C) after 24 hours of co-culture. Error bars indicate standard deviation between replicate samples in each experimental group at each effector to target ratio. *p≤0.05 for F19 CAR T cells vs. HL and LH 4G5-based CAR T cells at the 20:1 effector to target ratio. "NS" indicates no statistical difference between HL and LH CAR T cells at the same effector to target ratio.

DETAILED DESCRIPTION

Figure 2:
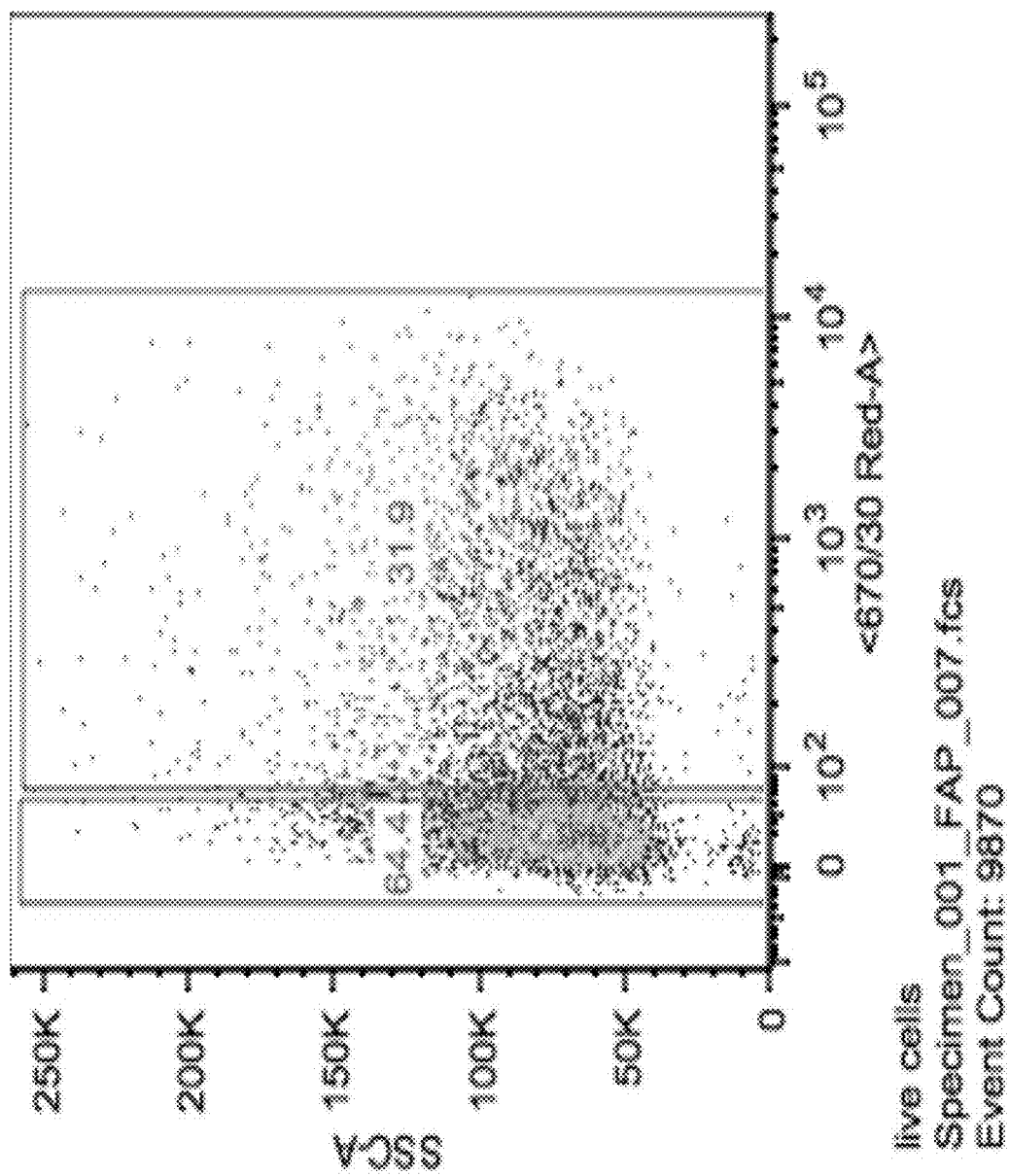
FIG. 2 is a flow cytometry plot demonstrating expression of the recombinant canine FAP construct after transduction into BALB/c 3T3 cells.

The present invention provides compositions and methods for modified immune cells or precursors thereof (e.g., modified T cells) comprising a chimeric antigen receptor (CAR) capable of binding human fibroblast activation protein (FAP). The provided compositions and methods are useful for treating an immunological disease, a hematological disease, an autoimmune disease, fibrosis (e.g. cardiac fibrosis), and/or cancer.

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2nd edition).

A. Definitions

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

As used herein, the terms "about" or "approximately," when preceding a numerical value, indicates the value plus or minus a range of 10% of the value.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. Antibodies also include dimers that may be naturally occurring or constructed from single chain antibodies or antibody fragments. The antibodies in the present invention may exist in a variety of forms including, for example, polyclonal antibodies, monoclonal antibodies, Fv, Fab and F(ab')$_2$, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')$_2$, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments. The antibody fragment also includes a human antibody or a humanized antibody or a portion of a human antibody or a humanized antibody.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample.

Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to which it is later to be re-introduced into the individual.

"Allogeneic" refers to a graft derived from a different animal of the same species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In certain embodiments, the cancer is medullary thyroid carcinoma.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for the ability to bind FAP using the functional assays described herein.

"Co-stimulatory ligand", as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

The term "downregulation" as used herein refers to the decrease or elimination of gene expression of one or more genes.

The term "dysregulated" when used in the context of the level of expression or activity of FAP refers to the level of expression or activity that is different from the expression level or activity of FAP in an otherwise identical healthy animal, organism, tissue, cell or component thereof. The term "dysregulated" also refers to the altered regulation of the level of expression and activity of FAP compared to the regulation in an otherwise identical healthy animal, organism, tissue, cell or component thereof.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. Preferably, the epitope is about 4-18 amino acids, more preferably about 5-16 amino acids, and even more most preferably 6-14 amino acids, more preferably about 7-12, and most preferably about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide used in the present invention can be an epitope.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" and "chimeric" forms of non-human (e.g., murine) antibodies are immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized and chimeric antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized and chimeric antibodies can comprise residues which are found neither in the recipient antibody nor in the imported CDR or framework sequences. These modifications are made to further refine and optimize antibody performance. In general, the humanized and chimeric antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized and chimeric antibody optimally also will comprise at least a portion of an immunoglobulin constant region (Fc), typically that of a human immunoglobulin. The World Health Organization (WHO) International Nonproprietary Name (INN) Expert Group has defined requirements for non-human derived antibodies to be considered "humanized". According to guidelines, comparison of a candidate antibody to human sequences should be done through the International Immunogenetics Information System® (IMGT®) DomainGapAlign tool (www.imgt.org). This tool interrogates the IMGT® database of antibody germline variable region genes where the alignment score is made only against germline sequence variable region exons, thus omitting part of CDR3 and the J region from the analysis. For an antibody to be "humanized", in addition to being "closer to human than to other species", the top "hit" should be human and the identity to human sequences must be at least 85%, otherwise the antibody would be designated as "chimeric". For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immune response" as used herein is defined as a cellular response to an antigen that occurs when lymphocytes identify antigenic molecules as foreign and induce the formation of antibodies and/or activate lymphocytes to remove the antigen.

The term "immunosuppressive" is used herein to refer to reducing overall immune response.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine. Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

The term "oligonucleotide" typically refers to short polynucleotides. It will be understood that when a nucleotide sequence is represented by a DNA sequence (i.e., A, T, C, G), this also includes an RNA sequence (i.e., A, U, C, G) in which "U" replaces "T."

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell. An example of a "cell surface receptor" is human FAP.

"Single chain antibodies" refer to antibodies formed by recombinant DNA techniques in which immunoglobulin heavy and light chain fragments are linked to each other using an engineered span of amino acids to recapitulate the Fv region of an antibody as a single polypeptide. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334:54454; Skerra et al. (1988) Science 242:1038-1041.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a nucleic acid sequence that defines a portion of a nucleic acid to which a binding molecule may specifically bind under conditions sufficient for binding to occur. In some embodiments, a target sequence refers to a genomic nucleic acid sequence that defines a portion of a nucleic acid to which a binding molecule may specifically bind under conditions sufficient for binding to occur.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

"Xenogeneic" refers to a graft derived from an animal of a different species.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

B. Chimeric Antigen Receptors

The present invention provides a therapeutic agent (e.g., a chimeric antigen receptor) for use in the treatment of solid tumors. The successful treatment of solid tumors has been hampered by various obstacles, including, e.g., the tumor microenvironment. Tumors comprise cancer cells as well as a stromal compartment comprising cellular and non-cellular components. The tumor stroma has been shown to have critical roles in the development of cancer, including progression and metastasis. The present invention provides a CAR for targeting tumor stroma, where potential cellular targets in the stroma include cancer-associated fibroblasts (CAFs). CAFs have been shown to enhance almost every aspect of tumor growth and spread. CAFs present a barrier to therapeutic agents (e.g., drugs and immune cells), provide growth signals to tumor cells, and are actively immunosuppressive.

The present invention provides chimeric antigen receptors (CARs) capable of binding Fibroblast Activation Protein (FAP). FAP is a type II transmembrane serine protease that is expressed in the stroma of over 90% of common human epithelial cancers. In certain tumors, it is selectively expressed by cancer-associated fibroblasts. Expression of FAP has not been detected in benign tumors or normal adult quiescent tissues.

In certain embodiments, a subject CAR comprises an antigen-binding domain capable of binding FAP, a transmembrane domain, and an intracellular domain. Also provided are compositions and methods for modified immune cells or precursors thereof, e.g., modified T cells, comprising the CAR. Thus, in some embodiments, the immune cell has been genetically modified to express the CAR. Nucleic acids encoding said CARs, vectors encoding said nucleic acids, and modified cells (e.g. modified T cells) comprising said CARs, vectors, or nucleic acids, are also provided.

In certain embodiments, the CAR is capable of binding human FAP. In certain embodiments, the CAR is capable of binding canine FAP. In certain embodiments, the CAR is capable of binding murine FAP. In certain embodiments, the CAR is capable of binding human, canine, and murine FAP. In such embodiments, the antigen-binding domain may be referred to as cross-species reactive. Cross-species reactive antigen-binding domains are useful in translatable research where the human-targeting antigen-binding domain also binds the same antigen in a different species (e.g., a model organism), allowing for testing of the same antigen-binding domain in a disease model.

A subject CAR of the invention comprises an antigen-binding domain capable of binding FAP, a transmembrane domain, and an intracellular domain. A subject CAR of the invention may optionally comprise a hinge domain. Accordingly, a subject CAR of the invention comprises an antigen-binding domain capable of binding FAP, a hinge domain, a transmembrane domain, and an intracellular domain.

The antigen-binding domain may be operably linked to another domain of the CAR, such as the transmembrane domain or the intracellular domain, both described elsewhere herein, for expression in the cell. In one embodiment, a first nucleic acid sequence encoding the antigen-binding domain is operably linked to a second nucleic acid encoding a transmembrane domain, and further operably linked to a third a nucleic acid sequence encoding an intracellular domain.

The antigen-binding domains described herein can be combined with any of the transmembrane domains described herein, any of the intracellular domains or cytoplasmic domains described herein, or any of the other domains described herein that may be included in a CAR of the present invention. A subject CAR of the present invention may also include a hinge domain as described herein. A subject CAR of the present invention may also include a spacer domain as described herein. In some embodiments, each of the antigen-binding domain, transmembrane domain, and intracellular domain is separated by a linker.

Antigen Binding Domain

The antigen-binding domain of a CAR is an extracellular region of the CAR for binding to a specific target antigen including proteins, carbohydrates, and glycolipids. A subject CAR of the invention comprises an antigen-binding domain that is capable of Fibroblast Activation Protein (FAP).

The antigen-binding domain can include any domain that binds to the antigen and may include, but is not limited to, a monoclonal antibody, a polyclonal antibody, a synthetic antibody, a human antibody, a humanized antibody, a non-human antibody, and any fragment thereof. In some embodiments, the antigen-binding domain portion comprises a mammalian antibody or a fragment thereof. The choice of antigen-binding domain may depend upon the type and number of antigens that are present on the surface of a target cell.

In some embodiments, the antigen-binding domain is selected from the group consisting of a full-length antibody, an antigen-binding fragment, a Fab, a single-chain variable fragment (scFv), or a single-domain antibody. In some embodiments, a FAP binding domain of the present invention is selected from the group consisting of a FAP-specific antibody, a FAP-specific Fab, and a FAP-specific scFv. In one embodiment, a FAP binding domain is a FAP-specific antibody. In one embodiment, a FAP binding domain is a FAP-specific Fab. In one embodiment, a FAP binding domain is a FAP-specific scFv.

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker, which connects the N-terminus of the VH with the C-terminus of the VL, or the C-terminus of the VH with the N-terminus of the VL. In some embodiments, the antigen-binding domain (e.g., FAP binding domain) comprises an scFv having the configuration from N-terminus to C-terminus, VH-linker-VL. In some embodiments, the antigen-binding domain comprises an scFv having the configuration from N-terminus to C-terminus, VL-linker-VH. Those of skill in the art would be able to select the appropriate configuration for use in the present invention.

The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/

087010, the contents of which are hereby incorporated by reference in their entireties. Various linker sequences are known in the art, including, without limitation, glycine serine (GS) linkers such as (GS)$_n$, (GSGGS)$_n$ (SEQ ID NO:31), (GGGS)$_n$ (SEQ ID NO:32), and (GGGGS)$_n$ (SEQ ID NO:33), where n represents an integer of at least 1. Exemplary linker sequences can comprise amino acid sequences including, without limitation, GGSG (SEQ ID NO:34), GGSGG (SEQ ID NO:35), GSGSG (SEQ ID NO:36), GSGGG (SEQ ID NO:37), GGGSG (SEQ ID NO:38), GSSSG (SEQ ID NO:39), GGGGS (SEQ ID NO:40), GGGGSGGGGSGGGGS (SEQ ID NO:15) and the like. Those of skill in the art would be able to select the appropriate linker sequence for use in the present invention. In one embodiment, an antigen-binding domain of the present invention comprises a heavy chain variable region (VH) and a light chain variable region (VL), wherein the VH and VL is separated by the linker sequence having the amino acid sequence GGGGSGGGGSGGGGS (SEQ ID NO:15), which may be encoded by the nucleic acid sequence GGTGGCGGTGGCTCGGGCGGTGGTGGGTCGGGT-GGCGGCGGATCT (SEQ ID NO:41).

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Biol Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "Fab" refers to a fragment of an antibody structure that binds to an antigen but is monovalent and does not have a Fc portion, for example, an antibody digested by the enzyme papain yields two Fab fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen-binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

In some embodiments, the antigen-binding domain may be derived from the same species in which the CAR will ultimately be used. For example, for use in humans, the antigen-binding domain of the CAR may comprise a human antibody or a fragment thereof. In some embodiments, the antigen-binding domain may be derived from a different species in which the CAR will ultimately be used. For example, for use in humans, the antigen-binding domain of the CAR may comprise a murine antibody, or a canine antibody, or a fragment thereof.

In certain embodiments, the antigen-binding domain comprises a heavy chain variable region that comprises three heavy chain complementarity determining regions (HCDRs). In certain embodiments, HCDR1 comprises the amino acid sequence YTITSYSLH (SEQ ID NO: 1), and/or HCDR2 comprises the amino acid sequence EIN-PANGDHNFSEKFEIK (SEQ ID NO: 2), and/or HCDR3 comprises the amino acid sequence LDDSRFHWYFDV (SEQ ID NO: 3). The antigen-binding domain also comprises a light chain variable region that comprises three light chain complementarity determining regions (LCDRs). In certain embodiments, LCDR1 comprises the amino acid sequence TASSSVSYMY (SEQ ID NO: 4), and/or LCDR2 comprises the amino acid sequence LTSNLA (SEQ ID NO: 5), and/or LCDR3 comprises the amino acid sequence QQWSGYPPIT (SEQ ID NO: 6).

In certain embodiments, the antigen-binding domain comprises a heavy chain variable region that comprises three heavy chain complementarity determining regions (HCDRs), wherein HCDR1 comprises the amino acid sequence GYTITSYSLH (SEQ ID NO: 27), and/or HCDR2 comprises the amino acid sequence EINPANGDHNFSEK-FEIK (SEQ ID NO: 2), and/or HCDR3 comprises the amino acid sequence LDDSRFHWYFDV (SEQ ID NO: 3). In certain embodiments, the antigen-binding domain also comprises a light chain variable region that comprises three light chain complementarity determining regions (LCDRs), wherein LCDR1 comprises the amino acid sequence TASSSVSYMY (SEQ ID NO: 4), and/or LCDR2 comprises the amino acid sequence LTSNLAS (SEQ ID NO: 30), and/or LCDR3 comprises the amino acid sequence QQWSGYPPIT (SEQ ID NO: 6).

In certain embodiments, the antigen-binding domain comprises a heavy chain variable region that comprises three heavy chain complementarity determining regions (HCDRs), wherein HCDR1 comprises the amino acid sequence YTITSYSLH (SEQ ID NO: 1), and/or HCDR2 comprises the amino acid sequence EINPANGDHNFSEK-FEIKAT (SEQ ID NO: 28), and/or HCDR3 comprises the amino acid sequence TRLDDSRFHWYFDV (SEQ ID NO: 29). In certain embodiments, the antigen-binding domain also comprises a light chain variable region that comprises three light chain complementarity determining regions (LCDRs), wherein LCDR1 comprises the amino acid sequence TASSSVSYMY (SEQ ID NO: 4), and/or LCDR2 comprises the amino acid sequence LTSNLA (SEQ ID NO: 5), and/or LCDR3 comprises the amino acid sequence QQWSGYPPIT (SEQ ID NO: 6).

In certain embodiments, the antigen-binding domain comprises a heavy chain variable region that comprises any of the three heavy chain complementarity determining regions, HCDR1, HCDR2, and HCDR3, as described herein. In certain embodiments, the antigen-binding domain comprises a light chain variable region that comprises any of the three light chain complementarity determining regions, LCDR1, LCDR2, and LCDR3, as described herein. In certain embodiments, the antigen-binding domain comprises any combination of HCDR1, HCDR2, HCDR3, LCDR1, LCDR2, and LCDR3, and described herein. The skilled artisan would readily be able to determine the relevant complementarity determining regions based on amino acid numbering in view of the heavy and light chain variable region sequences provided herein.

In certain embodiments, the heavy chain variable region (VH) of the antigen-binding domain comprises an amino acid sequence at least 80%, 85%, 90%, 95%, 96%, 97%, 98%, 99%, or 100% identical to SEQ ID NO: 7 and/or the light chain variable region (VH) comprises an amino acid sequence at least 80%, 85%, 90%, 95%, 96%, 97%, 98%, 99%, or 100% identical to SEQ ID NO: 9.

In certain embodiments, the antigen-binding domain is selected from the group consisting of a full length antibody or antigen-binding fragment thereof, a Fab, a single-chain variable fragment (scFv), or a single-domain antibody. In certain embodiments, the antigen-binding domain is a single-chain variable fragment (scFv) comprising an amino acid sequence at least 80%, 85%, 90%, 95%, 96%, 97%, 98%, 99%, or 100% identical to SEQ ID NO: 11 or SEQ ID NO: 13.

Tolerable variations of the antigen-binding domain sequences will be known to those of skill in the art. For example, in some embodiments the antigen-binding domain comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NO: 1, 2, 3, 4, 5, 6, 7, 9, 11, 13, 27, 28, 29, or 30.

In some embodiments, a CAR of the present disclosure may have affinity for one or more target antigens on one or more target cells. In some embodiments, a CAR may have affinity for one or more target antigens on a target cell. In such embodiments, the CAR is a bispecific CAR, or a multispecific CAR. In some embodiments, the CAR comprises one or more target-specific binding domains that confer affinity for one or more target antigens. In some embodiments, the CAR comprises one or more target-specific binding domains that confer affinity for the same target antigen. For example, a CAR comprising one or more target-specific binding domains having affinity for the same target antigen could bind distinct epitopes of the target antigen. When a plurality of target-specific binding domains is present in a CAR, the binding domains may be arranged in tandem and may be separated by linker peptides. For example, in a CAR comprising two target-specific binding domains, the binding domains are connected to each other covalently on a single polypeptide chain, through an oligo- or polypeptide linker, an Fc hinge region, or a membrane hinge region.

Transmembrane Domain

CARs of the present invention may comprise a transmembrane domain that connects the antigen-binding domain of the CAR to the intracellular domain of the CAR. The transmembrane domain of a subject CAR is a region that is capable of spanning the plasma membrane of a cell (e.g., an immune cell or precursor thereof). In some embodiments, the transmembrane domain is for insertion into a cell membrane, e.g., a eukaryotic cell membrane. In some embodiments, the transmembrane domain is interposed between the antigen-binding domain and the intracellular domain of a CAR.

In some embodiments, the transmembrane domain is naturally associated with one or more of the domains in the CAR. In some embodiments, the transmembrane domain can be selected or modified by one or more amino acid substitutions to avoid binding of such domains to the transmembrane domains of the same or different surface membrane proteins, to minimize interactions with other members of the receptor complex.

The transmembrane domain may be derived either from a natural or a synthetic source. Where the source is natural, the domain may be derived from any membrane-bound or transmembrane protein, e.g., a Type I transmembrane protein. Where the source is synthetic, the transmembrane domain may be any artificial sequence that facilitates insertion of the CAR into a cell membrane, e.g., an artificial hydrophobic sequence. Examples of the transmembrane domain of particular use in this invention include, without limitation, transmembrane domains derived from (i.e. comprise at least the transmembrane region(s) of) the alpha, beta or zeta chain of the T cell receptor, CD28, CD3 epsilon, CD45, CD4, CD5, CD7, CD8, CD9, CD16, CD22, CD33, CD37, CD64, CD80, CD86, CD134 (OX-40), CD137 (4-1BB), CD154 (CD40L), ICOS (CD278), Toll-like receptor 1 (TLR1), TLR2, TLR3, TLR4, TLR5, TLR6, TLR7, TLR8, TLR9, or a transmembrane domain derived from a killer immunoglobulin-like receptor (KIR).

In certain embodiments, the transmembrane domain comprises a transmembrane domain of CD8. In certain embodiments, the transmembrane domain of CD8 is a transmembrane domain of CD8 alpha. In certain embodiments, the transmembrane domain comprises the amino acid sequence set forth in SEQ ID NO: 17. In certain embodiments, the transmembrane domain comprises a transmembrane domain derived from a killer immunoglobulin-like receptor (KIR).

In some embodiments, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

The transmembrane domains described herein can be combined with any of the antigen-binding domains described herein, any of the intracellular domains described herein, or any of the other domains described herein that may be included in a subject CAR.

In some embodiments, the transmembrane domain further comprises a hinge region. A subject CAR of the present invention may also include a hinge region. The hinge region of the CAR is a hydrophilic region which is located between the antigen-binding domain and the transmembrane domain. In some embodiments, this domain facilitates proper protein folding for the CAR. The hinge region is an optional component for the CAR. The hinge region may include a domain selected from Fc fragments of antibodies, hinge regions of antibodies, CH2 regions of antibodies, CH3 regions of antibodies, artificial hinge sequences or combinations thereof. Examples of hinge regions include, without limitation, a CD8a hinge, artificial hinges made of polypeptides which may be as small as, three glycines (Gly), as well as CH1 and CH3 domains of IgGs (such as human IgG4).

In some embodiments, a subject CAR of the present disclosure includes a hinge region that connects the antigen-binding domain with the transmembrane domain, which, in turn, connects to the intracellular domain. The hinge region is preferably capable of supporting the antigen-binding domain to recognize and bind to the target antigen on the target cells (see, e.g., Hudecek et al., *Cancer Immunol. Res.* (2015) 3(2): 125-135). In some embodiments, the hinge region is a flexible domain, thus allowing the antigen-binding domain to have a structure to optimally recognize the specific structure and density of the target antigens on a cell such as tumor cell (Hudecek et al., supra). The flexibility of the hinge region permits the hinge region to adopt many different conformations.

In some embodiments, the hinge region is an immunoglobulin heavy chain hinge region. In some embodiments, the hinge region is a hinge region polypeptide derived from a receptor (e.g., a CD8-derived hinge region).

The hinge region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa. In some embodiments, the hinge region can have a length of greater than 5 aa, greater than 10 aa, greater than 15 aa, greater than 20 aa, greater than 25 aa, greater than 30 aa, greater than 35 aa, greater than 40 aa, greater than 45 aa, greater than 50 aa, greater than 55 aa, or more.

Suitable hinge regions can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids. Suitable hinge regions can have a length of greater than 20 amino acids (e.g., 30, 40, 50, 60 or more amino acids).

For example, hinge regions include glycine polymers $(G)_n$, glycine-serine polymers (including, for example, $(GS)_n$, $(GSGGS)_n$ (SEQ ID NO:31) and $(GGGS)_n$ (SEQ ID NO:32), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see, e.g., Scheraga, *Rev. Computational. Chem.* (1992) 2: 73-142). Exemplary hinge regions can comprise amino acid sequences including, but not limited to, GGSG (SEQ ID NO:34), GGSGG (SEQ ID NO:35), GSGSG (SEQ ID NO:36), GSGGG (SEQ ID NO:37), GGGSG (SEQ ID NO:38), GSSSG (SEQ ID NO:39), and the like.

In some embodiments, the hinge region is an immunoglobulin heavy chain hinge region. Immunoglobulin hinge region amino acid sequences are known in the art; see, e.g., Tan et al., *Proc. Natl. Acad. Sci. USA* (1990) 87(1):162-166; and Huck et al., *Nucleic Acids Res.* (1986) 14(4): 1779-1789. As non-limiting examples, an immunoglobulin hinge region can include one of the following amino acid sequences: DKTHT (SEQ ID NO:42); CPPC (SEQ ID NO:43); CPEPKSCDTPPPCPR (SEQ ID NO:44) (see, e.g., Glaser et al., *J. Biol. Chem.* (2005) 280:41494-41503); ELKTPLGDTTHT (SEQ ID NO:45); KSCDKTHTCP (SEQ ID NO:46); KCCVDCP (SEQ ID NO:47); KYGPPCP (SEQ ID NO:48); EPKSCDKTHTCPPCP (SEQ ID NO:49) (human IgG1 hinge); ERKCCVECPPCP (SEQ ID NO:50) (human IgG2 hinge); ELKTPLGDTTHTCPRCP (SEQ ID NO:51) (human IgG3 hinge); SPNMVPHAHHAQ (SEQ ID NO:52) (human IgG4 hinge); and the like.

The hinge region can comprise an amino acid sequence of a human IgG1, IgG2, IgG3, or IgG4, hinge region. In one embodiment, the hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO:53); see, e.g., Yan et al., *J. Biol. Chem.* (2012) 287: 5891-5897.

In certain embodiments, the hinge region can comprise an amino acid sequence derived from human CD8, or a variant thereof. In certain embodiments, the CAR comprises a CD8 alpha hinge sequence. In certain embodiments, the hinge region comprises the amino acid sequence TTTPAPRPPT-PAPTIASQPLSLRPEACRPAAGGAVHTRGLDFACD (SEQ ID NO: 16).

Intracellular Domain

A subject CAR of the present invention also includes an intracellular domain. In certain embodiments, the intracellular domain comprises a costimulatory signaling domain and an intracellular signaling domain. The intracellular domain of the CAR is responsible for activation of at least one of the effector functions of the cell in which the CAR is expressed (e.g., immune cell). The intracellular domain transduces the effector function signal and directs the cell (e.g., immune cell) to perform its specialized function, e.g., harming and/or destroying a target cell.

Examples of an intracellular domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular domain include, without limitation, the ζ chain of the T cell receptor complex or any of its homologs, e.g., η chain, FcsRIγ and β chains, MB 1 (Iga) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In one embodiment, the intracellular signaling domain may be human CD3 zeta chain, FcγRIII, FcsRI, cytoplasmic tails of Fc receptors, an immunoreceptor tyrosine-based activation motif (ITAM) bearing cytoplasmic receptors, and combinations thereof.

In certain embodiments, the intracellular domain of the CAR includes any portion of one or more co-stimulatory molecules, such as at least one signaling domain from CD2, CD3, CD8, CD27, CD28, ICOS (CD278), 4-1BB, PD-1, any derivative or variant thereof, any synthetic sequence thereof that has the same functional capability, and any combination thereof. In certain embodiments, the intracellular domain comprises a costimulatory domain of a protein selected from the group consisting of: proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS, NKG2C, and B7-H3 (CD276), an intracellular domain derived from a killer immunoglobulin-like receptor (KIR), or a variant thereof.

Further, variant intracellular signaling domains suitable for use in a subject CAR are known in the art. The YMFM motif is found in ICOS and is a SH2 binding motif that recruits both p85 and p50alpha subunits of PI3K, resulting in enhanced AKT signaling. See, e.g., Simpson et al. (2010) Curr. Opin. Immunol., 22:326-332. In one embodiment, a CD28 intracellular domain variant may be generated to comprise a YMFM motif. The YMNM motif is found in the CD28 cytoplasmic domain and is a known binding site for phosphatidylinositol 3-kinase (PI3-K) and Grb2. See, Harada et al. (2003) J. Exp. Med., 197(2):257-262. In one embodiment, an ICOS intracellular domain variant may be generated to comprise a YMNM motif.

In certain embodiments, the intracellular domain comprises a costimulatory domain of 4-1BB. In certain embodiments, the costimulatory domain of 4-1BB comprises the amino acid sequence set forth in SEQ ID NO: 18. In certain embodiments, the intracellular domain comprises a costimulatory domain of CD28. In certain embodiments, the costimulatory domain of CD28 comprises the amino acid sequence set forth in SEQ ID NO: 19. In certain embodiments, the intracellular domain comprises a costimulatory domain of DAP12. In certain embodiments, the costimulatory domain of DAP12 comprises the amino acid sequence set forth in SEQ ID NO: 20. In certain embodiments, the intracellular domain comprises a costimulatory domain of 4-1BB and a costimulatory domain of CD28. In certain embodiments, the intracellular domain comprises a costimulatory domain of DAP12 and a costimulatory domain of CD28.

Other examples of the intracellular domain include a fragment or domain from one or more molecules or receptors including, but not limited to, TCR, CD3 zeta, CD3 gamma, CD3 delta, CD3 epsilon, CD86, common FcR gamma, FcR beta (Fc Epsilon RIb), CD79a, CD79b, Fcgamma RIIa, DAP10, DAP12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CDlib, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

Additional examples of intracellular domains include, without limitation, intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (see, e.g., Park and Brentjens, J. Clin. Oncol. (2015) 33(6): 651-653). Additionally, intracellular signaling domains may include signaling domains used by NK and NKT cells (see, e.g., Hermanson and Kaufman, Front. Immunol. (2015) 6: 195) such as signaling domains of NKp30 (B7-H6) (see, e.g., Zhang et al., J. Immunol. (2012) 189(5): 2290-2299), and DAP 12 (see, e.g., Topfer et al., J. Immunol. (2015) 194(7): 3201-3212), NKG2D, NKp44, NKp46, DAP10, and CD3z.

In certain embodiments, the intracellular domain comprises an intracellular signaling domain selected from the group consisting of cytoplasmic signaling domains of a human CD3 zeta chain (CD3ζ), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In certain embodiments, the intracellular domain comprises an intracellular domain of CD3ζ or a variant thereof. In certain embodiments, the intracellular domain of CD3ζ comprises the amino acid sequence set forth in SEQ ID NO: 21.

Intracellular domains suitable for use in a subject CAR of the present invention include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR (i.e., activated by antigen and dimerizing agent). In some embodiments, the intracellular domain includes at least one (e.g., one, two, three, four, five, six, etc.) ITAM motif as described below. In some embodiments, the intracellular domain includes DAP10/CD28 type signaling chains. In some embodiments, the intracellular domain is not covalently attached to the membrane bound CAR, but is instead diffused in the cytoplasm.

Intracellular domains suitable for use in a subject CAR of the present invention include immunoreceptor tyrosine-based activation motif (ITAM)-containing intracellular signaling polypeptides. In some embodiments, an ITAM motif is repeated twice in an intracellular domain, where the first and second instances of the ITAM motif are separated from one another by 6 to 8 amino acids. In one embodiment, the intracellular domain of a subject CAR comprises 3 ITAM motifs.

In some embodiments, intracellular domains includes the signaling domains of human immunoglobulin receptors that contain immunoreceptor tyrosine based activation motifs (ITAMs) such as, but not limited to, FcgammaRI, FcgammaRIIA, FcgammaRIIC, FcgammaRIIIA, FcRL5 (see, e.g., Gillis et al., Front. Immunol. (2014) 5:254).

A suitable intracellular domain can be an ITAM motif-containing portion that is derived from a polypeptide that contains an ITAM motif. For example, a suitable intracellular domain can be an ITAM motif-containing domain from any ITAM motif-containing protein. Thus, a suitable intracellular domain need not contain the entire sequence of the entire protein from which it is derived. Examples of suitable ITAM motif-containing polypeptides include, but are not limited to: DAP12, FCER1G (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In one embodiment, the intracellular domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In one embodiment, the intracellular domain is derived from FCER1G (also known as FCRG; Fc epsilon receptor I gamma chain; Fc receptor gamma-chain; fc-epsilon RI-gamma; fcRgamma; fceRl gamma; high affinity immunoglobulin epsilon receptor subunit gamma; immunoglobulin E receptor, high affinity, gamma chain; etc.). In one embodiment, the intracellular domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). In one embodiment, the intracellular domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). In one embodiment, the intracellular domain is derived from T-cell surface glycoprotein CD3 gamma chain (also known as CD3G, T-cell receptor T3 gamma chain, CD3-GAMMA, T3G, gamma polypeptide (TiT3 complex), etc.). In one embodiment, the intracellular domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). In one embodiment, the intracellular domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In one embodiment, an intracellular domain suitable for use in an FN3 CAR of the present disclosure includes a DAP10/CD28 type signaling chain. In one embodiment, an intracellular domain suitable for use in an FN3 CAR of the present disclosure includes a ZAP70 polypeptide. In some embodiments, the intracellular domain includes a cytoplasmic signaling domain of TCR zeta, FcR gamma, FcR beta, CD3 gamma, CD3 delta, CD3 epsilon, CD5, CD22, CD79a, CD79b, or CD66d. In one embodiment, the intracellular domain in the CAR includes a cytoplasmic signaling domain of human CD3 zeta.

While usually the entire intracellular domain can be employed, in many cases it is not necessary to use the entire chain. To the extent that a truncated portion of the intracellular domain is used, such truncated portion may be used in place of the intact chain as long as it transduces the effector function signal. The intracellular domain includes any truncated portion of the intracellular domain sufficient to transduce the effector function signal.

The intracellular domains described herein can be combined with any of the antigen-binding domains described herein, any of the transmembrane domains described herein, or any of the other domains described herein that may be included in the CAR.

Tolerable variations of the individual CAR domain sequences (hinge, transmembrane, and intracellular domains) will be known to those of skill in the art. For example, in some embodiments the CAR domain comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NO: 15, 16, 17, 18, 19, 20 or 21.

In one aspect, the invention provides a chimeric antigen receptor (CAR) comprising an antigen-binding domain capable of binding Fibroblast Activation Protein (FAP), a transmembrane domain, and an intracellular domain. The antigen-binding domain comprises:

a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and/or a light chain variable region that comprises three light chain complementarity determining regions (LCDRs), wherein LCDR1 comprises the amino acid sequence TASSSVSYMY (SEQ ID NO: 4), a LCDR2 comprises the amino acid sequence LTSNLA (SEQ ID NO: 5), and LCDR3 comprises the amino acid sequence QQWSGYPPIT (SEQ ID NO: 6).

Also provided is a CAR capable of binding FAP, comprising an antigen-binding domain, a transmembrane domain, and an intracellular domain, wherein the antigen-binding domain comprises a heavy chain variable region comprising an amino acid sequence at least 80%, 85%, 90%, 95%, 96%, 97%, 98%, 99%, or 100% identical to SEQ ID NO: 7; and/or a light chain variable region comprising an amino acid sequence at least 80%, 85%, 90%, 95%, 96%, 97%, 98%, 99%, or 100% identical to SEQ ID NO: 9.

Also provided is a CAR capable of binding FAP, comprising an antigen-binding domain comprising an amino acid sequence at least 80%, 85%, 90%, 95%, 96%, 97%, 98%, 99%, or 100% identical to SEQ ID NO: 11 or 13.

Further provided is a CAR capable of binding FAP comprising an amino acid sequence at least 80%, 85%, 90%, 95%, 96%, 97%, 98%, 99%, or 100% identical to SEQ ID NO: 23 or 25.

TABLE 1

Nucleic acid and amino acid sequences

| SEQ ID NO: | Name | Amino Acid/Nucleotide Sequence |
|---|---|---|
| 1 | 4G5 HCDR1 | YTITSYSLH |
| 2 | 4G5 HCDR2 | EINPANGDHNFSEKFEIK |
| 3 | 4G5 HCDR3 | LDDSRFHWYFDV |
| 4 | 4G5 LCDR1 | TASSSVSYMY |
| 5 | 4G5 LCDR2 | LTSNLA |
| 6 | 4G5 LCDR3 | QQWSGYPPIT |
| 7 | 4G5 VH | QVQLQQPGAELVKPGASVKLSCKASGYTITSYSLHWVKQRPGQGLE WIGEINPANGDHNFSEKFEIKATLTVDSSSNTAFMQLSRLTSEDSAVY YCTRLDDSRFHWYFDVWGAGTTVTSS |
| 8 | 4G5 VH | CAGGTCCAACTGCAGCAGCCTGGGGCTGAACTGGTAAAGCCTGG GGCTTCAGTGAAGTTGTCCTGCAAGGCGTCTGGCTACACCATCAC CAGCTACTCTCTGCACTGGGTGAAGCAGAGGCCTGGACAAGGCCT |

TABLE 1-continued

Nucleic acid and amino acid sequences

| SEQ ID NO: Name | Amino Acid/Nucleotide Sequence |
|---|---|
|  | TGAGTGGATTGGAGAGATTAATCCTGCCAATGGTGATCATAACTT<br>CAGTGAGAAGTTCGAGATCAAGGCCACACTGACTGTAGACAGCT<br>CCTCCAACACAGCATTCATGCAACTCAGCAGGCTGACATCTGAGG<br>ACTCTGCGGTCTATTACTGTACAAGATTGGACGATAGTAGGTTCC<br>ACTGGTACTTCGATGTCTGGGGCGCAGGGACCACGGTCACCGTCT<br>CCTCA |
| 9  4G5 VL | QIVLTQSPALMSASPGEKVTMTCTASSSVSYMYWYQQKPRSSPKPWI<br>FLTSNLASGVPARFSGRGSGTSFSLTISSMEAEDAATYYCQQWSGYP<br>PITFGSGTKLEIK |
| 10 4G5 VL | CAAATTGTTCTCACCCAGTCTCCAGCGCTCATGTCTGCTTCTCCAG<br>GGGAGAAGGTCACCATGACCTGCACTGCCAGCTCAAGTGTTAGTT<br>ACATGTACTGGTACCAGCAGAAGCCACGATCCTCCCCCAAACCCT<br>GGATTTTTCTCACCTCCAACCTGGCTTCTGGAGTCCCTGCTCGCTT<br>CAGTGGCCGTGGGTCTGGGACCTCTTTCTCTCTCACAATCAGCAG<br>CATGGAGGCTGAAGATGCTGCCACTTATTACTGCCAGCAGTGGAG<br>TGGTTACCCACCCATCACATTCGGCTCGGGGACAAAGTTGGAAAT<br>AAAA |
| 11 4G5 scFv<br>(VL > VH) | QIVLTQSPALMSASPGEKVTMTCTASSSVSYMYWYQQKPRSSPKPWI<br>FLTSNLASGVPARFSGRGSGTSFSLTISSMEAEDAATYYCQQWSGYP<br>PITFGSGTKLEIKGGGGSGGGGSGGGGSQVQLQQPGAELVKPGASVK<br>LSCKASGYTITSYSLHWVKQRPGQGLEWIGEINPANGDHNFSEKFEI<br>KATLTVDSSSNTAFMQLSRLTSEDSAVYYCTRLDDSRFHWYFDVWG<br>AGTTVTVSS |
| 12 4G5 scFv<br>(VL > VH) | CAAATTGTTCTCACCCAGTCTCCAGCGCTCATGTCTGCTTCTCCAG<br>GGGAGAAGGTCACCATGACCTGCACTGCCAGCTCAAGTGTTAGTT<br>ACATGTACTGGTACCAGCAGAAGCCACGATCCTCCCCCAAACCCT<br>GGATTTTTCTCACCTCCAACCTGGCTTCTGGAGTCCCTGCTCGCTT<br>CAGTGGCCGTGGGTCTGGGACCTCTTTCTCTCTCACAATCAGCAG<br>CATGGAGGCTGAAGATGCTGCCACTTATTACTGCCAGCAGTGGAG<br>TGGTTACCCACCCATCACATTCGGCTCGGGGACAAAGTTGGAAAT<br>AAAAGGTGGAGGTGGCAGCGGAGGAGGTGGGTCCGGCGGTGGA<br>GGAAGCCAGGTCCAACTGCAGCAGCCTGGGGCTGAACTGGTAAA<br>GCCTGGGGCTTCAGTGAAGTTGTCCTGCAAGGCGTCTGGCTACAC<br>CATCACCAGCTACTCTCTGCACTGGGTGAAGCAGAGGCCTGGACA<br>AGGCCTTGAGTGGATTGGAGAGATTAATCCTGCCAATGGTGATCA<br>TAACTTCAGTGAGAAGTTCGAGATCAAGGCCACACTGACTGTAGA<br>CAGCTCCTCCAACACAGCATTCATGCAACTCAGCAGGCTGACATC<br>TGAGGACTCTGCGGTCTATTACTGTACAAGATTGGACGATAGTAG<br>GTTCCACTGGTACTTCGATGTCTGGGGCGCAGGGACCACGGTCAC<br>CGTCTCCTCA |
| 13 4G5 scFv<br>(VH > VL) | QVQLQQPGAELVKPGASVKLSCKASGYTITSYSLHWVKQRPGQGLE<br>WIGEINPANGDHNFSEKFEIKATLTVDSSSNTAFMQLSRLTSEDSAVY<br>YCTRLDDSRFHWYFDVWGAGTTVTVSSGGGGSGGGGSGGGGSQIV<br>LTQSPALMSASPGEKVTMTCTASSSVSYMYWYQQKPRSSPKPWIFLT<br>SNLASGVPARFSGRGSGTSFSLTISSMEAEDAATYYCQQWSGYPPITF<br>GSGTKLEIK |
| 14 4G5 scFv<br>(VH > VL) | CAGGTCCAACTGCAGCAGCCTGGGGCTGAACTGGTAAAGCCTGG<br>GGCTTCAGTGAAGTTGTCCTGCAAGGCGTCTGGCTACACCATCAC<br>CAGCTACTCTCTGCACTGGGTGAAGCAGAGGCCTGGACAAGGCCT<br>TGAGTGGATTGGAGAGATTAATCCTGCCAATGGTGATCATAACTT<br>CAGTGAGAAGTTCGAGATCAAGGCCACACTGACTGTAGACAGCT<br>CCTCCAACACAGCATTCATGCAACTCAGCAGGCTGACATCTGAGG<br>ACTCTGCGGTCTATTACTGTACAAGATTGGACGATAGTAGGTTCC<br>ACTGGTACTTCGATGTCTGGGGCGCAGGGACCACGGTCACCGTCT<br>CCTCAGGTGGAGGTGGCAGCGGAGGAGGTGGGTCCGGCGGTGGA<br>GGAAGCCAAATTGTTCTCACCCAGTCTCCAGCGCTCATGTCTGCT<br>TCTCCAGGGGAGAAGGTCACCATGACCTGCACTGCCAGCTCAAGT<br>GTTAGTTACATGTACTGGTACCAGCAGAAGCCACGATCCTCCCCC<br>AAACCCTGGATTTTTCTCACCTCCAACCTGGCTTCTGGAGTCCCTG<br>CTCGCTTCAGTGGCCGTGGGTCTGGGACCTCTTTCTCTCTCACAAT<br>CAGCAGCATGGAGGCTGAAGATGCTGCCACTTATTACTGCCAGCA<br>GTGGAGTGGTTACCCACCCATCACATTCGGCTCGGGGACAAAGTT<br>GGAAATAAAA |
| 15 Linker | GGGGSGGGGSGGGGS |

TABLE 1-continued

Nucleic acid and amino acid sequences

| SEQ ID NO: | Name | Amino Acid/Nucleotide Sequence |
|---|---|---|
| 16 | CD8 alpha hinge | TTTPAPRPPTPAPTIASQPLSLRPEACRPAAGGAVHTRGLDFACD |
| 17 | CD8 transmembrane domain | IYIWAPLAGTCGVLLLSLVITLY |
| 18 | 4-1BB ICD | KRGRKKLLYIFKQPFMRPVQTTQEEDGCSCRFPEEEEGGCE |
| 19 | CD28 ICD | RSKRSRLLHSDYMNMTPRRPGPTRKHYQPYAPPRDFAAYRS |
| 20 | DAP12 ICD | ERWCSNKKNAAVIVIDQEPAGNRTVNSEDSDEQDHQEVSYA |
| 21 | CD3 zeta ICD | RVKFSRSADAPAYQQGQNQLYNELNLGRREEYDVLDKRRGRDPEM GGKPRRKNPQEGLYNELQKDKMAEAYSEIGMKGERRRGKGHDGLY QGLSTATKDTYDALHMQALPPR |
| 22 | 4G5_HG2L_CD8 H_BB_CD3Z CAR | ATGGCCCTGCCTGTGACAGCCCTGCTGCTGCCTCTGGCTCTGCTGC TGCATGCCGCTAGACCCGGATCCCAACTGCAGCAGCCTG GGGCTGAACTGGTAAAGCCTGGGGCTTCAGTGAAGTTGTCCTGCA AGGCGTCTGGCTACACCATCACCAGCTACTCTCTGCACTGGGTGA AGCAGAGGCCTGGACAAGGCCTTGAGTGGATTGGAGAGATTAAT CCTGCCAATGGTGATCATAACTTCAGTGAGAAGTTCGAGATCAAG GCCACACTGACTGTAGACAGCTCCTCCAACACAGCATTCATGCAA CTCAGCAGGCTGACATCTGAGGACTCTGCGGTCTATTACTGTACA AGATTGGACGATAGTAGGTTCCACTGGTACTTCGATGTCTGGGGC GCAGGGACCACGGTCACCGTCTCCTCAGGTGGAGGTGGCAGCGG AGGAGGTGGGTCCGGCGGTGGAGGAAGCCAAATTGTTCTCACCC AGTCTCCAGCGCTCATGTCTGCTTCTCCAGGGGAGAAGGTCACCA TGACCTGCACTGCCAGCTCAAGTGTTAGTTACATGTACTGGTACC AGCAGAAGCCACGATCCTCCCCCAAACCCTGGATTTTTCTCACCT CCAACCTGGCTTCTGGAGTCCCTGCTCGCTTCAGTGGCCGTGGGT CTGGGACCTCTTTCTCTCTCACAATCAGCAGCATGGAGGCTGAAG ATGCTGCCACTTATTACTGCCAGCAGTGGAGTGGTTACCCACCCA TCACATTCGGCTCGGGGACAAAGTTGGAAATAAAATCCGGaaccacg acgccagcgccgcgaccaccaacaccggcgcccaccatcgcgtcgcagcccctgtccctgcgcccagag gcgtgccggccagcggcggggggcgcagtgcacacgaggggctggacttcgcctgtgatatctacatct gggcgccttggccgggacttgtgggtcctctcctgtcactggttatcacccttactgcaaacggggcag aaagaaactcctgtatatattcaaacaaccatttatgagaccagtacaaaactactcaagaggaagatcgctgta gctgcgatttccagaagaagaagaaggaggatgtgaactgagagtgaagttcagcaggagcgcagacgc ccccgcgtacaagcagggccagaaccagctctataacgagctcaatctaggacgaagagaggagtacgat gtttggacaagagacgtggccgggaccctgagatgggggggaaagccgagaaggaagaaccctcaggaa ggcctgtacaatgaactgcagaaagataagatggcggaggcctacagtgagattgggatgaaaggcgagc gccggaggagcaaggggcacgatggcctttaccagggtctcagtacagccaccaaggacacctacgacg ccccttcacatgcaggccctgccccctcgctaa |
| 23 | 4G5_HG2L_CD8 H_BB_CD3Z CAR | MALPVTALLLPLALLLHAARPGSQVQLQQPGAELVKPGASVKLSCK ASGYTITSYSLHWVKQRPGQGLEWIGEINPANGDHNFSEKFEIKATL TVDSSSNTAFMQLSRLTSEDSAVYYCTRLDDSRFHWYFDVWGAGTT VTVSSGGGGSGGGGSGGGGSQIVLTQSPALMSASPGEKVTMTCTAS SSVSYMYWYQQKPRSSPKPWIFLTSNLASGVPARFSGRGSGTSFSLTI SSMEAEDAATYYCQQWSGYPPITPGSGTKLEIKSGTTTPAPRPPTPAP TIASQPLSLRPEACRPAAGGAVHTRGLDFACDIYIWAPLAGTCGGVLL LSLVITLYCKRGRKKLLYIFKQPFMRPVQTTQEEDGCSCRFPEEEEGG CELRVKFSRSADAPAYKQGQNQLYNELNLGRREEYDVLDKRRGRD PEMGGKPRRKNPQEGLYNELQKDMAEAYSEIGMKGERRRGKGHD GLYQGLSTATKDTYDALHMQALPPR |
| 24 | 4G5_L2HG_CD8 H_BB_CDEZ CAR | ATGGCCCTGCCTGTGACAGCCCTGCTGCTGCCTCTGGCTCTGCTGC TGCATGCCGCTAGACCCGGATCCCAAATTGTTCTCACCCAGTCTC CAGCGCTCATGTCTGCTTCTCCAGGGGAGAAGGTCACCATGACCT GCACTGCCAGCTCAAGTGTTAGTTACATGTACTGGTACCAGCAGA AGCCACGATCCTCCCCCAAACCCTGGATTTTTCTCACCTCCAACCT GGCTTCTGGAGTCCCTGCTCGCTTCAGTGGCCGTGGGTCTGGGAC CTCTTTCTCTCTCACAATCAGCAGCATGGAGGCTGAAGATGCTGC CACTTATTACTGCCAGCAGTGGAGTGGTTACCCACCCATCACATT CGGCTCGGGGACAAAGTTGGAAATAAAGGTGGAGGTGGCAGCG GAGGAGGTGGGTCCGGCGGTGGAGGAAGCCAGGTCCAACTGCAG CAGCCTGGGGCTGAACTGGTAAAGCCTGGGGCTTCAGTGAAGTTG TCCTGCAAGGCGTCTGGCTACACCATCACCAGCTACTCTCTGCAC TGGGTGAAGCAGAGGCCTGGACAAGGCCTTGAGTGGATTGGAGA GATTAATCCTGCCAATGGTGATCATAACTTCAGTGAGAAGTTCGA GATCAAGGCCACACTGACTGTAGACAGCTCCTCCAACACAGCATT CATGCAACTCAGCAGGCTGACATCTGAGGACTCTGCGGTCTATTA |

TABLE 1-continued

Nucleic acid and amino acid sequences

| SEQ ID NO: | Name | Amino Acid/Nucleotide Sequence |
|---|---|---|
| | | CTGTACAAGATTGGACGATAGTAGGTTCCACTGGTACTTCGATGT<br>CTGGGGCGCAGGGACCACGGTCACCGTCTCCTCATCCGGaaccacgac<br>gccagcgccgcgaccaccaacaccggcgcccaccatcgcgtcgcagccccctgtccctgcgcccagaggc<br>gtgccggccagcggcggggggcgcagtgcacacgaggggctggacttcgcctgtgatatctacatctgg<br>gcgcccttggccgggacttgtggggtccttctcctgtcactggttatcacccttactgcaaacggggcagaaa<br>gaaactcctgtatatattcaaacaaccatttatgagaccagtacaaactactcaagaggaagatggctgtagct<br>gccgatttccagaagaagaagaaggaggatgtgaactgagagtgaagttcagcaggagcgcagacgcccc<br>cgcgtacaagcagggccagaaccagctctataacgagctcaatctaggacgaagagaggagtacgatgttt<br>ggacaagagacgtggccgggaccctgagatgggggaaagccgagaaggaagaaccctcaggaaggc<br>ctgtacaatgaactgcagaaagataagatggcggaggcctacagtgagattgggatgaaaggcgagcgcc<br>ggagggggcaaggggcacgatggccttaccagggtctcagtacagccaccaaggacacctacgacgccct<br>tcacatgcaggccctgccccctcgctaa |
| 25 | 4G5_L2HG_CD8<br>H_BB_CD3Z<br>CAR | MALPVTALLLPLALLLHAARPGSQIVLTQSPALMSASPGEKVTMTCT<br>ASSSVSYMYWYQQKPRSSPKPWIFLTSNLASGVPARFSGRGSGTSFS<br>LTISSMEAEDAATYYCQQWSGYPPITFGSGTKLEIKGGGGSGGGGSG<br>GGGSQVQLQQPGAELVKPGASVKLSCKASGYTITSYSLHWVKQRPG<br>QGLEWIGEINPANGDHNFSEKFEIKATLTVDSSSNTAFMQLSRLTSED<br>SAVYYCTRLDDSRFHWYFDVWGAGTTVTVSSSGTTTPAPRPPTPAPT<br>IASQPLSLRPEACRPAAGGAVHTRGLDFACDIYIWAPLAGTCGVLLL<br>SLVITLYCKRGRKKLLYIFKQPFMRPVQTTQEEDGCSCRFPEEEEGGC<br>ELRVKFSRSADAPAYKQGQNQLYNELNLGRREEYDVLDKRRGRDPE<br>MGGKPRRKNPQEGLYNELQKDKMAEAYSEIGMKGERRRGKGHDG<br>LYQGLSTATKDTYDALHMQALPPR |
| 26 | Full Length<br>Canine FAP | ATGAAGACGTGGTTAAAAATTGTATTTGGAGTTGCCACCTCTGCT<br>GTGCTTGCTTTATTGGTGATGTGCATTGTCTTACGTCCTTCAAGAG<br>TTCATGACTCCGAAGGAGGTACAACAAGAGCACTCACACTGGAG<br>GATATTTTAAATGGGACATTTACCTATAAAACATTTTTTCCAAACT<br>GGATTTCAGGACAAGAATATCTTCATCAGTCTACAGATAATGATA<br>TAGTATATTACAATATTGAAACAGGAGAATCATATACCATTTTGA<br>GTAATGCCACCATGAAAAGTGTGAATGCTTCAAATTATGGCTTAT<br>CACCTGATCGTCAATTTGCATATCTAGAAAGTGATTATTCAAAGC<br>TTTGGAGATACTCTTACACTGCAACATATCACATCTATAACCTCA<br>ATAATGGAGAGTTTATAAGAAGAAATGAGCTTCCTCGTCAATTC<br>AGTATTTATGCTGGTCGCCTGTTGGGAGTAAATTAGCATATGTCT<br>ATCAAAACAATATCTATTTGAAACAAAGACCAGAAGACCCACCTT<br>TTCAAATAACATATAATGGAAGAGAAATAAAATATTCAATGGA<br>ATCCCAGACTGGGTATATGAAGAGGAAATGCTTGCTACAAAACA<br>TGCTCTCTGGTGGTCTCCTAATGGAAAATTTTTGGCATATGCAGA<br>ATTTAATGATACAGAGATACCAGTTATTGCCTATTCCTATTATGGT<br>GATGAACAATATCCTAGAACAATAAATATTCCATACCCAAAGGCT<br>GGAGCTAAGAACCCTGTTGTTCGGATCTTTATTATCGATACCACTT<br>ATCCTCAGCAGACAGGTCCCAGAGAAGTGCCAGTTCCAGCAATG<br>ATAGCATCAAGTGATTATTATTTCAGTTGGCTCACATGGGTTACT<br>GATGAACGAGTATGTTTGCAGTGGCTAAAAAGAATCCAGAACGT<br>TTCAGTTCTGTCCATATGTGATTTCAGGGAAGGCTGGCAGACATG<br>GGATTGTCCAAAGGCCCAGGAACATATAGAAGAAAGCAGAACTG<br>GATGGGCTGGTGGATTCTTTGTTTCAACACCAGTTTTCAGCTATGA<br>TGCCATTTCATACTACAAAATATTTAGCGACAAGGATGGCTACAA<br>ACATATTCACTATATCAAAGACACTGTGGAAAATGCTATTCAAAT<br>TACAAGTGGCAAGTGGGAGGCCATAAATATATTCAGAGTAACAC<br>AGGATTCACTGTTTTATTCTAGCAATGAATTTGAAGACTACCCAG<br>GAAGAAGAAATATCTATAGAATTAGCATTGGAAGCTCTCCTCCAA<br>GCAAAAAGTGCATTACTTGCCATCTAAGGAAAGAAAGGTGCCAA<br>TATTACACAGCAAGTTTCAGTGACTACGCCAAGTACTATGCACTT<br>ATCTGCTATGGCCCAGGCCTCCCCATTTCCACCCTTCATGACGGCC<br>ACACTGATCAAGAAATTAAAATCCTGGAAGAAAACAAAGAATTG<br>GAAAATGCTTTGAAAAATATCCAGCTGCCTAAAGAGGAAATTAA<br>GAAACTTGAAGTGGATGATATTACTTTATGGTACAAGATGATGCT<br>TCCTCCCCGGTTTGACAGATCAAAGAAGTATCCCTTGCTAATTCA<br>AGTGTATGGTGGTCCCTGCAGTCAGAGCGTAAAGTCTGTATTCAG<br>TATTAATTGGATTTCTTATCTTGCAAGTAAGGAAGGGATAGTCAT<br>TGCCTTGGTGGATGGCCGAGGAACAGCTTACCAAGGTGACAAAC<br>TCCTGTATGCAGTATATCGAAAGCTGGGTGTTTATGAAGTTGAGG<br>ACCAGATCACAGCCGTCAGAAAATTCATAGAAATGGGTTTCATTG<br>ATGAAAAAGAATAGCCATATGGGGCTGGTCCTATGGAGGCTAT<br>GTTTCATCACTGGCCCTTGCTTCAGGAACTGGTCTTTTCAAATGTG<br>GGATAGCAGTGGCTCCTGTCTCCAGCTGGGAATATTACGACTCTA<br>TCTACACAGAACGATTCATGGGCCTCCCAACAAAGAACGATAATC<br>TCGAGCACTACAAAAATTCAACTGTGATGGCAAGAGCAGAATAT<br>TTCAGAAATGTAGACATATCTTCTCATCCACGGAACAGCAGATGAT<br>AATGTGCACTTTCAAAACTCAGCCAGATTGCTAAAGCTCTGGTT<br>AATGCACAAGTGGATTTCCAGGCAATGTGGTACTCTGACCAGAAC |

TABLE 1-continued

Nucleic acid and amino acid sequences

| SEQ ID NO | Name | Amino Acid/Nucleotide Sequence |
|---|---|---|
| | | CATGGCATACCCGGCCTGTCCTCGAAGCACTTATATACCCGCATG ACCCACTTCCTAAAGCAGTGTTTTTCTTTGTCCGACTGA |
| 27 | 4G5 HCDR1 | GYTITSYSLH |
| 28 | 4G5 HCDR2 | EINPANGDHNFSEKFEIKAT |
| 29 | 4G5 HCDR3 | TRLDDSRFHWYFDV |
| 30 | 4G5 LCDR2 | LTSNLAS |

C. Nucleic Acids and Expression Vectors

The present disclosure provides a nucleic acid encoding a CAR. The nucleic acid of the present disclosure may comprise a polynucleotide sequence encoding any one of the CARs disclosed herein.

In one embodiment, a nucleic acid of the present disclosure comprises a polynucleotide sequence encoding a chimeric antigen receptor (CAR) capable of binding FAP, comprising an antigen-binding domain, a transmembrane domain, and an intracellular domain. The antigen-binding domain comprises a heavy chain variable region that comprises three heavy chain complementarity determining regions (HCDRs) and a light chain variable region that comprises three light chain complementarity determining regions (LCDRs).

In certain embodiments, the antigen-binding domain comprises a heavy chain variable region that comprises three heavy chain complementarity determining regions (HCDRs). In certain embodiments, HCDR1 comprises the amino acid sequence YTITSYSLH (SEQ ID NO: 1), and/or HCDR2 comprises the amino acid sequence EINPANGDHNFSEKFEIK (SEQ ID NO: 2), and/or HCDR3 comprises the amino acid sequence LDDSRFHWYFDV (SEQ ID NO: 3). The antigen-binding domain also comprises a light chain variable region that comprises three light chain complementarity determining regions (LCDRs). In certain embodiments, LCDR1 comprises the amino acid sequence TASSSVSYMY (SEQ ID NO: 4), and/or LCDR2 comprises the amino acid sequence LTSNLA (SEQ ID NO: 5), and/or LCDR3 comprises the amino acid sequence QQWSGYPPIT (SEQ ID NO: 6).

In certain embodiments, the antigen-binding domain comprises a heavy chain variable region that comprises three heavy chain complementarity determining regions (HCDRs). In certain embodiments, HCDR1 comprises the amino acid sequence GYTITSYSLH (SEQ ID NO: 27), and/or HCDR2 comprises the amino acid sequence EINPANGDHNFSEKFEIK (SEQ ID NO: 2), and/or HCDR3 comprises the amino acid sequence LDDSRFHWYFDV (SEQ ID NO: 3). The antigen-binding domain also comprises a light chain variable region that comprises three light chain complementarity determining regions (LCDRs). In certain embodiments, LCDR1 comprises the amino acid sequence TASSSVSYMY (SEQ ID NO: 4), and/or LCDR2 comprises the amino acid sequence LTSNLAS (SEQ ID NO: 30), and/or LCDR3 comprises the amino acid sequence QQWSGYPPIT (SEQ ID NO: 6).

In certain embodiments, the antigen-binding domain comprises a heavy chain variable region that comprises three heavy chain complementarity determining regions (HCDRs). In certain embodiments, HCDR1 comprises the amino acid sequence YTITSYSLH (SEQ ID NO: 1), and/or HCDR2 comprises the amino acid sequence EINPANGDHNFSEKFEIKAT (SEQ ID NO: 28), and/or HCDR3 comprises the amino acid sequence TRLDDSRFHWYFDV (SEQ ID NO: 29). The antigen-binding domain also comprises a light chain variable region that comprises three light chain complementarity determining regions (LCDRs). In certain embodiments, LCDR1 comprises the amino acid sequence TASSSVSYMY (SEQ ID NO: 4), and/or LCDR2 comprises the amino acid sequence LTSNLA (SEQ ID NO: 5), and/or LCDR3 comprises the amino acid sequence QQWSGYPPIT (SEQ ID NO: 6).

In certain embodiments, the antigen-binding domain comprises a heavy chain variable region that comprises any of the three heavy chain complementarity determining regions, HCDR1, HCDR2, and HCDR3, as described herein. In certain embodiments, the antigen-binding domain comprises a light chain variable region that comprises any of the three light chain complementarity determining regions, LCDR1, LCDR2, and LCDR3, as described herein. In certain embodiments, the antigen-binding domain comprises any combination of HCDR1, HCDR2, HCDR3, LCDR1, LCDR2, and LCDR3, and described herein. The skilled artisan would readily be able to determine the relevant complementarity determining regions based on amino acid numbering in view of the heavy and light chain variable region sequences provided herein.

In certain embodiments, the antigen-binding domain comprises a heavy chain variable region encoded by a polynucleotide sequence at least 80%, 85%, 90%, 95%, 96%, 97%, 98%, 99%, or 100% identical to SEQ ID NO: 8 and/or a light chain variable region encoded by a polynucleotide sequence at least 80%, 85%, 90%, 95%, 96%, 97%, 98%, 99%, or 100% identical to SEQ ID NO: 10.

In certain embodiments, the antigen-binding domain comprises a single-chain variable fragment (scFv) encoded by a polynucleotide sequence at least 80%, 85%, 90%, 95%, 96%, 97%, 98%, 99%, or 100% identical to SEQ ID NO: 12 or 14.

Also provided is a nucleic acid comprising a polynucleotide sequence encoding a CAR capable of binding FAP, comprising an antigen-binding domain, a transmembrane domain, and an intracellular domain, wherein the antigen-binding domain comprises: a heavy chain variable region encoded by a polynucleotide sequence at least 80%, 85%, 90%, 95%, 96%, 97%, 98%, 99%, or 100% identical to SEQ ID NO: 8; and a light chain variable region encoded by a polynucleotide sequence at least 80%, 85%, 90%, 95%, 96%, 97%, 98%, 99%, or 100% identical to SEQ ID NO: 10.

Further provided is a nucleic acid comprising a polynucleotide sequence at least 80%, 85%, 90%, 95%, 96%, 97%, 98%, 99%, or 100% identical to SEQ ID NO: 22 or 24.

In some embodiments, a nucleic acid of the present disclosure is provided for the production of a CAR as described herein, e.g., in a mammalian cell. In some embodiments, a nucleic acid of the present disclosure provides for amplification of the CAR-encoding nucleic acid.

In some embodiments, a nucleic acid of the present disclosure comprises a first polynucleotide sequence and a second polynucleotide sequence. In certain embodiments, the first polynucleotide sequence comprises a polynucleotide sequence encoding a FAP targeting CAR of the present disclosure. In some embodiments, The FAP targeting CARs of the present disclosure may be employed in combination with other therapeutic agents, for example, without limitation, immunotherapies such as immuno-oncology antibody therapy and checkpoint blockade, switch costimulatory receptors, or other CAR-T therapies. Accordingly, in such embodiments, the second polynucleotide sequence may comprise a polynucleotide sequence encoding for an anti-cancer antibody, a checkpoint blockade molecule, a switch costimulatory receptor, or a second chimeric antigen receptor.

The first and second polynucleotide sequence may be separated by a linker. A linker for use in the present disclosure allows for multiple proteins to be encoded by the same nucleic acid sequence (e.g., a multicistronic or bicistronic sequence), which may be translated as a polyprotein that is dissociated into separate protein components. In certain embodiments, the nucleic acid comprises from 5' to 3' the first polynucleotide sequence, the linker, and the second polynucleotide sequence. In certain embodiments, the nucleic acid comprises from 5' to 3' the second polynucleotide sequence, the linker, and the first polynucleotide sequence.

In some embodiments, the linker comprises a nucleic acid sequence that encodes for an internal ribosome entry site (IRES). As used herein, "an internal ribosome entry site" or "IRES" refers to an element that promotes direct internal ribosome entry to the initiation codon, such as ATG, of a protein coding region, thereby leading to cap-independent translation of the gene. Various internal ribosome entry sites are known to those of skill in the art, including, without limitation, IRES obtainable from viral or cellular mRNA sources, e.g., immunoglobulin heavy-chain binding protein (BiP); vascular endothelial growth factor (VEGF); fibroblast growth factor 2; insulin-like growth factor; translational initiation factor eIF4G; yeast transcription factors TFIID and HAP4; and IRES obtainable from, e.g., cardiovirus, rhinovirus, aphthovirus, HCV, Friend murine leukemia virus (FrMLV), and Moloney murine leukemia virus (MoMLV). Those of skill in the art would be able to select the appropriate IRES for use in the present invention.

In some embodiments, the linker comprises a nucleic acid sequence that encodes for a self-cleaving peptide. As used herein, a "self-cleaving peptide" or "2A peptide" refers to an oligopeptide that allow multiple proteins to be encoded as polyproteins, which dissociate into component proteins upon translation. Use of the term "self-cleaving" is not intended to imply a proteolytic cleavage reaction. Various self-cleaving or 2A peptides are known to those of skill in the art, including, without limitation, those found in members of the Picornaviridae virus family, e.g., foot-and-mouth disease virus (FMDV), equine rhinitis A virus (ERAV0, *Thosea asigna* virus (TaV), and porcine tescho virus-1 (PTV-1); and carioviruses such as Theilovirus and encephalomyocarditis viruses. 2A peptides derived from FMDV, ERAV, PTV-1, and TaV are referred to herein as "F2A," "E2A," "P2A," and "T2A," respectively. Those of skill in the art would be able to select the appropriate self-cleaving peptide for use in the present invention.

In some embodiments, a linker further comprises a nucleic acid sequence that encodes a furin cleavage site. Furin is a ubiquitously expressed protease that resides in the trans-golgi and processes protein precursors before their secretion. Furin cleaves at the COOH-terminus of its consensus recognition sequence. Various furin consensus recognition sequences (or "furin cleavage sites") are known to those of skill in the art, including, without limitation, Arg-X1-Lys-Arg (SEQ ID NO:117) or Arg-X1-Arg-Arg (SEQ ID NO:118), X2-Arg-X1-X3-Arg (SEQ ID NO:119) and Arg-X1-X1-Arg (SEQ ID NO:120), such as an Arg-Gln-Lys-Arg (SEQ ID NO:121), where X1 is any naturally occurring amino acid, X2 is Lys or Arg, and X3 is Lys or Arg. Those of skill in the art would be able to select the appropriate Furin cleavage site for use in the present invention.

In some embodiments, the linker comprises a nucleic acid sequence encoding a combination of a Furin cleavage site and a 2A peptide. Examples include, without limitation, a linker comprising a nucleic acid sequence encoding Furin and F2A, a linker comprising a nucleic acid sequence encoding Furin and E2A, a linker comprising a nucleic acid sequence encoding Furin and P2A, a linker comprising a nucleic acid sequence encoding Furin and T2A. Those of skill in the art would be able to select the appropriate combination for use in the present invention. In such embodiments, the linker may further comprise a spacer sequence between the Furin and 2A peptide. Various spacer sequences are known in the art, including, without limitation, glycine serine (GS) spacers such as (GS)n, (GSGGS)n (SEQ ID NO:31) and (GGGS)n (SEQ ID NO:32), where n represents an integer of at least 1. Exemplary spacer sequences can comprise amino acid sequences including, without limitation, GGSG (SEQ ID NO:34), GGSGG (SEQ ID NO:35), GSGSG (SEQ ID NO:36), GSGGG (SEQ ID NO:37), GGGSG (SEQ ID NO:38), GSSSG (SEQ ID NO:39), and the like. Those of skill in the art would be able to select the appropriate spacer sequence for use in the present invention.

In some embodiments, a nucleic acid of the present disclosure may be operably linked to a transcriptional control element, e.g., a promoter, and enhancer, etc. Suitable promoter and enhancer elements are known to those of skill in the art.

In certain embodiments, the nucleic acid encoding an exogenous CAR is in operable linkage with a promoter. In certain embodiments, the promoter is a phosphoglycerate kinase-1 (PGK) promoter.

For expression in a bacterial cell, suitable promoters include, but are not limited to, lad, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the promoter is a CD8 cell-specific promoter, a CD4 cell-specific promoter, a neutrophil-specific promoter, or an NK-specific promoter. For example, a CD4 gene promoter can be used; see, e.g., Salmon et al. Proc. Natl. Acad. Sci. USA (1993) 90:7739; and Marodon et al. (2003) Blood 101:3416. As another example, a CD8 gene promoter can be used. NK cell-specific expression can be achieved by use of an NcrI (p46) promoter; see, e.g., Eckelhart et al. Blood (2011) 117:1565.

For expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol. (1991) 173(1): 86-93; Alpuche-Aranda et al., Proc. Natl. Acad. Sci. USA (1992) 89(21): 10079-83), a nirB promoter (Harborne et al. Mol. Micro. (1992) 6:2805-2813), and the like (see, e.g., Dunstan et al., Infect. Immun. (1999) 67:5133-5141; McKelvie et al., Vaccine (2004) 22:3243-3255; and Chatfield et al., Biotechnol. (1992) 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al., Infect. Immun. (2002) 70:1087-1096); an rpsM promoter (see, e.g., Valdivia and Falkow Mol. Microbiol. (1996). 22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al., Nucl. Acids Res. (1984) 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., Proc. Natl. Acad. Sci. U.S.A. (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to a simian virus 40 (SV40) early promoter, a mouse mammary tumor virus (MMTV) or human immunodeficiency virus (HIV) long terminal repeat (LTR) promoter, a MoMuLV promoter, an avian leukemia virus promoter, an Epstein-Barr virus immediate early promoter, a Rous sarcoma virus promoter, the EF-1 alpha promoter, as well as human gene promoters such as, but not limited to, an actin promoter, a myosin promoter, a hemoglobin promoter, and a creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

In some embodiments, a nucleic acid of the present disclosure further comprises a nucleic acid sequence encoding a CAR inducible expression cassette. In one embodiment, the CAR inducible expression cassette is for the production of a transgenic polypeptide product that is released upon CAR signaling. See, e.g., Chmielewski and Abken, Expert Opin. Biol. Ther. (2015) 15(8): 1145-1154; and Abken, Immunotherapy (2015) 7(5): 535-544. In some embodiments, a nucleic acid of the present disclosure further comprises a nucleic acid sequence encoding a cytokine operably linked to a T-cell activation responsive promoter. In some embodiments, the cytokine operably linked to a T-cell activation responsive promoter is present on a separate nucleic acid sequence. In one embodiment, the cytokine is IL-12.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example, and should not be construed in anyway as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest. Opthalmol. Vis. Sci. (1994) 35: 2543-2549; Borras et al., Gene Ther. (1999) 6: 515-524; Li and Davidson, Proc. Natl. Acad. Sci. USA (1995) 92: 7700-7704; Sakamoto et al., H. Gene Ther. (1999) 5: 1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9: 81-86, Flannery et al., Proc. Natl. Acad. Sci. USA (1997) 94: 6916-6921; Bennett et al., Invest. Opthalmol. Vis. Sci. (1997) 38: 2857-2863; Jomary et al., Gene Ther. (1997) 4:683 690, Rolling et al., Hum. Gene Ther. (1999) 10: 641-648; Ali et al., Hum. Mol. Genet. (1996) 5: 591-594; Srivastava in WO 93/09239, Samulski et al., J. Vir. (1989) 63: 3822-3828; Mendelson et al., Virol. (1988) 166: 154-165; and Flotte et al., Proc. Natl. Acad. Sci. USA (1993) 90: 10613-10617); SV40; herpes simplex virus; human immunodeficiency virus (see, e.g., Miyoshi et al., Proc. Natl. Acad. Sci. USA (1997) 94: 10319-23; Takahashi et al., J. Virol. (1999) 73: 7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In some embodiments, an expression vector (e.g., a lentiviral vector) may be used to introduce the CAR into an immune cell or precursor thereof (e.g., a T cell). Accordingly, an expression vector (e.g., a lentiviral vector) of the present invention may comprise a nucleic acid encoding for a CAR. In some embodiments, the expression vector (e.g., lentiviral vector) will comprise additional elements that will aid in the functional expression of the CAR encoded therein. In some embodiments, an expression vector comprising a nucleic acid encoding for a CAR further comprises a mammalian promoter. In one embodiment, the vector further comprises an elongation-factor-1-alpha promoter (EF-1α promoter). Use of an EF-1α promoter may increase the efficiency in expression of downstream transgenes (e.g., a CAR encoding nucleic acid sequence). Physiologic promoters (e.g., an EF-la promoter) may be less likely to induce integration mediated genotoxicity, and may abrogate the ability of the retroviral vector to transform stem cells. Other physiological promoters suitable for use in a vector (e.g., lentiviral vector) are known to those of skill in the art and may be incorporated into a vector of the present invention. In some embodiments, the vector (e.g., lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention. In some embodiments, the vector further comprises a posttranscriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In one embodiment, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, 5'LTR, 3' U3 deleted LTR' in addition to a nucleic acid encoding for a CAR.

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding a CAR of the present disclosure. Methods for introducing RNA into a host cell are known in the art. See, e.g., Zhao et al. Cancer Res. (2010) 15: 9053. Introducing RNA comprising a nucleotide sequence encoding a CAR of the present disclosure into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding a CAR of the present disclosure.

In order to assess the expression of a polypeptide or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, without limitation, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

D. Modified Immune Cells

The present invention provides modified immune cells or precursors thereof (e.g., a T cell) comprising a chimeric antigen receptor (CAR) capable of binding FAP (e.g. human, canine, and/or mouse FAP). The invention also includes modified immune cells or precursors thereof comprising any of the CARs disclosed herein, any of the nucleic acids disclosed herein, or any of the vectors disclosed herein.

One aspect of the invention provides a modified immune cell or precursor cell thereof, comprising a CAR capable of binding FAP, wherein the CAR comprises: a heavy chain variable region that comprises three heavy chain complementarity determining regions (HCDRs) and a light chain variable region that comprises three light chain complementarity determining regions (LCDRs).

In certain embodiments, the antigen-binding domain comprises a heavy chain variable region that comprises three heavy chain complementarity determining regions (HCDRs). In certain embodiments, HCDR1 comprises the amino acid sequence YTITSYSLH (SEQ ID NO: 1), and/or HCDR2 comprises the amino acid sequence EINPANGDHNFSEKFEIK (SEQ ID NO: 2), and/or HCDR3 comprises the amino acid sequence LDDSRFHWYFDV (SEQ ID NO: 3). The antigen-binding domain also comprises a light chain variable region that comprises three light chain complementarity determining regions (LCDRs). In certain embodiments, LCDR1 comprises the amino acid sequence TASSSVSYMY (SEQ ID NO: 4), and/or LCDR2 comprises the amino acid sequence LTSNLA (SEQ ID NO: 5), and/or LCDR3 comprises the amino acid sequence QQWSGYPPIT (SEQ ID NO: 6).

In certain embodiments, the antigen-binding domain comprises a heavy chain variable region that comprises three heavy chain complementarity determining regions (HCDRs). In certain embodiments, HCDR1 comprises the amino acid sequence GYTITSYSLH (SEQ ID NO: 27), and/or HCDR2 comprises the amino acid sequence EINPANGDHNFSEKFEIK (SEQ ID NO: 2), and/or HCDR3 comprises the amino acid sequence LDDSRFHWYFDV (SEQ ID NO: 3). The antigen-binding domain also comprises a light chain variable region that comprises three light chain complementarity determining regions (LCDRs). In certain embodiments, LCDR1 comprises the amino acid sequence TASSSVSYMY (SEQ ID NO: 4), and/or LCDR2 comprises the amino acid sequence LTSNLAS (SEQ ID NO: 30), and/or LCDR3 comprises the amino acid sequence QQWSGYPPIT (SEQ ID NO: 6).

In certain embodiments, the antigen-binding domain comprises a heavy chain variable region that comprises three heavy chain complementarity determining regions (HCDRs). In certain embodiments, HCDR1 comprises the amino acid sequence YTITSYSLH (SEQ ID NO: 1), and/or HCDR2 comprises the amino acid sequence EINPANGDHNFSEKFEIKAT (SEQ ID NO: 28), and/or HCDR3 comprises the amino acid sequence TRLDDSRFHWYFDV (SEQ ID NO: 29). The antigen-binding domain also comprises a light chain variable region that comprises three light chain complementarity determining regions (LCDRs). In certain embodiments, LCDR1 comprises the amino acid sequence TASSSVSYMY (SEQ ID NO: 4), and/or LCDR2 comprises the amino acid sequence LTSNLA (SEQ ID NO: 5), and/or LCDR3 comprises the amino acid sequence QQWSGYPPIT (SEQ ID NO: 6).

In certain embodiments, the antigen-binding domain comprises a heavy chain variable region that comprises any of the three heavy chain complementarity determining regions, HCDR1, HCDR2, and HCDR3, as described herein. In certain embodiments, the antigen-binding domain comprises a light chain variable region that comprises any of the three light chain complementarity determining regions, LCDR1, LCDR2, and LCDR3, as described herein. In certain embodiments, the antigen-binding domain comprises any combination of HCDR1, HCDR2, HCDR3, LCDR1, LCDR2, and LCDR3, and described herein. The skilled artisan would readily be able to determine the relevant complementarity determining regions based on amino acid numbering in view of the heavy and light chain variable region sequences provided herein.

Another aspect of the invention provides a modified immune cell or precursor cell thereof, comprising a CAR capable of binding FAP, wherein the CAR comprises: a heavy chain variable region comprising an amino acid sequence at least 80%, 85%, 90%, 95%, 96%, 97%, 98%, 99%, or 100% identical to SEQ ID NO: 7 and/or a light chain variable region comprising an amino acid sequence at least 80%, 85%, 90%, 95%, 96%, 97%, 98%, 99%, or 100% identical to SEQ ID NO: 9.

Also provided is a modified immune cell or precursor cell thereof, comprising a CAR capable of binding FAP, wherein the CAR comprises a single-chain variable fragment (scFv) comprising an amino acid sequence at least 80%, 85%, 90%, 95%, 96%, 97%, 98%, 99%, or 100% identical to SEQ ID NO: 11 or 13.

Further provided is a modified immune cell or precursor cell thereof, comprising a CAR capable of binding FAP, wherein the CAR comprises an amino acid sequence at least 80%, 85%, 90%, 95%, 96%, 97%, 98%, 99%, or 100% identical to SEQ ID NO: 23 or 25.

In certain embodiments, the modified cell is a modified T cell. In certain embodiments, the modified cell is a modified NK cell. In certain embodiments, the modified cell is an autologous cell. In certain embodiments, the modified cell is an autologous cell obtained from a human subject. In certain embodiments, the modified cell is an autologous cell obtained from a canine subject. In certain embodiments, the modified cell is an allogeneic cell.

E. Sources of Immune Cells

In certain embodiments, a source of immune cells (e.g. T cells) is obtained from a subject for ex vivo manipulation. Sources of immune cells for ex vivo manipulation may also include, e.g., autologous or heterologous donor blood, cord blood, or bone marrow. For example, the source of immune cells may be from the subject to be treated with the modified immune cells of the invention, e.g., the subject's blood, the subject's cord blood, or the subject's bone marrow. Non-limiting examples of subjects include humans, dogs, cats, mice, rats, and transgenic species thereof. Preferably, the subject is a human.

Immune cells can be obtained from a number of sources, including blood, peripheral blood mononuclear cells, bone marrow, lymph node tissue, spleen tissue, umbilical cord, lymph, or lymphoid organs. Immune cells are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some aspects, the cells are human cells. With reference to the subject to be treated, the cells may be allogeneic and/or autologous. The cells typically are primary cells, such as those isolated directly from a subject and/or isolated from a subject and frozen.

In certain embodiments, the immune cell is a T cell, e.g., a CD8+ T cell (e.g., a CD8+ naive T cell, central memory T cell, or effector memory T cell), a CD4+ T cell, a natural killer T cell (NKT cells), a regulatory T cell (Treg), a stem cell memory T cell, a lymphoid progenitor cell a hematopoietic stem cell, a natural killer cell (NK cell) or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naive T cell, central memory T cell, or effector memory T cell), a CD4+ T cell, a stem cell memory T cell, a lymphoid progenitor cell or a hematopoietic stem cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In certain embodiments, any number of T cell lines available in the art, may be used.

In some embodiments, the methods include isolating immune cells from the subject, preparing, processing, culturing, and/or engineering them. In some embodiments, preparation of the engineered cells includes one or more culture and/or preparation steps. The cells for engineering as described may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig. In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components. In some embodiments, the cell line is an NK cell line (such as the NK92 or NK92-MI cell line).

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets. In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some aspects, a washing step is accomplished by tangential flow filtration (TFF) according to the manufacturer's instructions. In some embodiments, the cells are resuspended in a variety of biocompatible buffers after washing. In certain embodiments, components of a blood cell sample are removed and the cells directly resuspended in culture media. In some embodiments, the methods include density-based cell separation methods, such as the preparation of white blood cells from peripheral blood by lysing the red blood cells and centrifugation through a Percoll or Ficoll gradient.

In one embodiment, immune cells are obtained cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, one or more of the T cell populations is enriched for or depleted of cells that are positive for (marker+) or express high levels (marker$^{high}$) of one or more particular markers, such as surface markers, or that are negative for (marker —) or express relatively low levels (marker$^{low}$) of one or more markers. For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD 127, and/or CD62L and/or depleted of (e.g., negatively selected for) cells that are positive for or express high surface levels of CD45RA. In some embodiments, cells are enriched for or depleted of cells positive or expressing high surface levels of CD 122, CD95, CD25, CD27, and/or IL7-Ra (CD 127). In some examples, CD8+ T cells are enriched for cells positive for CD45RO (or negative for CD45RA) and for CD62L. For example, CD3+, CD28+ T cells can be positively selected using CD3/CD28 conjugated magnetic beads (e.g., DYNABEADS® M-450 CD3/CD28 T Cell Expander).

In some embodiments, T cells are separated from a PBMC sample by negative selection of markers expressed on non-T cells, such as B cells, monocytes, or other white blood cells, such as CD 14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations. In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such sub-populations. In some embodiments, combining TCM-enriched CD8+ T cells and CD4+ T cells further enhances efficacy.

In some embodiments, memory T cells are present in both CD62L+ and CD62L-subsets of CD8+ peripheral blood lymphocytes. PBMC can be enriched for or depleted of CD62L-CD8+ and/or CD62L+CD8+ fractions, such as using anti-CD8 and anti-CD62L antibodies. In some embodiments, a CD4+ T cell population and a CD8+ T cell sub-population, e.g., a sub-population enriched for central memory (TCM) cells. In some embodiments, the enrichment for central memory T (TCM) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a CD8+ population enriched for TCM cells is carried out by depletion of cells expressing CD4, CD 14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD 14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+ T helper cells are sorted into naive, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO. In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In another embodiment, T cells are isolated from peripheral blood by lysing the red blood cells and depleting the monocytes, for example, by centrifugation through a PER-COLL™ gradient. Alternatively, T cells can be isolated from an umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19, and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4$^+$ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In one embodiment, the T cell is comprised within a population of cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

In certain embodiments, T regulatory cells (Tregs) can be isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. Methods for isolating Tregs are described in U.S. Pat. Nos. 7,754,482, 8,722,400, and 9,555,105, and U.S. patent application Ser. No. 13/639,927, contents of which are incorporated herein in their entirety.

F. Methods of Treatment

The modified immune cells (e.g., T cells or NK cells) described herein may be included in a composition for immunotherapy. The composition may include a pharmaceutical composition and further include a pharmaceutically acceptable carrier. A therapeutically effective amount of the pharmaceutical composition comprising the modified T cells or NK cells may be administered to a subject in need thereof.

In one aspect, the invention includes a method of treating a disease or condition in a subject in need thereof. The method comprises administering to the subject an effective amount of a modified T cell of the present invention. In another aspect, the invention includes a method of treating a disease or condition in a subject comprising administering to the subject a pharmaceutical composition comprising an effective amount of a modified T cell of the present invention. In another aspect, the invention includes a method for adoptive cell transfer therapy comprising administering to a subject in need thereof an effective amount of a modified T cell of the present invention. Diseases that can be treated include but are not limited to immunological diseases, hematological diseases, autoimmune diseases, fibrosis, and cancer.

Methods for administration of immune cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338. In some embodiments, the cell therapy, e.g., adoptive T cell therapy is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject has been treated with a therapeutic agent targeting the disease or condition, e.g. the tumor, prior to administration of the cells or composition containing the cells. In some aspects, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse. In some aspects, the subject has not received prior treatment with another therapeutic agent.

In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

The modified immune cells of the present invention can be administered to an animal (e.g. a dog), preferably a mammal, even more preferably a human, to treat a cancer. In certain embodiments, the cancer comprises a FAP-expressing cancer-associated cell. In certain embodiments, the FAP-expressing cancer-associated cell is a cancer-associated fibroblast (CAF). In certain embodiments, the FAP-expressing cancer-associated cell is a FAP-expressing adipocyte. In certain embodiments, the FAP-expressing cancer-associated cell is a tumor-associated macrophage (TAM). In certain embodiments, the FAP-expressing cancer-associated cell is a tumor-associated neutrophil (TAN). In certain embodiments, the FAP-expressing cancer-associated cell is a myeloid-derived suppressor cell (MDSC). In certain embodiments, the FAP-expressing cancer-associated cell is a cancer-initiating cell.

In addition, the cells of the present invention can be used for the treatment of any condition related to a cancer, especially a cell-mediated immune response against a tumor cell(s), where it is desirable to treat or alleviate the disease. The types of cancers to be treated with the modified cells or pharmaceutical compositions of the invention include, carcinoma, blastoma, and sarcoma, and certain leukemia or lymphoid malignancies, benign and malignant tumors, and malignancies e.g., sarcomas, carcinomas, and melanomas. Other exemplary cancers include but are not limited breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. The cancers may be non-solid tumors (such as hematological tumors) or solid tumors. Adult tumors/cancers and pediatric tumors/cancers are also included. In one embodiment, the cancer is a solid tumor or a hematological tumor. In one embodiment, the cancer is a carcinoma. In one embodiment, the cancer is a sarcoma. In one embodiment, the cancer is a leukemia. In one embodiment the cancer is a solid tumor.

The successful treatment of solid tumors has been hampered by various obstacles, including, e.g., the tumor microenvironment. Tumors comprise cancer cells as well as a stromal compartment comprising cellular and non-cellular components. The tumor stroma has been shown to have critical roles in the development of cancer, including progression and metastasis. A CAR of the subject disclosure may be employed in a method for treating a disease or condition by targeting tumor stroma, where potential cellular targets in the stroma include cancer-associated fibroblasts (CAFs). CAFs have been shown to enhance almost every aspect of tumor growth and spread. CAFs present a barrier to therapeutic agents (e.g., drugs and immune cells), provide growth signals to tumor cells, and are actively immunosuppressive.

The present invention provides chimeric antigen receptors (CARs) capable of binding Fibroblast Activation Protein (FAP). FAP is a type II transmembrane serine protease that is expressed in the stroma of over 90% of common human epithelial cancers. In certain tumors, it is selectively expressed by cancer-associated fibroblasts. Expression of FAP has not been detected in benign tumors or normal adult quiescent tissues.

In some embodiments, a method present disclosure employs a modified immune cell of the present disclosure in combination with other therapeutic agents, for example, without limitation, immunotherapies such as immuno-oncology antibody therapy and checkpoint blockade, switch costimulatory receptors, or other CAR-T therapies.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases). In certain embodiments, the cancer is an astrocytoma. In certain embodiments, the cancer is a high-grade astrocytoma.

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

In certain exemplary embodiments, the modified immune cells of the invention are used to treat a myeloma, or a condition related to myeloma. Examples of myeloma or conditions related thereto include, without limitation, light chain myeloma, non-secretory myeloma, monoclonal gamopathy of undetermined significance (MGUS), plasmacytoma (e.g., solitary, multiple solitary, extramedullary plasmacytoma), amyloidosis, and multiple myeloma. In one embodiment, a method of the present disclosure is used to treat multiple myeloma. In one embodiment, a method of the present disclosure is used to treat refractory myeloma. In one embodiment, a method of the present disclosure is used to treat relapsed myeloma.

In certain exemplary embodiments, the modified immune cells of the invention are used to treat a melanoma, or a condition related to melanoma. Examples of melanoma or conditions related thereto include, without limitation, superficial spreading melanoma, nodular melanoma, lentigo maligna melanoma, acral lentiginous melanoma, amelanotic melanoma, or melanoma of the skin (e.g., cutaneous, eye, vulva, vagina, rectum melanoma). In one embodiment, a method of the present disclosure is used to treat cutaneous melanoma. In one embodiment, a method of the present disclosure is used to treat refractory melanoma. In one embodiment, a method of the present disclosure is used to treat relapsed melanoma.

In yet other exemplary embodiments, the modified immune cells of the invention are used to treat a sarcoma, or a condition related to sarcoma. Examples of sarcoma or conditions related thereto include, without limitation, angiosarcoma, chondrosarcoma, Ewing's sarcoma, fibrosarcoma, gastrointestinal stromal tumor, leiomyosarcoma, liposarcoma, malignant peripheral nerve sheath tumor, osteosarcoma, pleomorphic sarcoma, rhabdomyosarcoma, and synovial sarcoma. In one embodiment, a method of the present disclosure is used to treat synovial sarcoma. In one embodiment, a method of the present disclosure is used to treat liposarcoma such as myxoid/round cell liposarcoma, differentiated/dedifferentiated liposarcoma, and pleomorphic liposarcoma. In one embodiment, a method of the present disclosure is used to treat myxoid/round cell liposarcoma. In one embodiment, a method of the present disclosure is used to treat a refractory sarcoma. In one embodiment, a method of the present disclosure is used to treat a relapsed sarcoma.

In certain embodiments, the methods disclosed herein are used to treat an immunological disease. Immunological diseases that can be treated include but are not limited to scleroderma and arthritis (such as rheumatoid or osteoarthritis).

In certain embodiments, the methods disclosed herein are used to treat a hematological disease. Hematological diseases that can be treated include but are not limited to multiple myeloma or myelofibrosis.

In certain embodiments, the methods disclosed herein are used to treat any type of fibrosis including, but not limited to, lung fibrosis, liver fibrosis, skin fibrosis (keloids and scleroderma) intestinal fibrosis, and kidney fibrosis. In certain embodiments, the methods disclosed herein are used to treat cardiac fibrosis. Additional diseases or disorders that may be treated include but are not limited to hypertensive heart disease, diastolic dysfunction, heart failure with preserved ejection fraction, myocardial infarction, ischemic cardiomyopathy, hypertrophic cardiomyopathy, arrhythmias including atrial fibrillation, arrhythmogenic right ventricular dysplasia, dilated cardiomyopathy (including idiopathic and familial forms), hypertensive heart disease, inherited forms including muscular dystrophy, infective cardiomyopathy (e.g. Chagas disease, rheumatic fever), transplant cardiomyopathy, radiation induced cardiac fibrosis, autoimmune (Sarcoid cardiomyopathy, lupus), toxin or drug related, amyloidosis, diabetic cardiomyopathy, and other types of cardiac fibrosis including but not limited to reactive interstitial fibrosis, replacement fibrosis, infiltrative interstitial fibrosis, and endomyocardial fibrosis.

The cells of the invention to be administered may be autologous, with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as $CD8^+$ and $CD4^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as $CD4^+$ to $CD8^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or subtype, or minimum number of cells of the population or sub-type per unit of body weight. Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In certain embodiments, the cells, or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $1 \times 10^5$ cells/kg to about $1 \times 10^{11}$ cells/kg $10^4$ and at or about $10^{11}$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^6$ T cells/kg body weight, for example, at or about $1\times10^5$ T cells/kg, $1.5\times10^5$ T cells/kg, $2\times10^5$ T cells/kg, or $1\times10^6$ T cells/kg body weight. In other exemplary embodiments, a suitable dosage range of modified cells for use in a method of the present disclosure includes, without limitation, from about $1\times10^5$ cells/kg to about $1\times10^6$ cells/kg, from about $1\times10^6$ cells/kg to about $1\times10^7$ cells/kg, from about $1\times10^7$ cells/kg about $1\times10^8$ cells/kg, from about $1\times10^8$ cells/kg about $1\times10^9$ cells/kg, from about $1\times10^9$ cells/kg about $1\times10^{10}$ cells/kg, from about $1\times10^{10}$ cells/kg about $1\times10^{11}$ cells/kg. In an exemplary embodiment, a suitable dosage for use in a method of the present disclosure is about $1\times10^8$ cells/kg. In an exemplary embodiment, a suitable dosage for use in a method of the present disclosure is about $1\times10^7$ cells/kg. In other embodiments, a suitable dosage is from about $1\times10^7$ total cells to about $5\times10^7$ total cells. In some embodiments, a suitable dosage is from about $1\times10^8$ total cells to about $5\times10^8$ total cells. In some embodiments, a suitable dosage is from about $1.4\times10^7$ total cells to about $1.1\times10^9$ total cells. In an exemplary embodiment, a suitable dosage for use in a method of the present disclosure is about $7\times10^9$ total cells.

In some embodiments, the cells are administered at or within a certain range of error of between at or about $10^4$ and at or about $10^9$ CD4$^+$ and/or CD8$^+$ cells/kilograms (kg) body weight, such as between $10^5$ and $10^6$ CD4$^+$ and/or CD8$^+$ cells/kg body weight, for example, at or about $1\times10^5$ CD4$^+$ and/or CD8$^+$ cells/kg, $1.5\times10^5$ CD4$^+$ and/or CD8$^+$ cells/kg, $2\times10^5$ CD4$^+$ and/or CD8$^+$ cells/kg, or $1\times10^6$ CD4$^+$ and/or CD8$^+$ cells/kg body weight. In some embodiments, the cells are administered at or within a certain range of error of, greater than, and/or at least about $1\times10^6$, about $2.5\times10^6$, about $5\times10^6$, about $7.5\times10^6$, or about $9\times10^6$ CD4$^+$ cells, and/or at least about $1\times10^6$, about $2.5\times10^6$, about $5\times10^6$, about $7.5\times10^6$, or about $9\times10^6$ CD8$^+$ cells, and/or at least about $1\times10^6$, about $2.5\times10^6$, about $5\times10^6$, about $7.5\times10^6$, or about $9\times10^6$ T cells. In some embodiments, the cells are administered at or within a certain range of error of between about $10^8$ and $10^{12}$ or between about $10^{10}$ and $10^{11}$ T cells, between about $10^8$ and $10^{12}$ or between about $10^{10}$ and $10^{11}$ CD4$^+$ cells, and/or between about $10^8$ and $10^{12}$ or between about $10^{10}$ and $10^{11}$ CD8$^+$ cells.

In some embodiments, the cells are administered at or within a tolerated range of a desired output ratio of multiple cell populations or sub-types, such as CD4$^+$ and CD8$^+$ cells or sub-types. In some aspects, the desired ratio can be a specific ratio or can be a range of ratios, for example, in some embodiments, the desired ratio (e.g., ratio of CD4$^+$ to CD8$^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, a dose of modified cells is administered to a subject in need thereof, in a single dose or multiple doses. In some embodiments, a dose of modified cells is administered in multiple doses, e.g., once a week or every 7 days, once every 2 weeks or every 14 days, once every 3 weeks or every 21 days, once every 4 weeks or every 28 days. In an exemplary embodiment, a single dose of modified cells is administered to a subject in need thereof. In an exemplary embodiment, a single dose of modified cells is administered to a subject in need thereof by rapid intravenous infusion.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent or an anti-tumor vaccine. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

In certain embodiments, the modified cells of the invention (e.g., a modified cell comprising a CAR) may be administered to a subject in combination with an inhibitor of an immune checkpoint. Examples of immune checkpoints include but are not limited to CTLA-4, PD-1, and TIM-3. Antibodies may be used to inhibit an immune checkpoint (e.g., an anti-PD1, anti-CTLA-4, or anti-TIM-3 antibody). For example, the modified cell may be administered in combination with an antibody or antibody fragment targeting, for example, PD-1 (programmed death 1 protein). Examples of anti-PD-1 antibodies include, but are not limited to, pembrolizumab (KEYTRUDA®, formerly lambrolizumab, also known as MK-3475), and nivolumab (BMS-936558, MDX-1106, ONO-4538, OPDIVA®) or an antigen-binding fragment thereof. In certain embodiments, the modified cell may be administered in combination with an anti-PD-L1 antibody or antigen-binding fragment thereof. Examples of anti-PD-L1 antibodies include, but are not limited to, BMS-936559, MPDL3280A (TECENTRIQ®, Atezolizumab), and MEDI4736 (Durvalumab, Imfinzi). In certain embodiments, the modified cell may be administered in combination with an anti-CTLA-4 antibody or antigen-binding fragment thereof. An example of an anti-CTLA-4 antibody includes, but is not limited to, Ipilimumab (trade name Yervoy). Other types of immune checkpoint modulators may also be used including, but not limited to, small molecules, siRNA, miRNA, and CRISPR systems. Immune checkpoint modulators may be administered before, after, or concurrently with the modified cell comprising the CAR. In certain embodiments, combination treatment comprising an immune checkpoint modulator may increase the therapeutic efficacy of a therapy comprising a modified cell of the present invention.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

In certain embodiments, the subject is provided a secondary treatment. Secondary treatments include but are not limited to chemotherapy, radiation, surgery, and medications.

In some embodiments, the subject can be administered a conditioning therapy prior to CAR T cell therapy. In some embodiments, the conditioning therapy comprises administering an effective amount of cyclophosphamide to the subject. In some embodiments, the conditioning therapy comprises administering an effective amount of fludarabine to the subject. In preferred embodiments, the conditioning therapy comprises administering an effective amount of a combination of cyclophosphamide and fludarabine to the subject. Administration of a conditioning therapy prior to CAR T cell therapy may increase the efficacy of the CAR T cell therapy. Methods of conditioning patients for T cell therapy are described in U.S. Pat. No. 9,855,298, which is incorporated herein by reference in its entirety.

In some embodiments, a specific dosage regimen of the present disclosure includes a lymphodepletion step prior to the administration of the modified T cells. In an exemplary embodiment, the lymphodepletion step includes administration of cyclophosphamide and/or fludarabine.

In some embodiments, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day). In an exemplary embodiment, the dose of cyclophosphamide is about 300 mg/m$^2$/day. In some embodiments, the lymphodepletion step includes administration of fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the dose of fludarabine is about 30 mg/m$^2$/day.

In some embodiment, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the lymphodepletion step includes administration of cyclophosphamide at a dose of about 300 mg/m$^2$/day, and fludarabine at a dose of about 30 mg/m$^2$/day.

In an exemplary embodiment, the dosing of cyclophosphamide is 300 mg/m$^2$/day over three days, and the dosing of fludarabine is 30 mg/m$^2$/day over three days.

Dosing of lymphodepletion chemotherapy may be scheduled on Days −6 to −4 (with a −1 day window, i.e., dosing on Days −7 to −5) relative to T cell (e.g., CAR-T, TCR-T, a modified T cell, etc.) infusion on Day 0.

In an exemplary embodiment, for a subject having cancer, the subject receives lymphodepleting chemotherapy including 300 mg/m$^2$ of cyclophosphamide by intravenous infusion 3 days prior to administration of the modified T cells. In an exemplary embodiment, for a subject having cancer, the subject receives lymphodepleting chemotherapy including 300 mg/m$^2$ of cyclophosphamide by intravenous infusion for 3 days prior to administration of the modified T cells.

In an exemplary embodiment, for a subject having cancer, the subject receives lymphodepleting chemotherapy including fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having cancer, the subject receives lymphodepleting chemotherapy including fludarabine at a dose of 30 mg/m$^2$ for 3 days.

In an exemplary embodiment, for a subject having cancer, the subject receives lymphodepleting chemotherapy including cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having cancer, the subject receives lymphodepleting chemotherapy including cyclophosphamide at a dose of about 300 mg/m$^2$/day, and fludarabine at a dose of 30 mg/m$^2$ for 3 days.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

It is known in the art that one of the adverse effects following infusion of CAR T cells is the onset of immune activation, known as cytokine release syndrome (CRS). CRS is immune activation resulting in elevated inflammatory cytokines. CRS is a known on-target toxicity, development of which likely correlates with efficacy. Clinical and laboratory measures range from mild CRS (constitutional symptoms and/or grade-2 organ toxicity) to severe CRS (sCRS; grade ≥3 organ toxicity, aggressive clinical intervention, and/or potentially life threatening). Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. One CRS signature is elevation of cytokines including IL-6 (severe elevation), IFN-gamma, TNF-alpha (moderate), and IL-2 (mild). Elevations in clinically available markers of inflammation including ferritin and C-reactive protein (CRP) have also been observed to correlate with the CRS syndrome. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, the invention provides for, following the diagnosis of CRS, appropriate CRS management strategies to mitigate the physiological symptoms of uncontrolled inflammation without dampening the antitumor efficacy of the engineered cells (e.g., CAR T cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

CRS is generally managed based on the severity of the observed syndrome and interventions are tailored as such. CRS management decisions may be based upon clinical signs and symptoms and response to interventions, not solely on laboratory values alone.

Mild to moderate cases generally are treated with symptom management with fluid therapy, non-steroidal anti-inflammatory drug (NSAID) and antihistamines as needed for adequate symptom relief. More severe cases include patients with any degree of hemodynamic instability; with any hemodynamic instability, the administration of tocilizumab is recommended. The first-line management of CRS may be tocilizumab, in some embodiments, at the labeled dose of 8 mg/kg IV over 60 minutes (not to exceed 800 mg/dose); tocilizumab can be repeated Q8 hours. If suboptimal response to the first dose of tocilizumab, additional doses of tocilizumab may be considered. Tocilizumab can be administered alone or in combination with corticosteroid therapy. Patients with continued or progressive CRS symptoms, inadequate clinical improvement in 12-18 hours or poor response to tocilizumab, may be treated with high-dose corticosteroid therapy, generally hydrocortisone 100 mg IV or methylprednisolone 1-2 mg/kg. In patients with more severe hemodynamic instability or more severe respiratory symptoms, patients may be administered high-dose corticosteroid therapy early in the course of the CRS. CRS management guidance may be based on published standards (Lee et al. (2019) *Biol Blood Marrow Transplant*, doi.org/10.1016/j.bbmt.2018.12.758; Neelapu et al. (2018) *Nat Rev Clin Oncology*, 15:47; Teachey et al. (2016) *Cancer Discov*, 6(6):664-679).

Features consistent with Macrophage Activation Syndrome (MAS) or Hemophagocytic lymphohistiocytosis (HLH) have been observed in patients treated with CAR-T therapy (Henter, 2007), coincident with clinical manifestations of the CRS. MAS appears to be a reaction to immune activation that occurs from the CRS, and should therefore be considered a manifestation of CRS. MAS is similar to HLH (also a reaction to immune stimulation). The clinical syndrome of MAS is characterized by high grade non-remitting fever, cytopenias affecting at least two of three lineages, and hepatosplenomegaly. It is associated with high serum ferritin, soluble interleukin-2 receptor, and triglycerides, and a decrease of circulating natural killer (NK) activity.

The modified immune cells comprising a CAR of the present invention may be used in a method of treatment as described herein. In one aspect, the invention includes a method of treating cancer in a subject in need thereof, comprising administering to the subject any one of the modified immune or precursor cells disclosed herein. Yet another aspect of the invention includes a method of treating cancer in a subject in need thereof, comprising administering to the subject a modified immune or precursor cell generated by any one of the methods disclosed herein.

One aspect of the invention provides a method treating a cancer in a subject in need thereof, comprising administering to the subject an effective amount of a modified immune cell comprising a CAR capable of binding FAP, wherein the CAR comprises: a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9, wherein the cancer comprises fibroblast activation protein (FAP)-expressing cancer-associated cells.

In certain embodiments, the CAR binds to FAP-expressing cancer-associated cells and does not bind to cells that do not express FAP. In certain embodiments, the CAR binds to FAP-expressing cancer-associated cells, comprising a high level of FAP expression. In certain embodiments, the CAR does not bind to cells that do not express FAP. In certain embodiments, the CAR does not bind to cells that express a basal level of FAP, comprising a low level of FAP expression.

Another aspect of the invention provides a method of treating a cancer in a subject in need thereof, wherein the cancer is associated with fibroblast activation protein (FAP)-expressing cancer-associated fibroblasts, comprising administering to the subject an effective amount of a modified T cell comprising a chimeric antigen receptor (CAR) capable of binding FAP. The CAR comprises a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

Yet another aspect of the invention provides a method of treating a cancer in a subject in need thereof, wherein the cancer is associated with fibroblast activation protein (FAP)-expressing cancer-associated macrophages. The method comprises administering to the subject an effective amount of a modified T cell comprising a chimeric antigen receptor (CAR) capable of binding FAP, wherein the CAR comprises a heavy chain variable region comprising an amino acid sequence at least 80%, 85%, 90%, 95%, 96%, 97%, 98%, 99%, or 100% identical to SEQ ID NO: 7 and a light chain variable region comprising an amino acid sequence at least 80%, 85%, 90%, 95%, 96%, 97%, 98%, 99%, or 100% identical to SEQ ID NO: 9.

Still another aspect of the invention provides a method of treating a cancer in a subject in need thereof, wherein the cancer is associated with fibroblast activation protein (FAP)-expressing cancer-associated neutrophils. The method comprises administering to the subject an effective amount of a modified T cell comprising a chimeric antigen receptor (CAR) capable of binding FAP, wherein the CAR comprises a heavy chain variable region comprising an amino acid sequence at least 80%, 85%, 90%, 95%, 96%, 97%, 98%, 99%, or 100% identical to SEQ ID NO: 7 and a light chain variable region comprising an amino acid sequence at least 80%, 85%, 90%, 95%, 96%, 97%, 98%, 99%, or 100% identical to SEQ ID NO: 9.

Also provided is a method of treating a cancer in a subject in need thereof, wherein the cancer is associated with fibroblast activation protein (FAP)-expressing cancer-associated fibroblasts. The method comprises administering to the subject an effective amount of a modified T cell comprising a chimeric antigen receptor (CAR) capable of binding FAP, wherein the CAR comprises an amino acid sequence at least 80%, 85%, 90%, 95%, 96%, 97%, 98%, 99%, or 100% identical to SEQ ID NO: 23 or 25.

Also provided is a method of treating a cancer in a subject in need thereof, wherein the cancer is associated with fibroblast activation protein (FAP)-expressing cancer-associated macrophages. The method comprises administering to the subject an effective amount of a modified T cell comprising a chimeric antigen receptor (CAR) capable of binding FAP, wherein the CAR comprises an amino acid sequence at least 80%, 85%, 90%, 95%, 96%, 97%, 98%, 99%, or 100% identical to SEQ ID NO: 23 or 25.

Also provided is a method of treating a cancer in a subject in need thereof, wherein the cancer is associated with fibroblast activation protein (FAP)-expressing cancer-associated neutrophils. The method comprises administering to the subject an effective amount of a modified T cell comprising a chimeric antigen receptor (CAR) capable of binding FAP, wherein the CAR comprises an amino acid sequence at least 80%, 85%, 90%, 95%, 96%, 97%, 98%, 99%, or 100% identical to SEQ ID NO: 23 or 25.

Also provided is a method of treating a solid tumor in a subject in need thereof, wherein the tumor is associated with fibroblast activation protein (FAP)-expressing cancer-associated fibroblasts. The method comprises administering to the subject an effective amount of a modified T cell comprising a chimeric antigen receptor (CAR) capable of binding FAP, wherein the CAR comprises: a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

Also provided is a method of treating a solid tumor in a subject in need thereof, wherein the tumor is associated with fibroblast activation protein (FAP)-expressing cancer-associated macrophages. The method comprises administering to the subject an effective amount of a modified T cell comprising a chimeric antigen receptor (CAR) capable of binding FAP, wherein the CAR comprises: a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

Also provided is a method of treating a solid tumor in a subject in need thereof, wherein the tumor is associated with fibroblast activation protein (FAP)-expressing cancer-associated neutrophils. The method comprises administering to the subject an effective amount of a modified T cell comprising a chimeric antigen receptor (CAR) capable of binding FAP, wherein the CAR comprises: a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

In certain embodiments, the method further comprises administering an immune checkpoint inhibitor, tumor antigen vaccine, or neoplastic cell targeted therapies. Tumor antigen vaccines are made of oncogenic viral proteins, cancer cells, parts of cancer cells, or pure tumor antigens. Examples of tumor antigen vaccines include but are not limited to human papilloma viral antigens (ie. HPVE6 or HPVE7), Epstein-Barr viral proteins, oncofetal antigens (such as MAGE, NY-ESO, etc.), overexpressed tumor proteins (such as mesothelin, or Wilms tumor 1 antigen), or vaccines made against individual tumor neoantigens. Other neoplastic cell targeted therapies include but are not limited to cytotoxic chemotherapy, monoclonal antibody therapy (alone or as immunotoxins), bispecific antibodies, tyrosine kinase inhibitors, PARP inhibitors, proteasome inhibitors, immunomodulatory agents (such as lenolinamide), anti-apoptosis agents, and the like. This also includes adoptive T cell transfer using tumor targeted CAR T cells, NK cells, or modified T lymphocytes.

In certain embodiments, the subject is human. In certain embodiments, the subject is a non-human animal.

Methods of the present invention can be used to transiently ablate FAP-positive stromal cells leading to transient depletion of tumor-associated matrix and inhibit tumor growth as a monotherapy and/or have additive or synergistic anti-tumor activity given in combination with tumor cell directed therapies and immunotherapies such as vaccines. For example, combination therapy may include the use of a modified immune cell of the present disclosure in combination with other conventional therapies, such as recently developed immunotherapies such as checkpoint blockade and tumor antigen vaccination, and neoplastic cell targeted therapies.

G. Expansion of Immune Cells

Whether prior to or after modification of cells to express a CAR, the cells can be activated and expanded in number using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Publication No. 20060121005. For example, the T cells of the invention may be expanded by contact with a surface having attached thereto an agent that stimulates a CD3/TCR complex associated signal and a ligand that stimulates a co-stimulatory molecule on the surface of the T cells. In particular, T cell populations may be stimulated by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, T cells can be contacted with an anti-CD3 antibody and an anti-CD28 antibody, under conditions appropriate for stimulating proliferation of the T cells. Examples of an anti-CD28 antibody include 9.3, B-T3, XR-CD28 (Diaclone, Besancon, France) and these can be used in the invention, as can other methods and reagents known in the art (see, e.g., ten Berge et al., Transplant Proc. (1998) 30(8): 3975-3977; Haanen et al., J. Exp. Med. (1999) 190(9): 1319-1328; and Garland et al., J. Immunol. Methods (1999) 227(1-2): 53-63).

Expanding T cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. A cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more. In one embodiment, human T regulatory cells are expanded via anti-CD3 antibody coated KT64.86 artificial antigen presenting cells (aAPCs). Methods for expanding and activating T cells can be found in U.S. Pat. Nos. 7,754,482, 8,722,400, and 9,555,105, contents of which are incorporated herein in their entirety.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

H. Methods of Producing Genetically Modified Immune Cells

The present disclosure provides methods for producing or generating a modified immune cell or precursor thereof (e.g., a T cell or NK cell) of the invention for tumor immunotherapy, e.g., adoptive immunotherapy.

In some embodiments, the CAR is introduced into a cell by an expression vector.

Expression vectors comprising a nucleic acid sequence encoding a CAR of the present invention are provided herein. Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, Piggybak, and Integrases such as Phi31. Some other suitable expression vectors include Herpes simplex virus (HSV) and retrovirus expression vectors.

In certain embodiments, the nucleic acid encoding a CAR is introduced into the cell via viral transduction. In certain embodiments, the viral transduction comprises contacting the immune or precursor cell with a viral vector comprising the nucleic acid encoding a CAR. In certain embodiments, the viral vector is an adeno-associated viral (AAV) vector. In certain embodiments, the AAV vector comprises a Woodchuck Hepatitis Virus post-transcriptional regulatory element (WPRE). In certain embodiments, the AAV vector comprises a polyadenylation (polyA) sequence. In certain embodiments, the polyA sequence is a bovine growth hormone (BGH) polyA sequence.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the CAR in the host cell. In some embodiments, the adenovirus genome is a 36 kb, linear, double stranded DNA, where a foreign DNA sequence (e.g., a nucleic acid encoding a CAR) may be inserted to substitute large pieces of adenoviral DNA in order to make the expression vector of the present invention (see, e.g., Danthinne and Imperiale, Gene Therapy (2000) 7(20): 1707-1714).

Another expression vector is based on an adeno associated virus (AAV), which takes advantage of the adenovirus coupled systems. This AAV expression vector has a high frequency of integration into the host genome. It can infect nondividing cells, thus making it useful for delivery of genes into mammalian cells, for example, in tissue cultures or in vivo. The AAV vector has a broad host range for infectivity. Details concerning the generation and use of AAV vectors are described in U.S. Pat. Nos. 5,139,941 and 4,797,368.

Retrovirus expression vectors are capable of integrating into the host genome, delivering a large amount of foreign genetic material, infecting a broad spectrum of species and cell types and being packaged in special cell lines. The retroviral vector is constructed by inserting a nucleic acid (e.g., a nucleic acid encoding a CAR) into the viral genome at certain locations to produce a virus that is replication defective. Though the retroviral vectors are able to infect a broad variety of cell types, integration and stable expression of the CAR requires the division of host cells.

Lentiviral vectors are derived from lentiviruses, which are complex retroviruses that, in addition to the common retroviral genes gag, pol, and env, contain other genes with regulatory or structural function (see, e.g., U.S. Pat. Nos. 6,013,516 and 5,994,136). Some examples of lentiviruses include the Human Immunodeficiency Viruses (HIV-1, HIV-2) and the Simian Immunodeficiency Virus (SIV). Lentiviral vectors have been generated by multiply attenuating the HIV virulence genes, for example, the genes env, vif, vpr, vpu and nef are deleted making the vector biologically safe. Lentiviral vectors are capable of infecting non-dividing cells and can be used for both in vivo and ex vivo gene transfer and expression, e.g., of a nucleic acid encoding a CAR (see, e.g., U.S. Pat. No. 5,994,136).

Expression vectors including a nucleic acid of the present disclosure can be introduced into a host cell by any means known to persons skilled in the art. The expression vectors may include viral sequences for transfection, if desired. Alternatively, the expression vectors may be introduced by fusion, electroporation, biolistics, transfection, lipofection, or the like. The host cell may be grown and expanded in culture before introduction of the expression vectors, followed by the appropriate treatment for introduction and integration of the vectors. The host cells are then expanded and may be screened by virtue of a marker present in the vectors. Various markers that may be used are known in the art, and may include hprt, neomycin resistance, thymidine kinase, hygromycin resistance, etc. As used herein, the terms "cell," "cell line," and "cell culture" may be used interchangeably. In some embodiments, the host cell an immune cell or precursor thereof, e.g., a T cell, an NK cell, or an NKT cell.

The present invention also provides genetically engineered cells which include and stably express a CAR of the present disclosure. In some embodiments, the genetically engineered cells are genetically engineered T-lymphocytes (T cells), naive T cells (TN), memory T cells (for example, central memory T cells (TCM), effector memory cells (TEM)), natural killer cells (NK cells), and macrophages capable of giving rise to therapeutically relevant progeny. In certain embodiments, the genetically engineered cells are autologous cells. In certain embodiments, the modified cell is resistant to T cell exhaustion.

Modified cells (e.g., comprising a CAR) may be produced by stably transfecting host cells with an expression vector including a nucleic acid of the present disclosure. Additional methods for generating a modified cell of the present disclosure include, without limitation, chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells expressing a CAR of the present disclosure may be expanded ex vivo.

Physical methods for introducing an expression vector into host cells include calcium phosphate precipitation, lipofection, particle bombardment, microinjection, electroporation, and the like. Methods for producing cells including vectors and/or exogenous nucleic acids are well-known in the art. See, e.g., Sambrook et al. (2001), Molecular Cloning: A Laboratory Manual, Cold Spring Harbor Laboratory, New York. Chemical methods for introducing an expression vector into a host cell include colloidal dispersion systems, such as macromolecule complexes, nanocapsules, microspheres, beads, and lipid-based systems including oil-in-water emulsions, micelles, mixed micelles, and liposomes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform may be used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). Compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, molecular biology assays well known to those of skill in the art, such as Southern and Northern blotting, RT-PCR and PCR; biochemistry assays, such as detecting the presence or absence of a particular peptide, e.g., by immunological means (ELISAs and Western blots) or by assays described herein to identify agents falling within the scope of the invention.

In one embodiment, the nucleic acids introduced into the host cell are RNA. In another embodiment, the RNA is mRNA. For example, in certain embodiments, the nucleic acid encoding the CAR is an mRNA and the mRNA is introduced (e.g. transduced) into the host cell. In another embodiment, the RNA is mRNA that comprises in vitro transcribed RNA or synthetic RNA. The RNA may be produced by in vitro transcription using a polymerase chain reaction (PCR)-generated template. DNA of interest from any source can be directly converted by PCR into a template for in vitro mRNA synthesis using appropriate primers and RNA polymerase. The source of the DNA may be, for example, genomic DNA, plasmid DNA, phage DNA, cDNA, synthetic DNA sequence or any other appropriate source of DNA.

PCR may be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers may also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

In some embodiments, the RNA is electroporated into the cells, such as in vitro transcribed RNA. Any solutes suitable for cell electroporation, which can contain factors facilitating cellular permeability and viability such as sugars, peptides, lipids, proteins, antioxidants, and surfactants can be included.

In some embodiments, a nucleic acid encoding a CAR of the present disclosure will be RNA, e.g., in vitro synthesized RNA. Methods for in vitro synthesis of RNA are known in the art; any known method can be used to synthesize RNA comprising a sequence encoding a CAR. Methods for introducing RNA into a host cell are known in the art. See, e.g., Zhao et al. Cancer Res. (2010) 15: 9053. Introducing RNA comprising a nucleotide sequence encoding a CAR into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding a CAR.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. An RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171, 264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

I. Pharmaceutical Compositions and Formulations

Also provided are pharmaceutical compositions comprising a therapeutically effective amount of the modified cells disclosed herein. Among the compositions are pharmaceutical compositions and formulations for administration, such as for adoptive cell therapy. Also provided are therapeutic methods for administering the cells and compositions to subjects, e.g., patients.

Also provided are compositions including the cells for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

J. Embodiments of the Disclosure

In certain aspects, the invention provides a chimeric antigen receptor (CAR) comprising an antigen-binding domain capable of binding Fibroblast Activation Protein (FAP), a transmembrane domain, and an intracellular domain, wherein the antigen-binding domain comprises a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), a LCDR2 comprises the amino acid sequence LTSNLA (SEQ ID NO: 5), and LCDR3 comprises the amino acid sequence QQWSGYPPIT (SEQ ID NO: 6).

In certain embodiments, the antigen-binding domain comprises a heavy chain variable region comprising an amino acid sequence at least 80%, 85%, 90%, 95%, 96%, 97%, 98%, 99%, or 100% identical to SEQ ID NO: 7. In certain embodiments, the antigen-binding domain comprises a light chain variable region comprising an amino acid sequence at least 80%, 85%, 90%, 95%, 96%, 97%, 98%, 99%, or 100% identical to SEQ ID NO: 9. In certain embodiments, the antigen-binding domain comprises a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

In certain embodiments, the antigen-binding domain is selected from the group consisting of a full-length antibody or antigen-binding fragment thereof, a Fab, a single-chain variable fragment (scFv), or a single-domain antibody.

In certain embodiments, the antigen-binding domain is a single-chain variable fragment (scFv) comprising an amino acid sequence at least 80%, 85%, 90%, 95%, 96%, 97%, 98%, 99%, or 100% identical to SEQ ID NO: 11 or 13.

In certain embodiments, the CAR is capable of binding to fibroblast activation protein (FAP). In certain embodiments, the CAR is capable of binding human FAP. In certain embodiments, the CAR is capable of binding canine FAP. In certain embodiments, the CAR is capable of binding murine FAP. In certain embodiments, the CAR is capable of binding human, canine, and murine FAP.

In certain embodiments, the CAR further comprises a hinge domain. In certain embodiments, the hinge domain comprises a hinge domain of CD8 alpha.

In certain embodiments, the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), ICOS (CD278), and CD154, or a transmembrane domain derived from a killer immunoglobulin-like receptor (KIR). In certain embodiments, the transmembrane domain comprises a transmembrane domain of CD8. In certain embodiments, the transmembrane domain comprises a transmembrane domain of CD8 alpha. In certain embodiments, the transmembrane domain comprises a transmembrane domain derived from a killer immunoglobulin-like receptor (KIR).

In certain embodiments, the intracellular domain comprises a costimulatory signaling domain and an intracellular signaling domain. In certain embodiments, the intracellular domain comprises one or more of a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS (CD278), NKG2C, and B7-H3 (CD276), or a variant thereof, or an intracellular domain derived from a killer immunoglobulin-like receptor (KIR). In certain embodiments, the intracellular domain comprises a costimulatory domain of 4-1BB. In certain embodiments, the intracellular domain comprises a costimulatory domain of DAP12. In certain embodiments, the intracellular domain comprises a costimulatory domain of CD28. In certain embodiments, the intracellular domain comprises a costimulatory domain of 4-1BB and a costimulatory domain of CD28. In certain embodiments, the intracellular domain comprises a costimulatory domain of DAP12 and a costimulatory domain of CD28.

In certain embodiments, the intracellular signaling domain comprises an intracellular domain selected from the group consisting of cytoplasmic signaling domains of a human CD3 zeta chain (CD3ζ), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In certain embodiments, the intracellular signaling domain comprises an intracellular domain of CD3ζ.

In another aspect, the invention provides a chimeric antigen receptor (CAR) capable of binding FAP, comprising an antigen-binding domain, a transmembrane domain, and an intracellular domain, wherein the antigen-binding domain comprises a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

In certain embodiments, the antigen-binding domain comprises a single-chain variable fragment (scFv). In certain embodiments, the scFv comprises from N-terminus to C-terminus: the heavy chain variable region, a linker, and the light chain variable region. In certain embodiments, the scFv is comprises from N-terminus to C-terminus: the light chain variable region, a linker, and the heavy chain variable region. In certain embodiments, the linker comprises SEQ ID NO: 15.

In another aspect, the invention provides a chimeric antigen receptor (CAR) capable of binding FAP, comprising an antigen-binding domain comprising an amino acid sequence at least 80%, 85%, 90%, 95%, 96%, 97%, 98%, 99%, or 100% identical to SEQ ID NO: 11 or 13.

In another aspect, the invention provides a chimeric antigen receptor (CAR) capable of binding Fibroblast Activation Protein (FAP), comprising an amino acid sequence at least 80%, 85%, 90%, 95%, 96%, 97%, 98%, 99%, or 100% identical to SEQ ID NO: 23 or 25.

In another aspect, the invention provides a nucleic acid comprising a polynucleotide sequence encoding any of the CARs contemplated herein.

In another aspect, the invention provides a nucleic acid comprising a polynucleotide sequence encoding a chimeric antigen receptor (CAR) capable of binding FAP, comprising an antigen-binding domain, a transmembrane domain, and an intracellular domain, wherein the antigen-binding domain comprises a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), LCDR2 comprises the amino acid sequence LTSNLA (SEQ ID NO: 5), and LCDR3 comprises the amino acid sequence QQWSGYPPIT (SEQ ID NO: 6).

In certain embodiments, the antigen-binding domain comprises a heavy chain variable region encoded by a polynucleotide sequence at least 80%, 85%, 90%, 95%, 96%, 97%, 98%, 99%, or 100% identical to SEQ ID NO: 8. In certain embodiments, the antigen-binding domain comprises a light chain variable region encoded by a polynucleotide sequence at least 80%, 85%, 90%, 95%, 96%, 97%, 98%, 99%, or 100% identical to SEQ ID NO: 10. In certain embodiments, the antigen-binding domain comprises a heavy chain variable region encoded by a polynucleotide sequence at least 80%, 85%, 90%, 95%, 96%, 97%, 98%, 99%, or 100% identical to SEQ ID NO: 8; and a light chain variable region encoded by a polynucleotide sequence at least 80%, 85%, 90%, 95%, 96%, 97%, 98%, 99%, or 100% identical to SEQ ID NO: 10.

In certain embodiments, the antigen-binding domain comprises a single-chain variable fragment (scFv) encoded by a polynucleotide sequence at least 80%, 85%, 90%, 95%, 96%, 97%, 98%, 99%, or 100% identical to SEQ ID NO: 12 or 14.

In certain embodiments, the transmembrane domain comprises a transmembrane domain of CD8 alpha.

In certain embodiments, the intracellular domain comprises a costimulatory signaling domain and an intracellular signaling domain. In certain embodiments, the costimulatory signaling domain comprises a costimulatory domain of 4-1BB. In certain embodiments, the intracellular domain comprises a costimulatory domain of DAP12. In certain embodiments, the intracellular domain comprises a costimulatory domain of CD28. In certain embodiments, the intracellular domain comprises a costimulatory domain of 4-1BB and a costimulatory domain of CD28. In certain embodiments, the intracellular domain comprises a costimulatory domain of DAP12 and a costimulatory domain of CD28. In certain embodiments, the intracellular signaling domain comprises an intracellular domain of CD3ζ.

In another aspect, the invention provides a nucleic acid comprising a polynucleotide sequence encoding a chimeric antigen receptor (CAR) capable of binding fibroblast activation protein (FAP), comprising an antigen-binding domain, a transmembrane domain, and an intracellular domain, wherein the antigen-binding domain comprises a heavy chain variable region encoded by a polynucleotide sequence at least 80%, 85%, 90%, 95%, 96%, 97%, 98%, 99%, or 100% identical to SEQ ID NO: 8; and a light chain variable region encoded by a polynucleotide sequence at least 80%, 85%, 90%, 95%, 96%, 97%, 98%, 99%, or 100% identical to SEQ ID NO: 10.

In another aspect, the invention provides a nucleic acid comprising a polynucleotide sequence at least 80%, 85%, 90%, 95%, 96%, 97%, 98%, 99%, or 100% identical to SEQ ID NO: 22 or 24.

In another aspect, the invention provides a vector comprising any of the nucleic acids contemplated herein. In certain embodiments, the vector is an expression vector. In certain embodiments, the vector is selected from the group consisting of a DNA vector, an RNA vector, a plasmid, a lentiviral vector, an adenoviral vector, an adeno-associated viral vector, and a retroviral vector.

In another aspect, the invention provides a modified immune cell of precursor cell thereof, comprising any of the CARs contemplated herein, any of the nucleic acids contemplated herein, or any of the vectors contemplated herein.

In another aspect, the invention provides a modified immune cell or precursor cell thereof, comprising a chimeric antigen receptor (CAR) capable of binding fibroblast activation protein (FAP), wherein the CAR comprises a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and a light chain variable region that comprises three light chain complementarity determining regions (LCDRs), wherein LCDR1 comprises the amino acid sequence TASSSVSYMY (SEQ ID NO: 4), a LCDR2 comprises the amino acid sequence LTSNLA (SEQ ID NO: 5), and LCDR3 comprises the amino acid sequence QQWSGYPPIT (SEQ ID NO: 6).

In another aspect, the invention provides a modified immune cell of precursor cell thereof, comprising a chimeric antigen receptor (CAR) capable of binding fibroblast activation protein (FAP), wherein the CAR comprises a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

In another aspect, the invention provides a modified immune cell or precursor cell thereof, comprising a chimeric antigen receptor (CAR) capable of binding fibroblast activation protein (FAP), wherein the CAR comprises a single-chain variable fragment (scFv) comprising an amino acid sequence at least 80%, 85%, 90%, 95%, 96%, 97%, 98%, 99%, or 100% identical to SEQ ID NO: 11 or 13.

In another aspect, the invention provides a modified immune cell or precursor cell thereof, comprising a chimeric antigen receptor (CAR) capable of binding fibroblast activation protein (FAP), wherein the CAR comprises an amino acid sequence at least 80%, 85%, 90%, 95%, 96%, 97%, 98%, 99%, or 100% identical to SEQ ID NO: 23 or 25.

In certain embodiments, the CAR is capable of binding FAP. In certain embodiments, the CAR is capable of binding human FAP. In certain embodiments, the CAR is capable of binding canine FAP. In certain embodiments, the CAR is capable of binding mouse FAP. In certain embodiments, the CAR is capable of binding human, canine, and mouse FAP.

In certain embodiments, the modified cell is a modified T cell. In certain embodiments, the modified cell is a modified NK cell. In certain embodiments, the modified cell is an autologous cell. In certain embodiments, the modified cell is an autologous cell obtained from a human subject. In certain embodiments, the modified cell is an autologous cell obtained from a canine subject. In certain embodiments, the modified cell is an allogeneic cell.

In another aspect, the invention provides a pharmaceutical composition comprising a therapeutically effective amount of any of the modified cells contemplated herein, and a pharmaceutically acceptable excipient.

In another aspect, the invention provides a method of treating a disease in a subject in need thereof, comprising administering to the subject an effective amount of any of the modified cells, or any of the pharmaceutical compositions contemplated herein.

In certain embodiments, the disease is selected from the group consisting of an immunological disease, a hematological disease, an autoimmune disease, fibrosis, and cancer. In certain embodiments, the disease is cancer. In certain embodiments, the disease is cardiac fibrosis.

In certain embodiments, the cancer comprises a FAP-expressing cancer-associated cell. In certain embodiments, the FAP-expressing cancer-associated cell is a cancer-associated fibroblast (CAF). In certain embodiments, the FAP-expressing cancer-associated cell is a FAP-expressing adipocyte. In certain embodiments, the FAP-expressing cancer-associated cell is a tumor-associated macrophage (TAM). In certain embodiments, the FAP-expressing cancer-associated cell is a tumor-associated neutrophil (TAN). In certain embodiments, the FAP-expressing cancer-associated cell is a myeloid-derived suppressor cell (MDSC). In certain embodiments, the FAP-expressing cancer-associated cell is a cancer-initiating cell.

In another aspect, the invention provides a method of treating a cancer in a subject in need thereof, comprising administering to the subject an effective amount of a modified immune cell comprising a chimeric antigen receptor (CAR) capable of binding FAP, wherein the CAR comprises a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9; wherein the cancer comprises fibroblast activation protein (FAP)-expressing cancer-associated cells. In certain embodiments, the CAR binds to FAP-expressing cancer-associated cells and does not bind to cells that do not express FAP.

In another aspect, the invention provides a method of treating a cancer in a subject in need thereof, wherein the cancer is associated with fibroblast activation protein (FAP)-expressing cancer-associated fibroblasts, comprising administering to the subject an effective amount of a modified T cell comprising a chimeric antigen receptor (CAR) capable of binding FAP, wherein the CAR comprises a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

In another aspect, the invention provides a method of treating a cancer in a subject in need thereof, wherein the cancer is associated with fibroblast activation protein (FAP)-expressing cancer-associated macrophages, comprising administering to the subject an effective amount of a modified T cell comprising a chimeric antigen receptor (CAR) capable of binding FAP, wherein the CAR comprises a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

In another aspect, the invention provides a method of treating a cancer in a subject in need thereof, wherein the cancer is associated with fibroblast activation protein (FAP)-expressing cancer-associated neutrophils, comprising administering to the subject an effective amount of a modified T cell comprising a chimeric antigen receptor (CAR) capable of binding FAP, wherein the CAR comprises a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

In another aspect, the invention provides a method of treating a cancer in a subject in need thereof, wherein the cancer is associated with fibroblast activation protein (FAP)-expressing cancer-associated fibroblasts, comprising administering to the subject an effective amount of a modified T cell comprising a chimeric antigen receptor (CAR) capable of binding FAP, wherein the CAR comprises an amino acid sequence at least 80%, 85%, 90%, 95%, 96%, 97%, 98%, 99%, or 100% identical to SEQ ID NO: 23 or 25.

In another aspect, the invention provides a method of treating a cancer in a subject in need thereof, wherein the cancer is associated with fibroblast activation protein (FAP)-expressing cancer-associated macrophages, comprising administering to the subject an effective amount of a modified T cell comprising a chimeric antigen receptor (CAR) capable of binding FAP, wherein the CAR comprises an amino acid sequence at least 80%, 85%, 90%, 95%, 96%, 97%, 98%, 99%, or 100% identical to SEQ ID NO: 23 or 25.

In another aspect, the invention provides a method of treating a cancer in a subject in need thereof, wherein the cancer is associated with fibroblast activation protein (FAP)-expressing cancer-associated neutrophils, comprising administering to the subject an effective amount of a modified T cell comprising a chimeric antigen receptor (CAR) capable of binding FAP, wherein the CAR comprises an amino acid sequence at least 80%, 85%, 90%, 95%, 96%, 97%, 98%, 99%, or 100% identical to SEQ ID NO: 23 or 25.

In another aspect, the invention provides a method of treating a solid tumor in a subject in need thereof, wherein the tumor is associated with fibroblast activation protein (FAP)-expressing cancer-associated fibroblasts, comprising administering to the subject an effective amount of a modified T cell comprising a chimeric antigen receptor (CAR) capable of binding FAP, wherein the CAR comprises a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

In another aspect, the invention provides a method of treating a solid tumor in a subject in need thereof, wherein the tumor is associated with fibroblast activation protein (FAP)-expressing cancer-associated macrophages, comprising administering to the subject an effective amount of a modified T cell comprising a chimeric antigen receptor (CAR) capable of binding FAP, wherein the CAR comprises a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

In another aspect, the invention provides a method of treating a solid tumor in a subject in need thereof, wherein the tumor is associated with fibroblast activation protein (FAP)-expressing cancer-associated neutrophils, comprising administering to the subject an effective amount of a modified T cell comprising a chimeric antigen receptor (CAR) capable of binding FAP, wherein the CAR comprises a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 9.

In certain embodiments, the method further comprises administering an immune checkpoint inhibitor, tumor antigen vaccine, or neoplastic cell targeted therapies.

In certain embodiments, the subject is human. In certain embodiments, the subject is a non-human animal.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Materials and Methods used in the performance of the experiments disclosed herein are now described.

Bioinformatic Deduction of the Canine FAP Gene Sequence:

PCR primers were designed using the NCBI predicted sequence for canine FAP (XM_005640252.2). The resulting PCR product matches the predicted sequence 100% at the protein level. There are two conservative base pair substitutions at T127 and A603 at the nucleotide level.

Canine FAP cDNA PCR, Sub-Cloning, and Expression:

Confluent 10 cm dishes of endogenous FAP expressing canine SK osteosarcoma cells were treated with 1 ml TRIzol (Life Technologies, #15596-026) and total RNA was extracted as per the manufacturer protocol. Using the SuperScript First Strand Synthesis Kit (Life Technologies, #11904-018) cDNA was reverse transcribed from 5 µg of total RNA. This cDNA was used as a template for touchdown PCR with the following primers: forward 5' ATGTAGACGTGGTTAAAAATTG (SEQ ID NO: 54); reverse 5' CGTCATCTTCAGTCGGACAA (SEQ ID NO: 55). The 2291 bp amplicon was detected on a 1% agarose gel.

The resulting PCR product was purified and cloned into pGEM-T Easy (Promega) and sequenced. This shuttle vector is linearized and contains single "T" overhangs. This allows for simple non-directional cloning of the PCR product by making use of the 3' "A" overhang added to the PCR product by Taq polymerase. From here, the cDNA was cloned into plasmid pcDNA3.1 non-directionally using the EcoRI cloning site.

Canine FAP cDNA was subcloned into lentiviral plasmid (pLenti6/v5-D-TOPO) from pcDNA3.1 using SpeI to excise the cDNA and using XbaI to open pLenti6/v5-D-TOPO. These restriction sites have compatible ends. This resulted in CanineFAP.pLenti6/v5-D-TOPO.

CanineFAP.pLenti/v5-D-TOPO was co-transfected with packaging plasmids (pMD2.G, pCMVΔR8.2) into HEK 293 cells. Virus-containing supernatant was harvested 48 hours later. The viral titer was determined by p24 ELISA and Balb/C 3T3 fibroblasts were transduced at different MOI's ranging from 0.5:1 to 10:1.

Expression of the transgene in Balb/C 3T3.canine FAP cells was confirmed using flow cytometry. The primary antibody used was biotinylated sheep anti-huFAP polyclonal antibody (5 µg/ml) from R&D systems. The secondary was APC-Streptavidin (1 µg/ml) from Biolegend.

Immunization and Hybridoma Generation:

BALB/c 3T3 cells expressing full-length canine FAP were used to immunize 14 week old BALB/c.FAP$^{-/-}$ mice. All injections were given intraperitoneally and consisted of $1 \times 10^7$ cells in 0.5 ml sterile PBS. An initial immunization was followed by boosts on days 14 and 28; animals were then bled on day 42 followed a boost on day 56, bleeding on day 63, and three more boosts on days 70, 217, and 238. On day 241, 2017 spleens were harvested, a single cell suspension prepared, and splenocytes fused with sp2/0 cells by the UPENN Hybridoma Core Facility. Hybridoma supernatant were initially screened by FACS on MC KOSA parental (FAP null) vs. canine FAP-transgene expressing MC KOSA.K9FAP using hybridoma supernatants as the primary antibodies and AF488 goat anti-mouse IgG as a secondary. Clone 4G5 was identified as reactive to transduced cells but not parental cells and screened on additional cells to confirm reactivity with FAP expressing but not FAP-negative cells: Human primary fibroblasts, BALB/c 3T3 expressing murine or human FAP transgenes, canine primary fibroblasts, SK KOSA (FAP expressing), and BALB/c 3T3 (FAP negative) cells. 4G5 was then determined to be an IgG1k isotype antibody using Thermo Fisher Rapid ELISA Mouse mAb Isotyping Kit #37503.

Generation of 4G5 Chimeric Antigen Receptors:

Total RNA isolated from 4G5 hybridoma cell line was reverse transcribed into cDNAs and PCR amplified using a library of mouse variable chain primers to identify hybridoma sequence. 5' RACE was used as an alternative approach to obtain sequence of the unique monoclonal 4G5 antibody sequence. Amplified bands were Topo cloned and sequences determined. These procedures were repeated to confirm integrity of isolated sequences. All isolated and sequence verified ORFs of variable chains were synthesized and used in heavy and light chain combinations to obtain desired scFV in CAR format.

High Titer Lentiviral Vector Production:

Packaging of each plasmid into lentivirus was done in 293T human embryonic kidney cells cultured in RPMI 1640, 10% non-heat-inactivated FBS, 2 mM glutamine, 10 mM HEPEs, 100 IU/ml penicillin and 100 µg/ml streptomycin. Cells were seeded at $12 \times 10^6$ per T 175 tissue culture flask, 24 hour prior transfection with 7 µg of pCIVSVg, 18 µg of pRSV-Rev, 18 µg of pGAG/POL and 15 µg of the plasmid of interest (4G5 CAR). Supernatant containing the virus was collected at 24 and 48 hours post-transfection and virus was 300-fold concentrated by centrifugation at 15,000 g at 4° C. overnight and cryopreserved until use. Virus titer was assessed by transducing Sup-T1 cells (cultured in RPMI+ 10% FBS+P/S) at different dilutions of the virus, and 48 hours post-transfection, cells were stained using F(ab')$_2$ fragment antibody to detect the CAR construct on the cell surface by flow cytometry.

T Cell Transduction:

Primary human CD4+ and CD8+ T cells were isolated by negative selection from healthy volunteer donors after leukapheresis. Primary CD4+ and CD8+ T cells were cultured at a 1:1 ratio with magnetic beads coated with anti-CD3/anti-CD28 at a 1:3 T cell to bead ratio without the addition of exogenous IL-2. Approximately 24 hours later, T cells were transduced with lentiviral vectors at an MOI of approximately 5. A Multisizer 3 Coulter Counter was used to monitor cell counts and cell size for 12-15 days. Cells were fed as needed with complete RPMI until resting phase, and then used either for killing assays or cryopreserved.

In Vitro Killing Assays:

Target cells were seeded at 3,000-10,000 cells/well 24 hours previous to the addition of the CAR T cells in triplicates. CAR T cells were added to the culture at different effector to target ratios considering live CAR positive T cells, which were determined by flow cytometric analysis by staining with Blue live/dead and F(ab')$_2$ fragment antibody. Co-cultures continued for 24 hours, supernatants were harvested and analyzed for IFN-γ and GranzymeB production by ELISA, and percentage of live cells per well was determined. For luciferase-expressing target cells, the wells were first washed well. The remaining cells were lysed and luciferase activity was determined by using the Luciferase Assay System on a GloMax Multi Detection System. For unlabeled cells, MTS reagent was added to the wells for 1-4 hours. The wells were washed and absorbance was read at 490 nm. CAR T cell mediated cytotoxicity was determined as the percentage of signal of the target cells without T cells.

In Vivo Studies:

Human adenocarcinoma A549 cells were injected into NSG mice. After 14 days, when tumors were ~150 mm$^3$ in size, some tumors were harvested, dissociated into single-cell suspensions, and assayed for the expression of FAP on tumor-associated fibroblasts by flow cytometry. Cells were gated first on CD45 negative cells, and then on CD90+/FAP+ cells. At this time, ~20 million total T cells were injected IV into the remaining tumor-bearing mice. Analysis of CAR T cells prior to injection showed about 50% transduction efficiency. Groups included: 1) injection with PBS only, 2) injection with 20 million non-transduced activated T cells, 3) injection with 10 million 73.3 CART cells, 3) injection with 10 million HGL2 CARTs, and 4) injection with 10 million L2HG CARTs. Tumor growth was then followed over the next 12 days.

Figure 1:
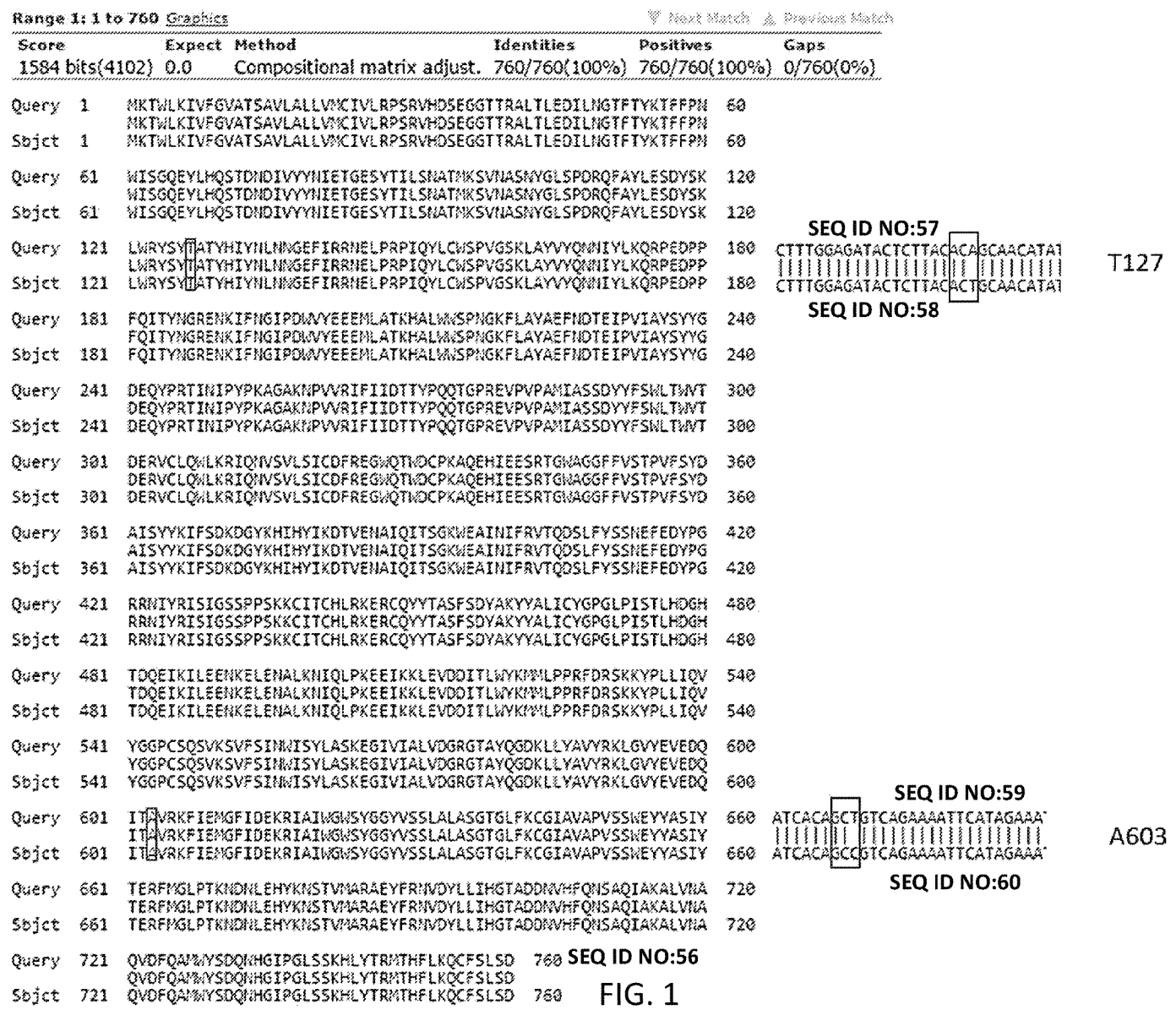

Example 1: Bioinformatic Deduction of Canine FAP Gene Sequence Used to Design PCR Primers The canine FAP gene was amplified via PCR and the sequence compared to that of canine FAP. PCR primers specific for canine FAP were designed using the NCBI predicted sequence for canine FAP (XM_005640252.2). The resulting PCR product matched the sequence of canine FAP 100% at the protein level (FIG. 1). Subsequent sequencing revealed canine FAP to possess two conservative base pair substitutions at T127 and A603 at the nucleotide level.

Example 2: Canine FAP cDNA PCR, Subcloning, Sequencing and Expression

As a first step toward generating an anti-canine FAP antibody, a construct capable of generating recombinant canine FAP protein was created. To provide canine FAP cDNA, endogenous FAP expressing canine SK osteosarcoma cells were subjected to TRIzol-based RNA extraction followed by reverse transcription of the isolated RNA into cDNA. This cDNA was used as a template for touchdown PCR, which resulted in a 2291 bp amplicon. The amplified PCR product was purified and cloned into a shuttle vector, which allowed for simple non-directional cloning of the PCR product. From here, the cDNA was cloned into a eukaryotic expression plasmid. Canine FAP cDNA was sub-cloned into a lentiviral plasmid to allow for transduction into mammalian cell lines. The resulting canine FAP-lentivirus construct was co-transfected with packaging plasmids into HEK 293 cells. Virus-containing supernatant was harvested 48 hours later. The viral titer was determined by p24 ELISA and BALB/c-derived 3T3 fibroblast cells were transduced at various MOIs ranging from 0.5:1 to 10:1. Expression of the transgene in 3T3-canine FAP cells was confirmed using flow cytometry (FIG. 2).

Example 3: Creation of Clone 4G5 Anti-FAP Antibodies

Figure 3:
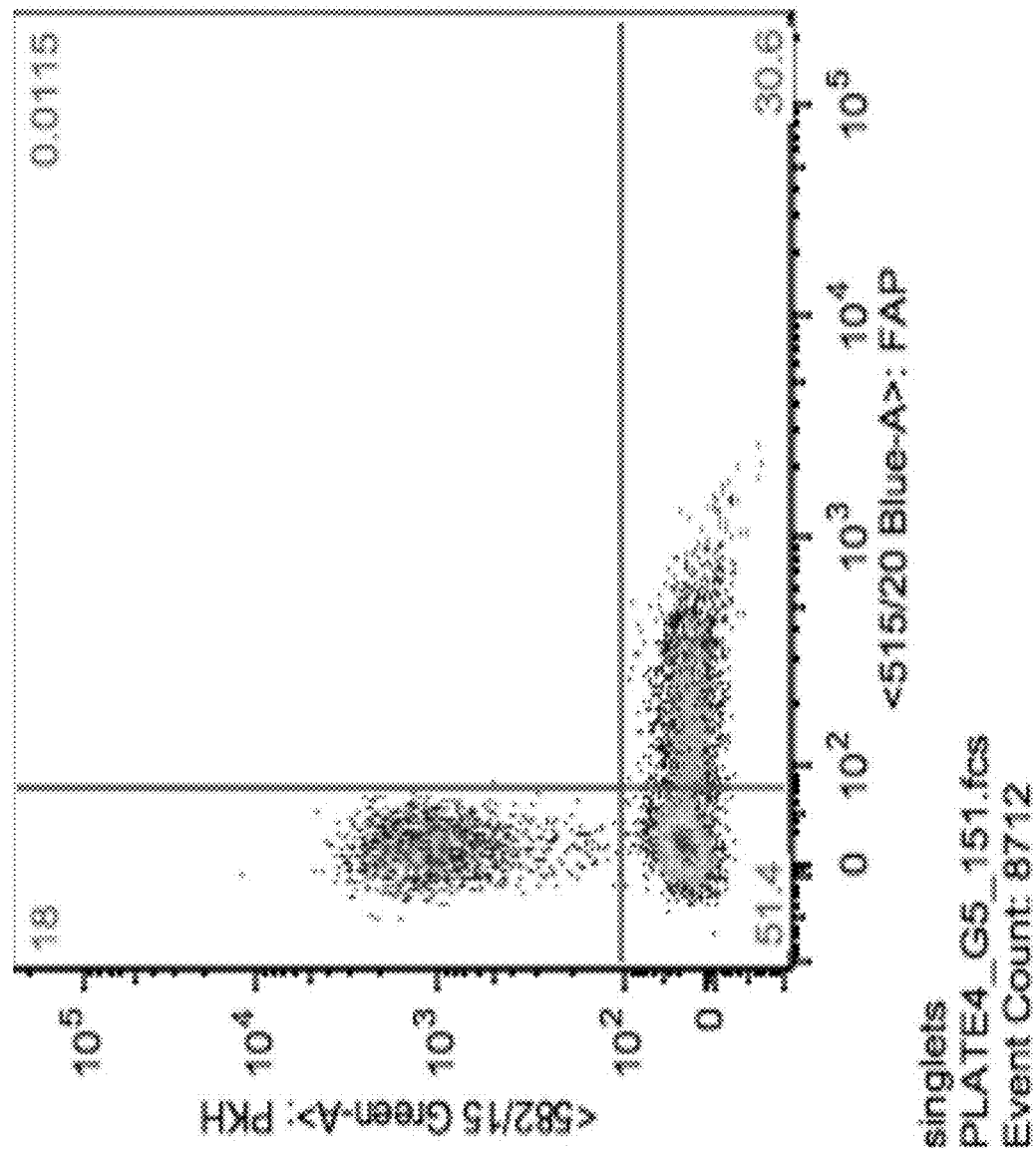
FIG. 3 is a flow cytometry plot demonstrating the generation of clone 4G5 anti-FAP antibody producing hybridoma cells. Canine FAP-transduced BALB/c 3T3 cells were used to immunize 14 week old BALB/c mice. Splenocytes were then fused to sp2/0 cells and the resulting hybridomas screened against PKH-labeled MC KOSA parental (FAP null) and canine FAP-transgene expressing MC KOSA.K9FAP cells. Primary staining was provided by hybridoma-produced antibody. Secondary staining was performed using a goat anti-mouse IgG secondary antibody followed by read-out via flow cytometry.

BALB/c 3T3 fibroblast cells transduced to express full-length canine FAP were used to immunize 14 week old BALB/c FAP$^{-/-}$ mice. All injections were given intraperitoneally and consisted of 1×10$^7$ cells in 0.5 ml sterile PBS. The initial immunization was followed by six booster immunizations at regular intervals over the next eight months. At the conclusion of the study, spleens were harvested, and the resulting single-cell suspensions were used to generate hybridomas via fusion with sp2/0 cells. The resulting hybridomas were screened for those producing anti-canine FAP antibody. As an initial screen, cells producing immunoglobulin capable of staining canine-FAP transgene-expressing MC KOSA cells, but not FAP null MC KOSA parental cells were identified by flow cytometry (FIG. 3). As a result, the 4G5 clone was identified as a potential candidate. Follow-up studies further revealed that immunoglobulin produced by the clone was able to stain FAP-expressing human primary fibroblasts, BALB/c 3T3 cells expressing murine or human FAP transgenes, canine primary fibroblasts, and FAP-expressing SK KOSA cells. Similarly, 4G5 immunoglobulin was unable to stain FAP-negative parental BALB/c 3T3 cells, further indicating its specificity. Lastly, a commercial ELISA-based antibody isotyping kit was used to characterize the immunoglobulin produced by 4G5 as a mouse-IgG1-kappa isotype antibody. Follow-up protein gels comparing 4G5 to a mouse IgG1 isotype control confirmed this observation.

Example 4: Generation of 4G5 Chimeric Antigen Receptors (CARs)

Total RNA isolated from the 4G5 hybridoma cell line was reverse transcribed into cDNA and PCR amplified using a library of mouse variable chain primers to identify the hybridoma sequence. 5' RACE was used as an alternative approach to obtain the sequence of the unique monoclonal 4G5 antibody sequence. Amplified bands were Topo cloned and sequences determined. These procedures were repeated to confirm integrity of isolated sequences. All isolated and sequence verified ORFs of variable chains were synthesized and used in heavy and light chain combinations to obtain the desired scFV in CAR format.

Figure 4A:
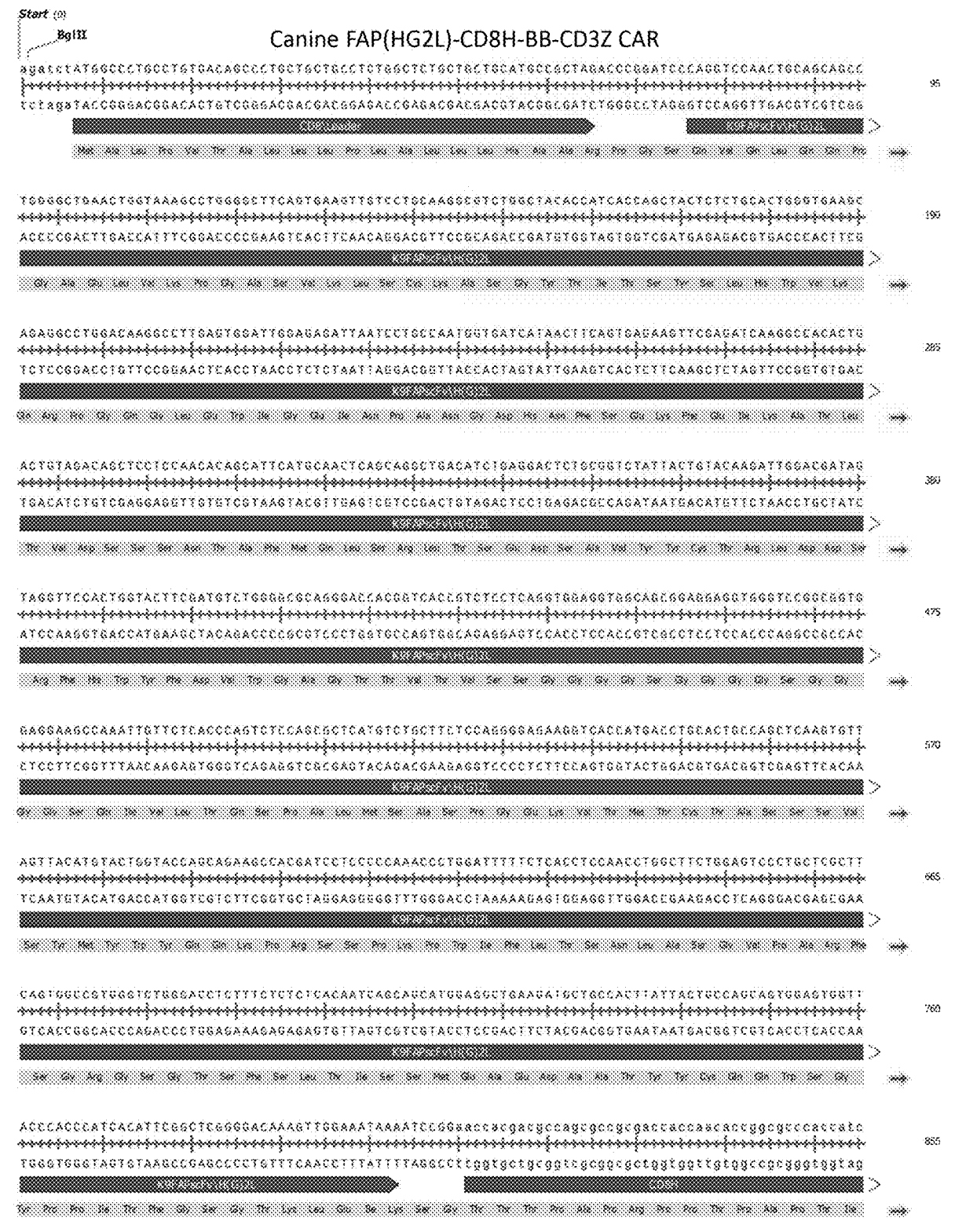
Figure 4B:
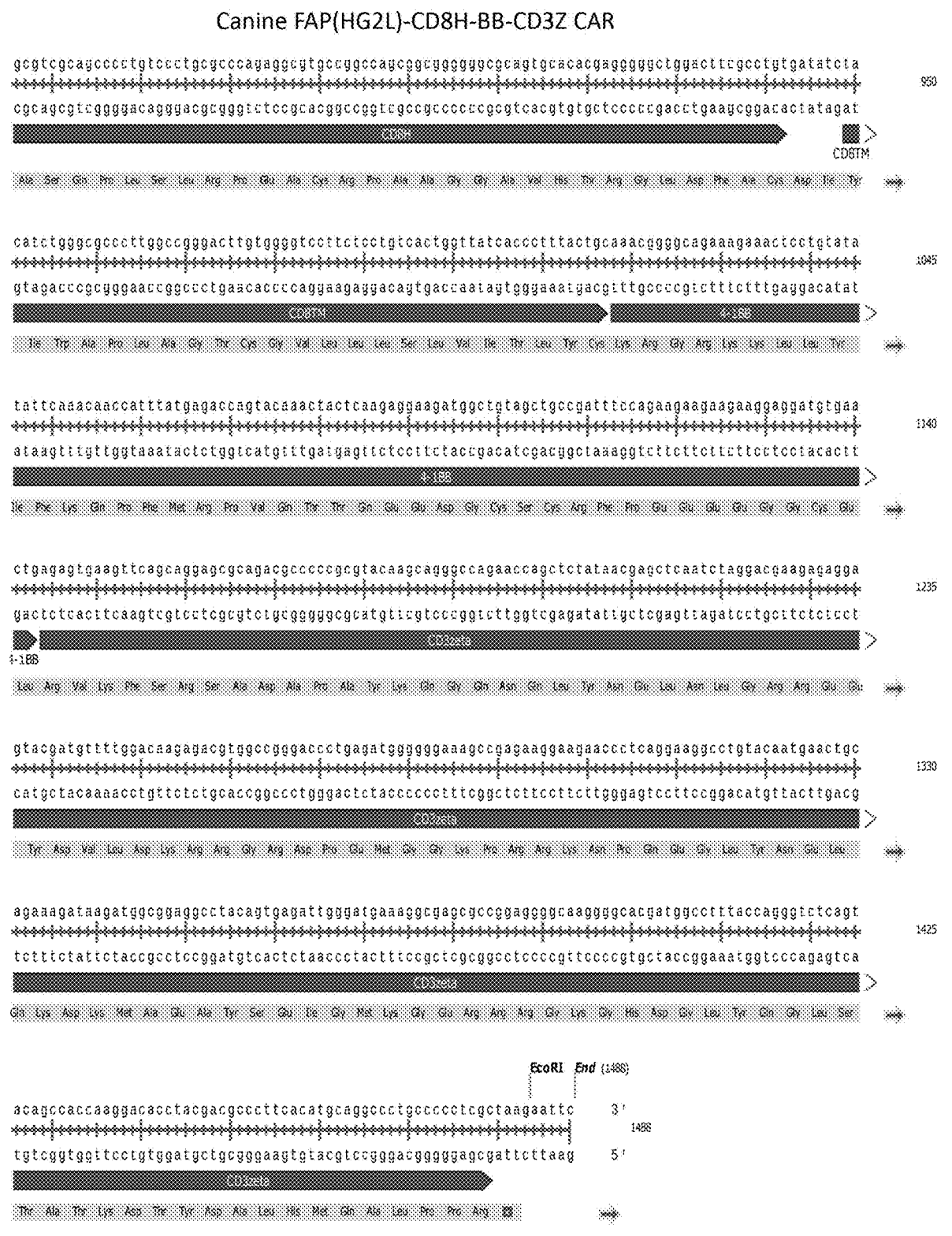
Figure 5A:
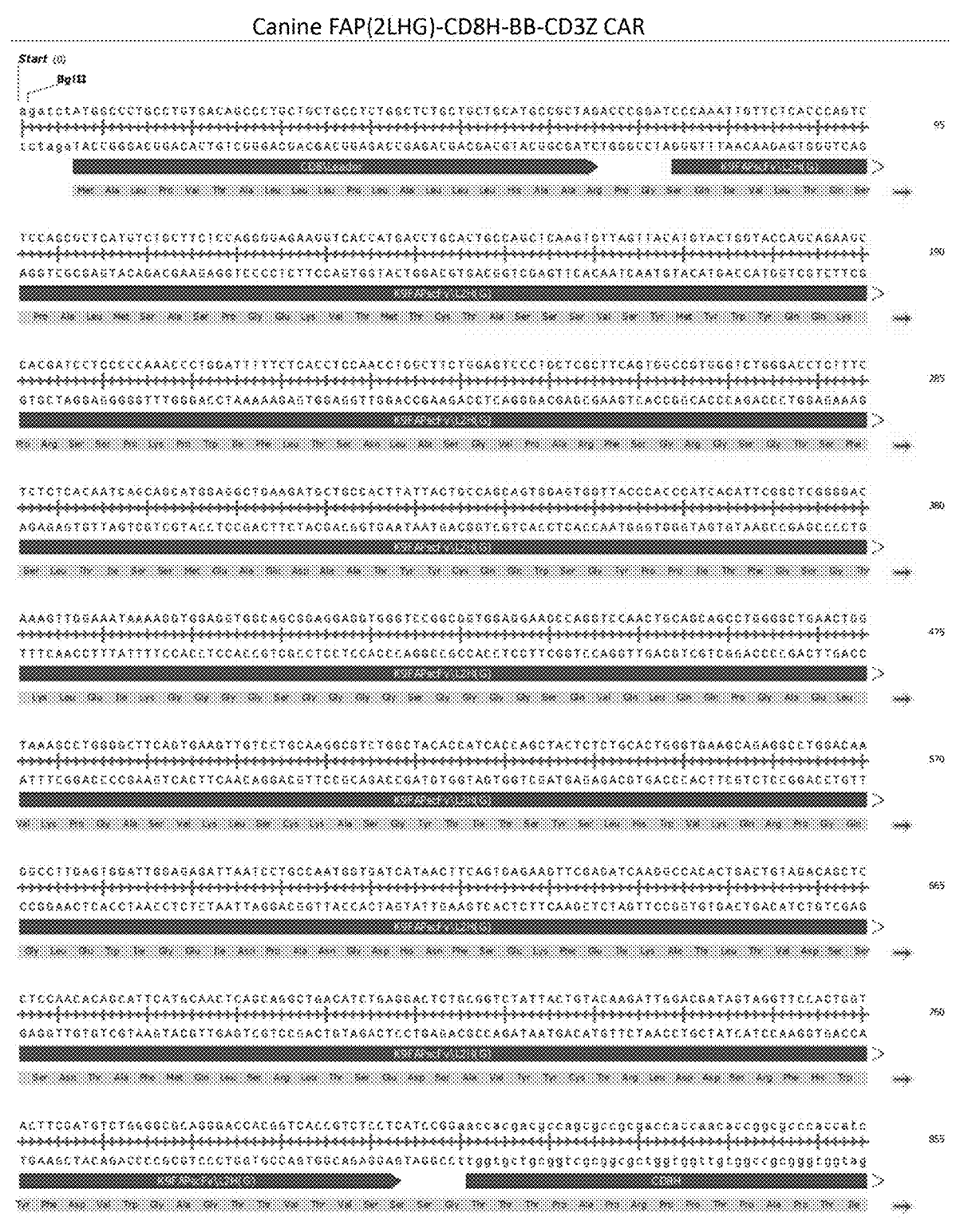
Figure 5B:
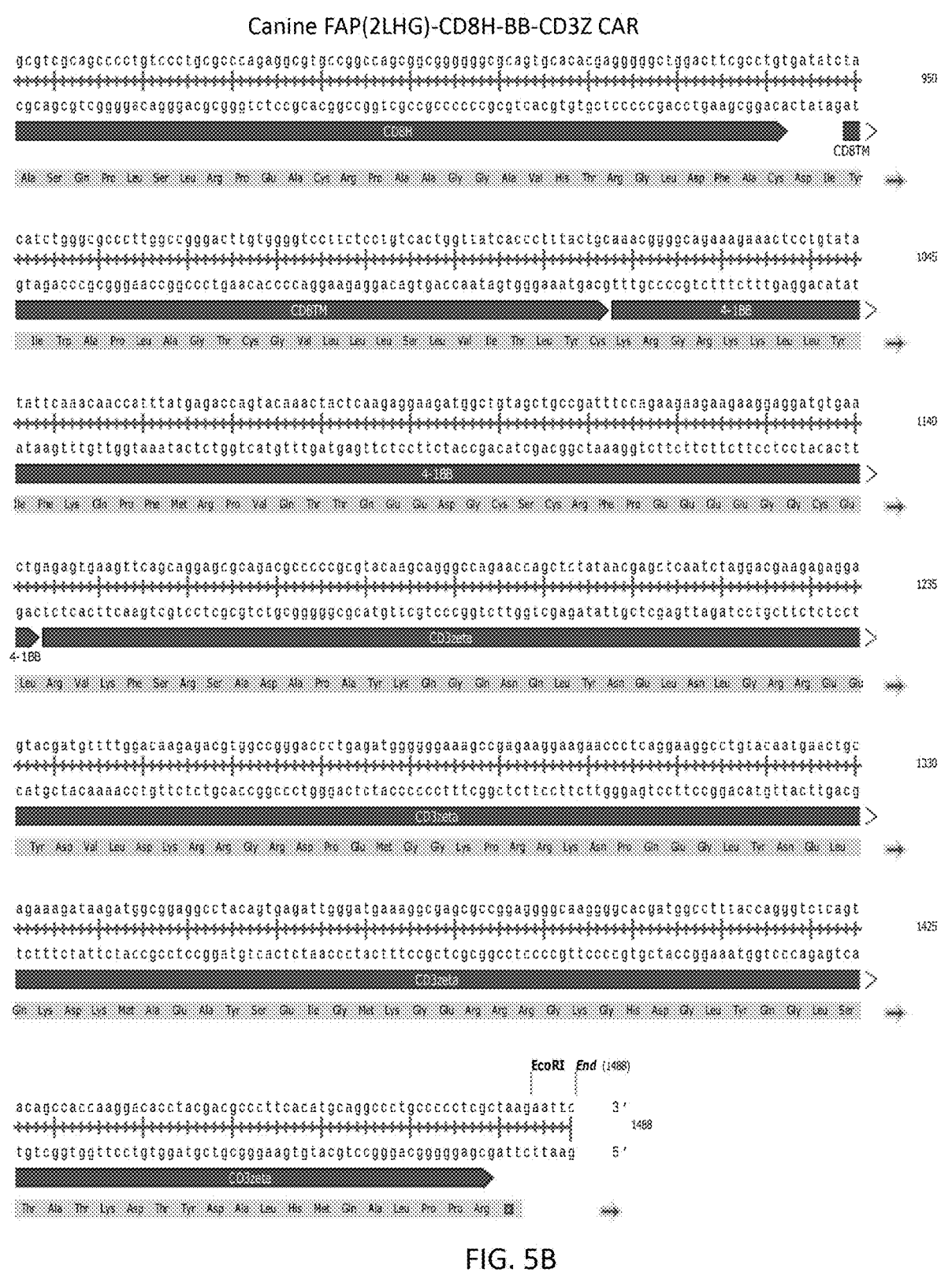

The immunoglobulin heavy and light chains were inserted into a set of plasmid cassettes that contained 2 tandem signaling domains: 4-1BB and CD3. The FAP-CD3ζ:4-1BB "double activation domain" construct was selected vs. the "triple activation domain" construct (that also includes a CD28 activation domain) for the following reasons: 1) the double construct is better at multifunctional cytokine production; 2) the double and triple constructs have similar efficacy in vitro and in vivo; 3) there have been some safety concerns with CARs containing the CD28 domain; and 4) the persistence of the triple domain mRNA is markedly reduced in T cells compared to the double domain mRNA. Constructs were made in which the heavy chain was first, followed by the light chain (HL) (FIG. 4) (SEQ ID NO: 23) and in which the light chain was first, followed by the heavy chain (LH) (FIG. 5) (SEQ ID NO: 25).

Figure 6D:
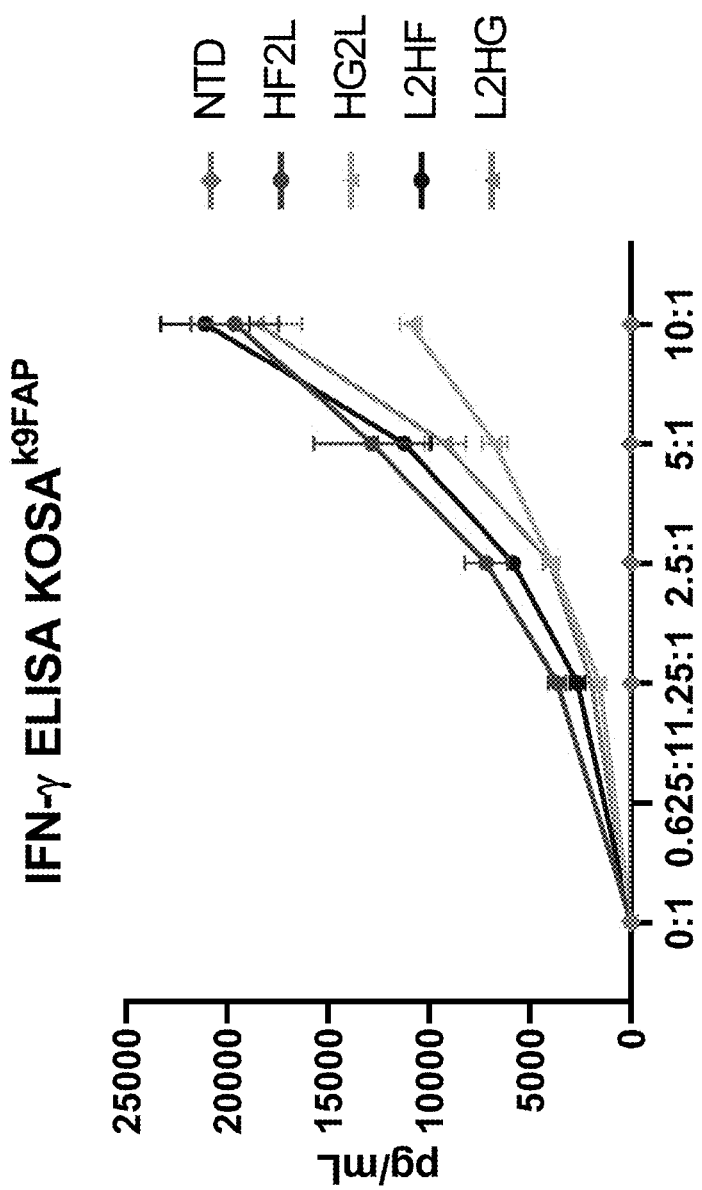

Example 5: 4G5 CAR T Cells Showed Specific IFN-γ and Cytotoxicity Against FAP-Expressing Target Cells In order to demonstrate the function of FAP-targeted CAR cells in vitro, 4G5-based CAR expressing T cells were used in in vitro co-culture assays with 3T3 cells expressing murine FAP, and canine MC-KOSA cells expressing canine FAP. To verify FAP expression, mouse 3T3 cells were stained with the murine anti-FAP antibody 73.3 (FIG. 6A). The anti-human FAP antibody F19 and an IgG isotype were used as controls. In co-culture assays, all 4G5 CAR T cells were able to recognize and kill 3T3$^{muFAP}$ target cells. Cytotoxicity and IFNγ production were used as read-outs (FIG. 6B-6C). A subsequent co-culture assay was performed using canine MC-KOSA cells as targets and IFNγ production as a measure of recognition and activation (FIG. 6D). In total, these data demonstrated the ability of 4G5-based CAR T cells to recognize target cells expressing murine and canine FAP.

Example 6: 4G5CAR T Cells Exhibit Potent Killing Activity Against High FAP Expressing Cells but Fail to Activate when Co-Cultured with Low FAP Expressing Cells FAP is often expressed at low levels by non-tumor associated tissue, including bone marrow stem cells, pancreatic islet alpha-cells, and mesenchymal stem cells. One way to focus CAR cytotoxicity on tumor-associated fibroblasts while minimizing collateral damage to unrelated tissues is to select antigen-binding domains that are unable to activate against cells expressing low levels of FAP. In order to evaluate the affinity of the 4G5CAR, human cell lines expressing various levels of huFAP on their surface were co-cultured with 4G5 CAR T cells in vitro. CAR T cell activation was then assessed by IFN-γ secretion and cytotoxic killing of the target cells. T cells expressing the CAR derived from the available well-characterized, high-affinity anti-FAP F19 antibody were used as positive control.

Figures 7A, 7B:
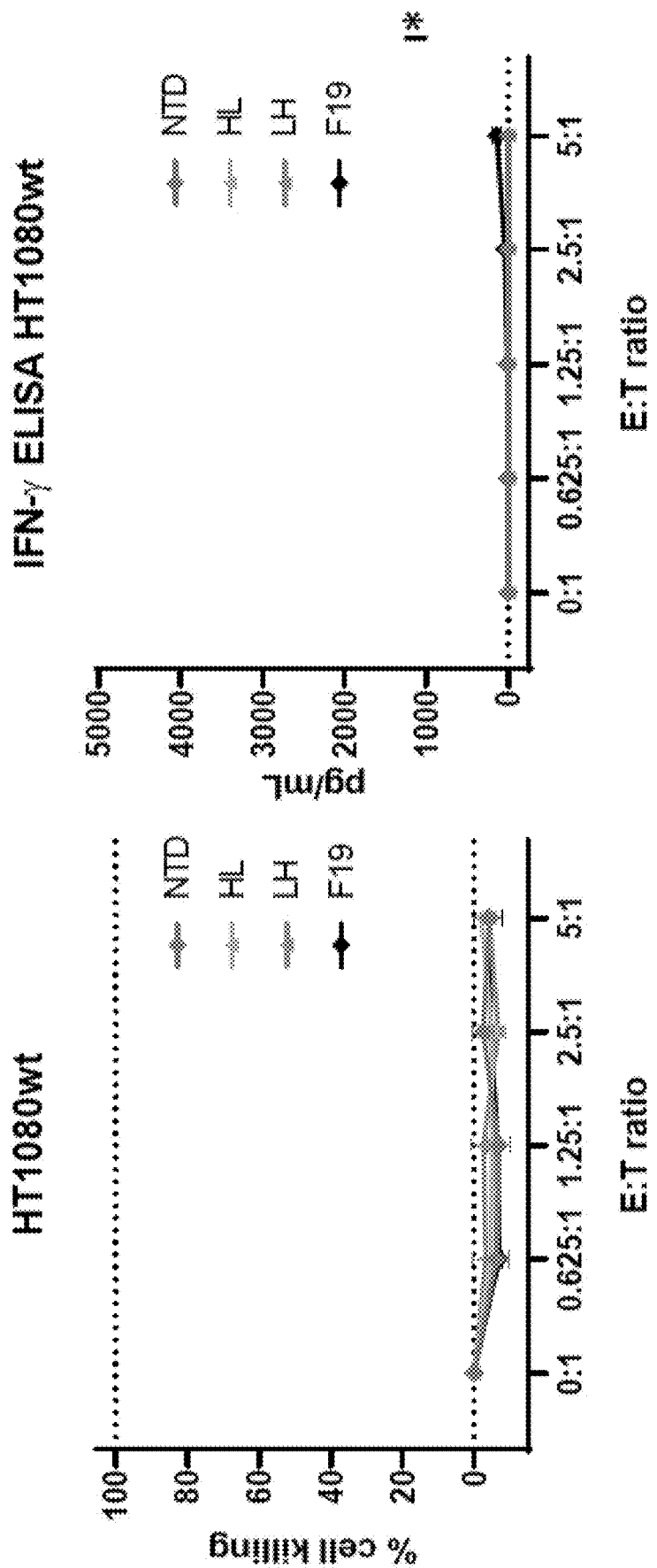
FIGS. 7A-7E are a series of graphs showing in vitro function of FAP CART cells after co-culture with FAP-negative HT1080 target cells. Assays measured cytotoxicity (FIG. 7A) of labeled target cells and IFNγ production (FIG. 7B) by ELISA analysis of supernatant after 24 hours of co-culture. HT1080 cells were then transduced to express high levels of recombinant human FAP (FIG. 7C). These cells were used as targets in subsequent in vitro co-culture assays with FAP CAR T cells. After 24 hours, target cell cytotoxicity (FIG. 7D) was assessed by luminescence and IFNγ production (FIG. 7E) by ELISA. T cell groups used in these studies included non-transduced control T cells (NTD) and high-affinity F19 FAP CAR T cells as controls. "HL" and "LH" refer to the HG2L and 2LHG versions of the 4G5-based CAR, respectively.
Figure 7C:
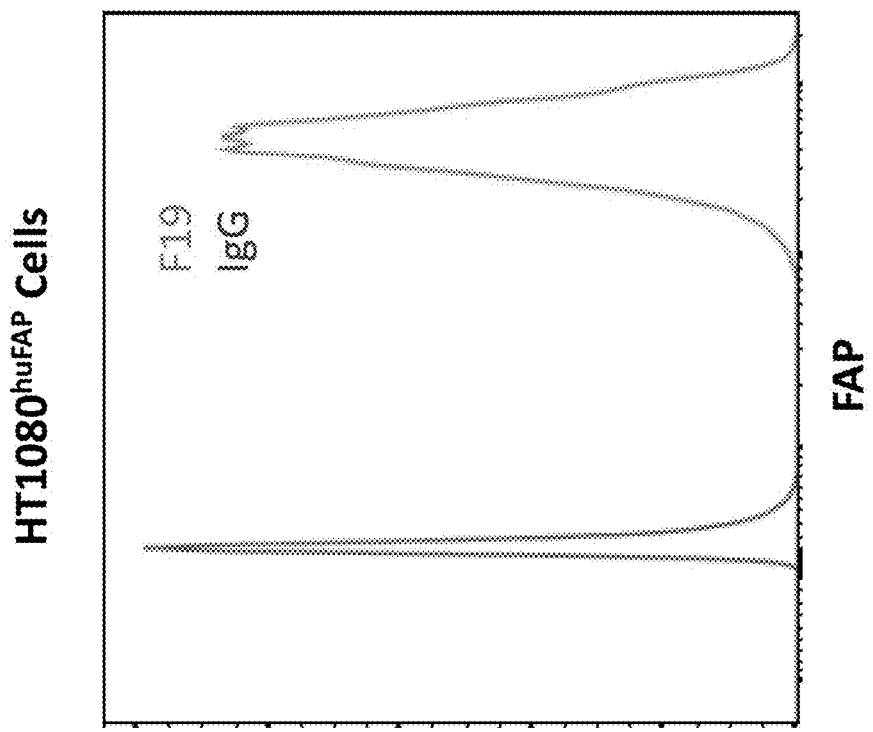
Figures 7D, 7E:
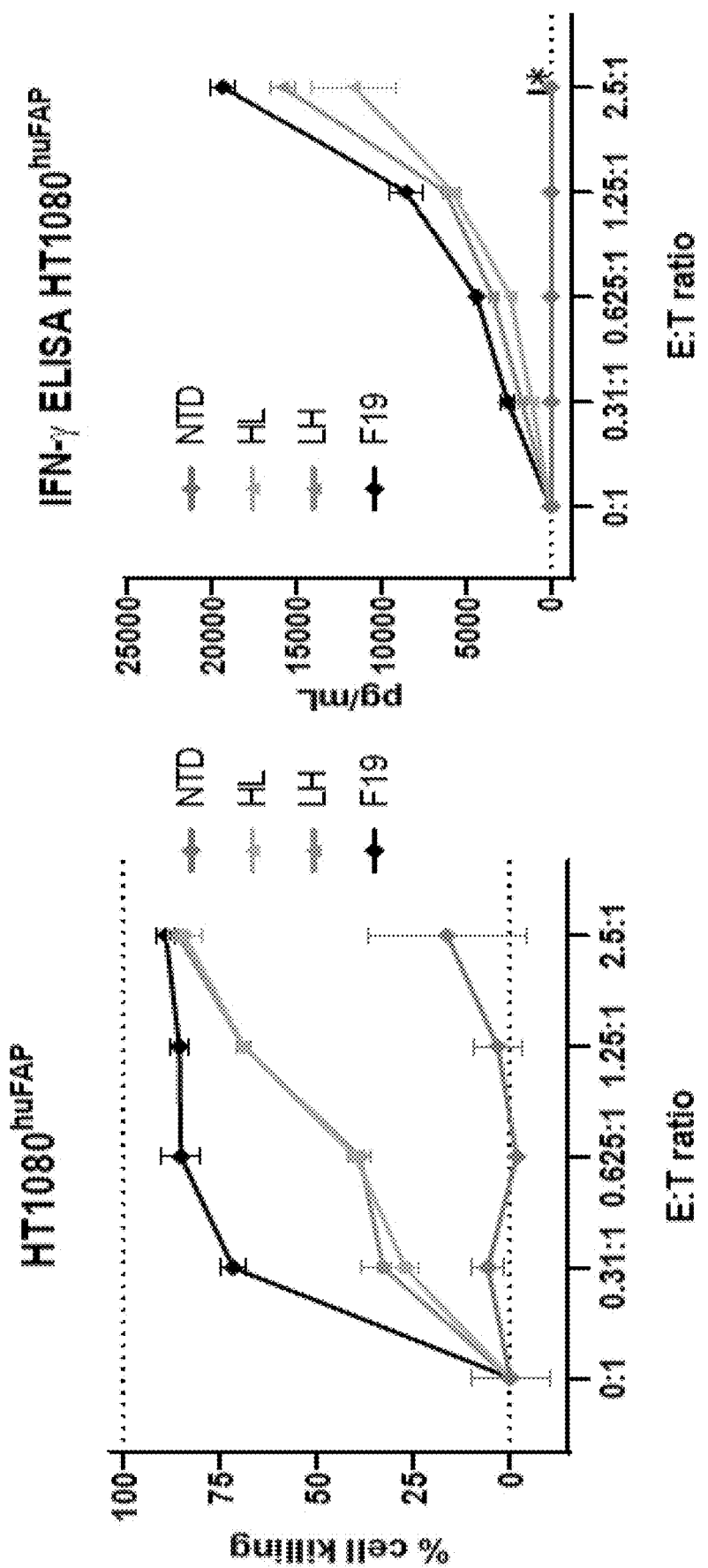
Figure 8A:
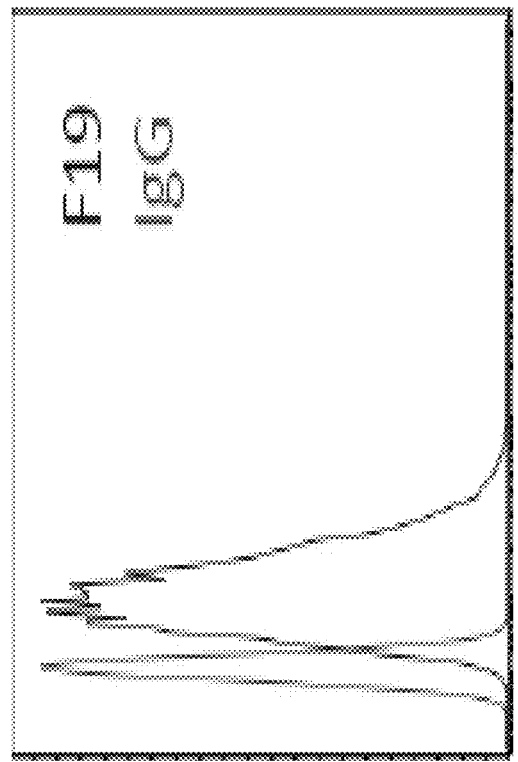
FIGS. 8A-8C are a series of graphs demonstrating the cytotoxic function of anti-FAP CAR T cells in in vitro co-culture assays with WI-38 cells. WI-38 cells are a fibroblast cell line that express an intermediate level of FAP protein, as demonstrated by flow cytometry (FIG. 8A). Subsequent cytotoxicity assays were conducted using target cell killing, as measured by luminescence (FIG. 8B) and IFNγ production as read-outs (FIG. 8C). Error bars indicate standard deviation between replicate samples in each group. *p≤0.05 for F19, HL, and LH CARs vs. NTD control cells (FIG. 8B) and F19 vs. LH and LH vs. HL cells (FIG. 8C) at 2.5:1 effector to target ratio. INS indicates no significant cytokine was measured in HL and NTD groups at all effector to target ratios.
Figures 8B, 8C:
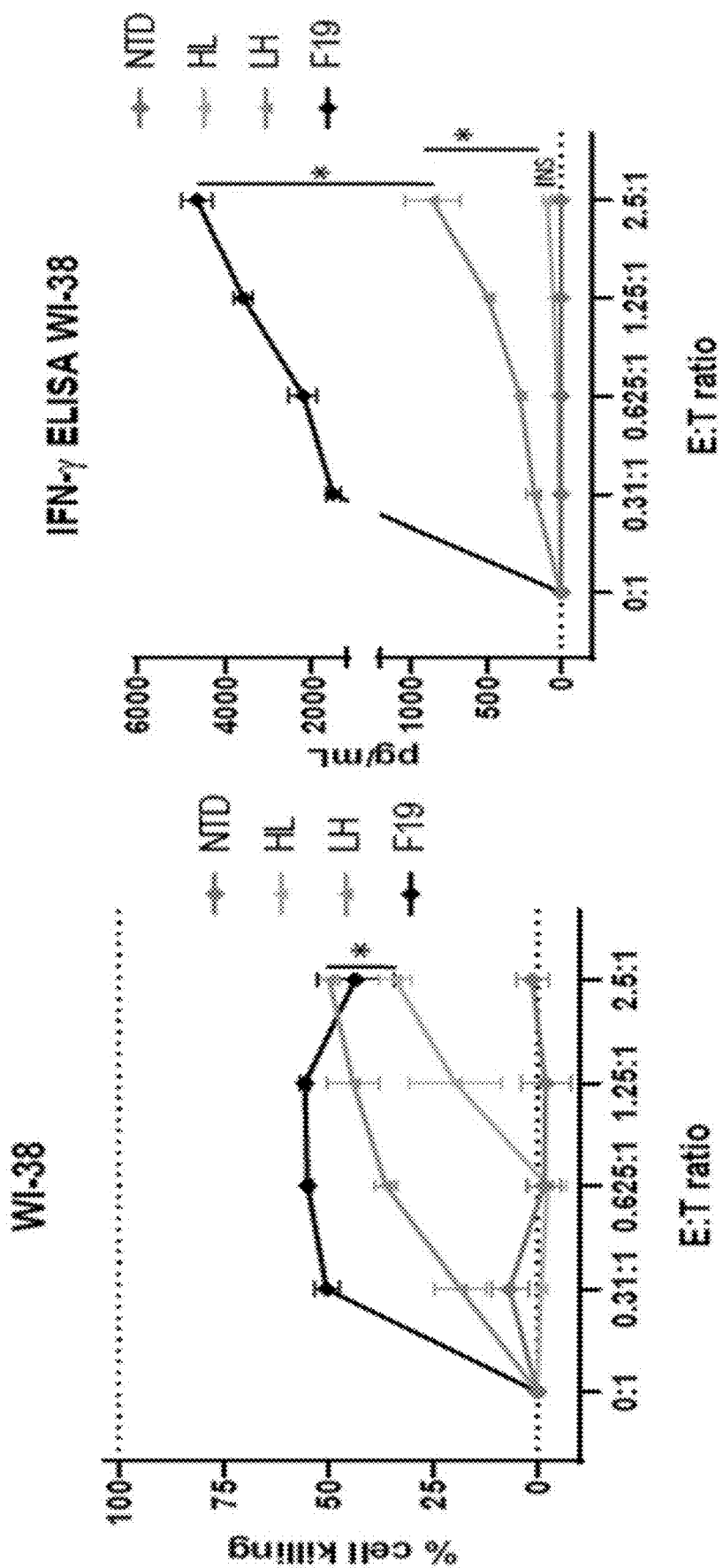
Figure 9C:
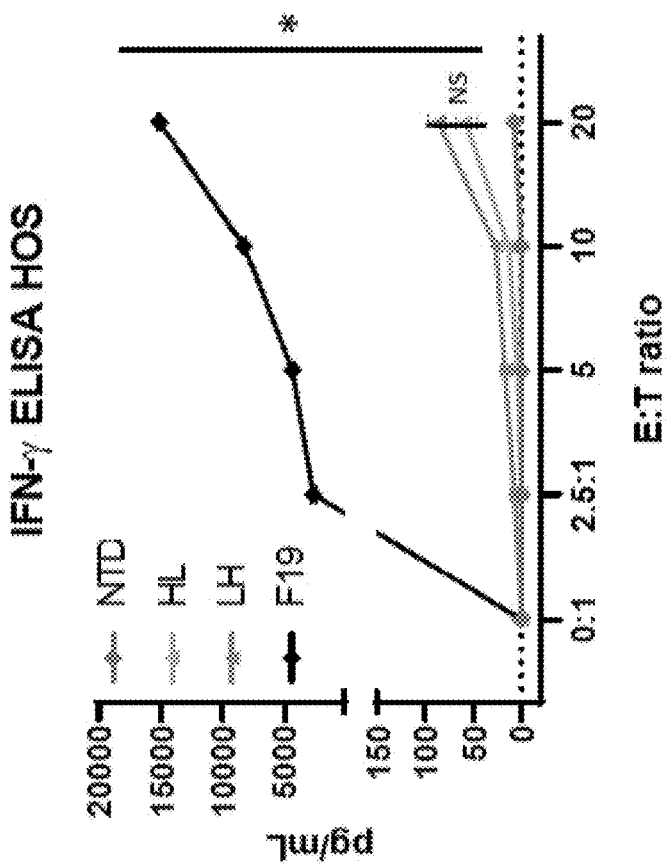
Figure 9B:
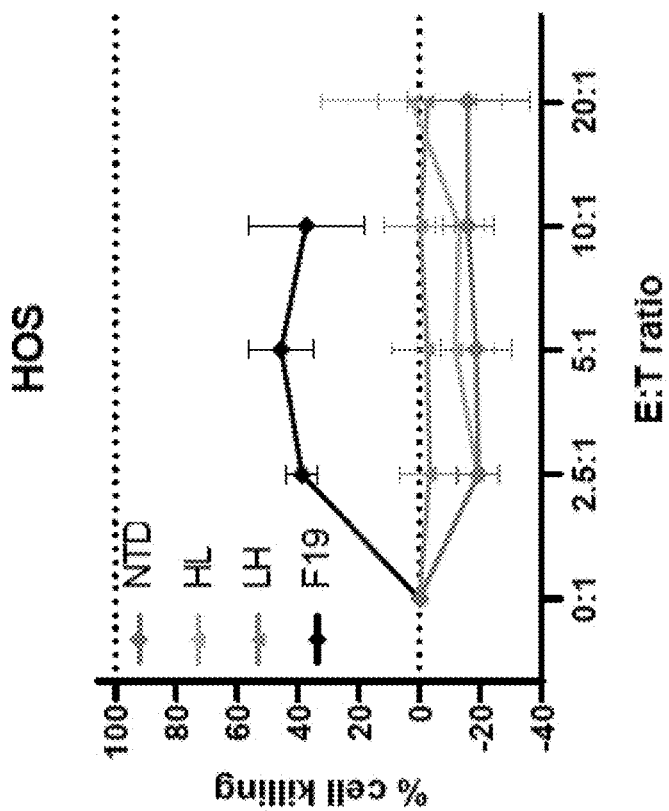

None of the CARs reacted against HT1080 cells, which do not express FAP (FIGS. 7A-7B). When HT1080 cells were transduced to express high levels of human FAP (FIG. 7C), both F19 and 4G5 CAR expressing T cells were able to recognize and kill these target cells, with F19 CAR cells exhibiting greater cytotoxicity and IFNγ production at lower effector to target ratios (FIGS. 7D-7E). In order to observe recognition of moderate levels of FAP expression, subsequent studies used the WI38 cell line (FIG. 8A). F19 CAR T cells readily recognized and killed these targets, while 4G5 CAR T cells had a significantly weaker response in terms of both IFNγ secretion and cytotoxicity (FIGS. 8B-8C). Interestingly, the LH version of the 4G5CAR was significantly better than the HL version, with the latter producing dramatically reduced levels of IFNγ and measurable cytotoxicity only at effector to target ratios over 1.25:1. Without wishing to bound by theory, these results indicated a clear functional effect of HL vs LH scFv construction. Lastly, only the F19-CAR recognized and killed cells expressing even very low levels of FAP (HOS cells, FIG. 9A). Even at effector to target ratios of up to 20:1, 4G5 CAR T cells had no measureable cytotoxic effect and produced only negligible levels of IFNγ, while F19 cells had a dramatically better response using both read-outs (FIGS. 9B-9C).

When comparing the CARs derived from both antibodies, 4G5CARs were found to be more specific; no response was observed when co-cultured with cells not expressing FAP and more importantly, 4G5CARs had minimal or non-cytotoxicity against cells expressing low levels of FAP, like HOS. Cytotoxicity exerted by both HG2L and L2HG variants of the 4G5 CARS were directly proportional to the human FAP expression levels on the target cells, which was not true for the F19 CAR T cells.

Example 7: Effect of FAP CAR T Cells in an Animal Model

Figure 10:
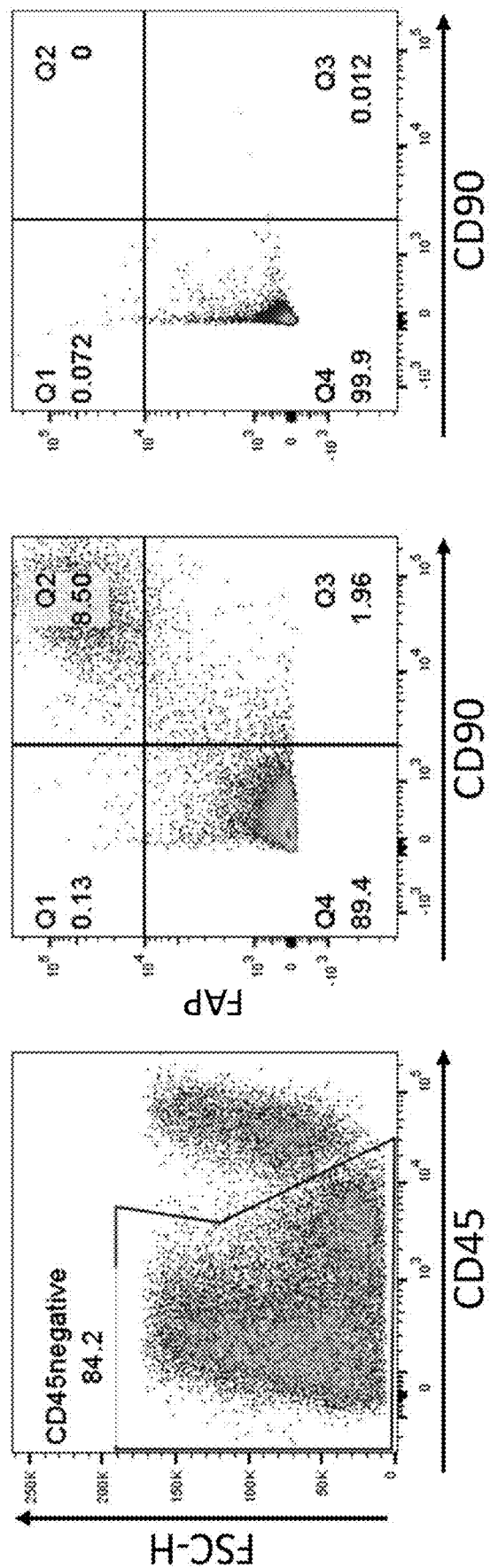
FIG. 10 is a series of graphs showing the percentage of tumor tissue cells that are CD90+FAP+ tumor-associated fibroblasts. A549 cells were implanted into NSG mice and grown for 14 days before being excised, dissociated, and stained. Cells were initially gated on CD45 negative cells (left panel). Gating on CD90+/FAP+ cells illustrates the percentage of tumor-associated fibroblast cells (center panel). Gating was determined in comparison to an isotype control (left panel).
Figure 11A:
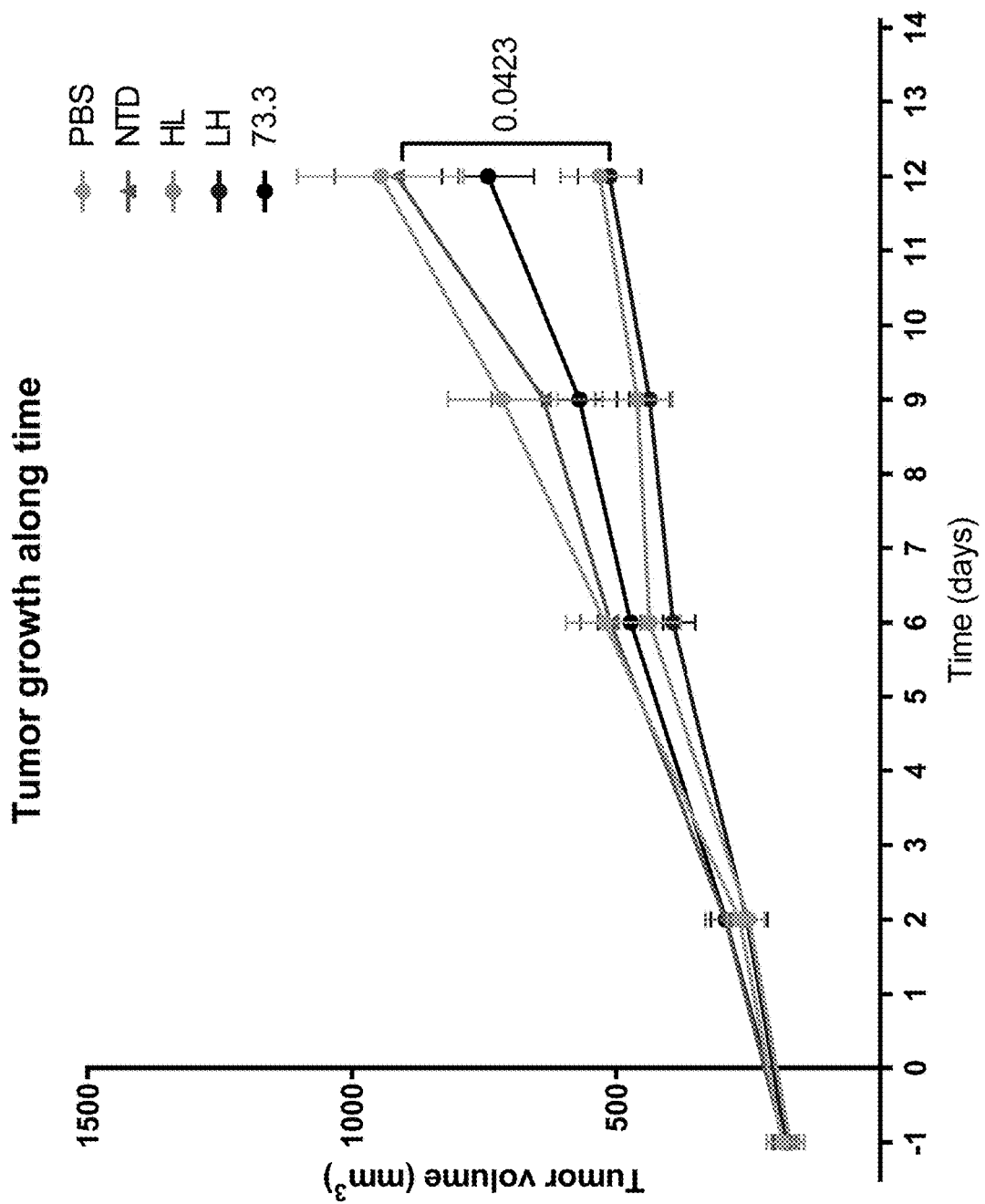
FIGS. 11A-11B are graphs showing the growth of A549 tumors established in NSG mice and treated with adoptive transfer of 20 million activated, non-transduced control T cells "NTD", 10 million CART cells expressing the 73.3 anti-FAP scFv "73.3", 10 million HGL2 4G5 CAR expressing T cells "HL", 10 million L2HG 4G5 CAR expressing T cells "LH", or a PBS vehicle control "PBS". Tumor volume was assessed at the indicated time points during the experiment (FIG. 11A). After 17 or 18 days, tumors were harvested and weighed (FIG. 11B). Error bars indicate standard deviation between animals in each experimental group. p<0.0423 for the HL and LH 4G5FAP CAR groups as compared to the non-transduced control group (FIG. 11A). *p<0.05 for HL, LH, and 73.3 expressing CAR T cells vs nontransduced (NTD) control T cells (FIG. 11B).
Figure 11B:
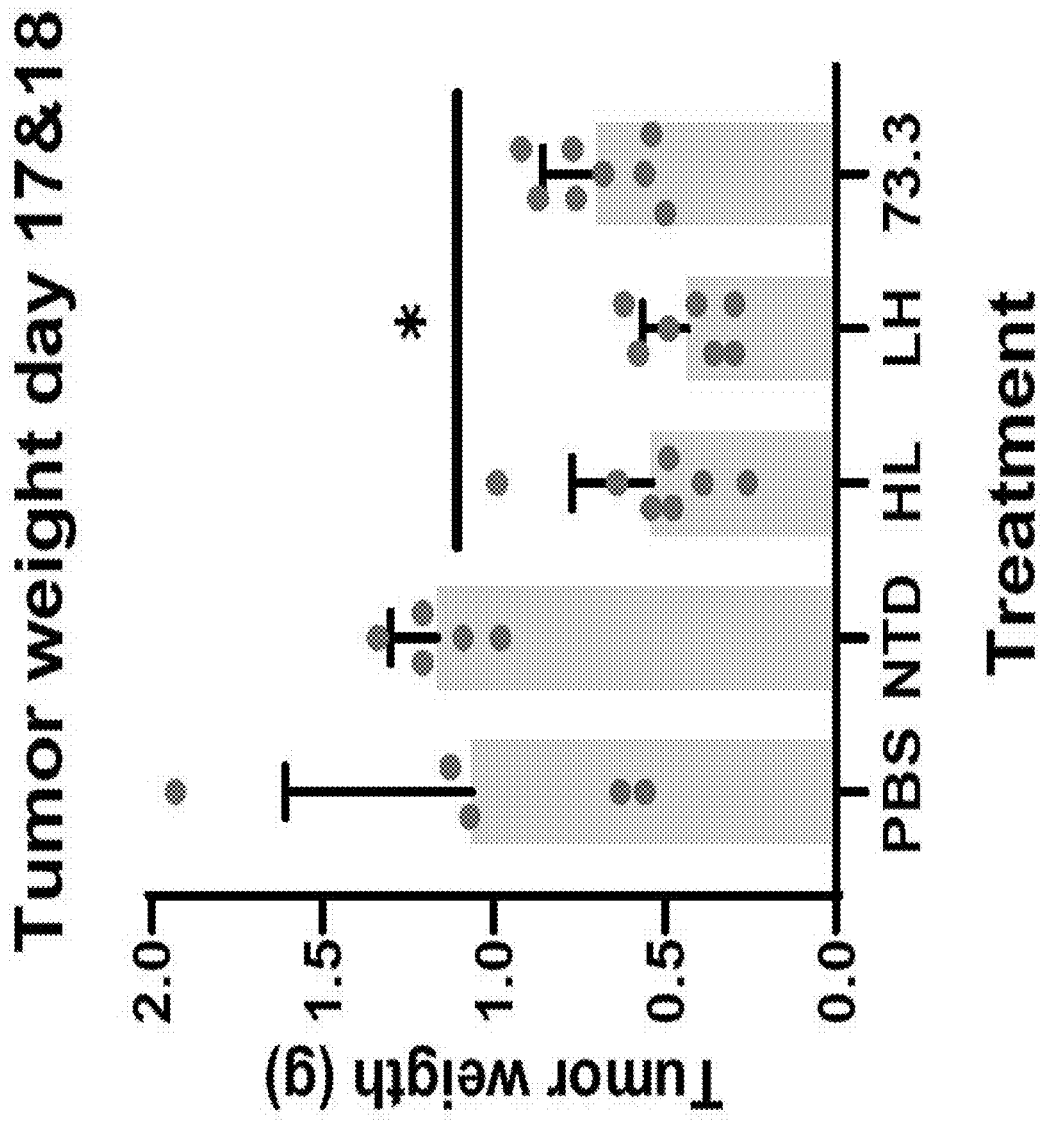

Xenograft tumors of the human adenocarcinoma line A549 were engrafted into NSG mice. Tumors were then assessed for the presence of FAP+ fibroblasts after 14 days of growth, when the tumors were ~150 mm$^3$. Flow cytometric analysis of tumor tissue found that about 8.5% of CD45-negative cells were CD90+/FAP+ fibroblasts (FIG. 10). At this time, ~20 million total T cells were injected IV. Analysis of CART cells prior to injection showed about 50% transduction. Groups included: 1) injection with PBS only, 2) injection with 20 million non-transduced activated T cells, 3) injection with 10 million 73.3 CAR T cells, 3) injection with 10 million HGL2 CARTs, and 4) injection with 10 million L2HG CARTs. Tumor growth was then followed over the next 12 days. Results showed that both the LH and HL CARs significantly reduced the size of the tumors as compared to both controls and 73.3 CAR-expressing cells (FIG. 11A). Likewise, treatment with each of the three FAP CARS (73.3, 4G5 HL, and 4G5 LH) resulted in significantly lower tumor weights after 17-18 days as compared to vehicle and non-transduced controls (FIG. 11B) Together these results demonstrate the ability of CART's targeting FAP to reduce tumor growth, and that 4G5-based CARs are superior to 73.3-based anti-FAP CAR constructs.

Example 8: The 4G5FAP-CAR has In Vitro Efficacy in NK-92 Cells

Figure 12:
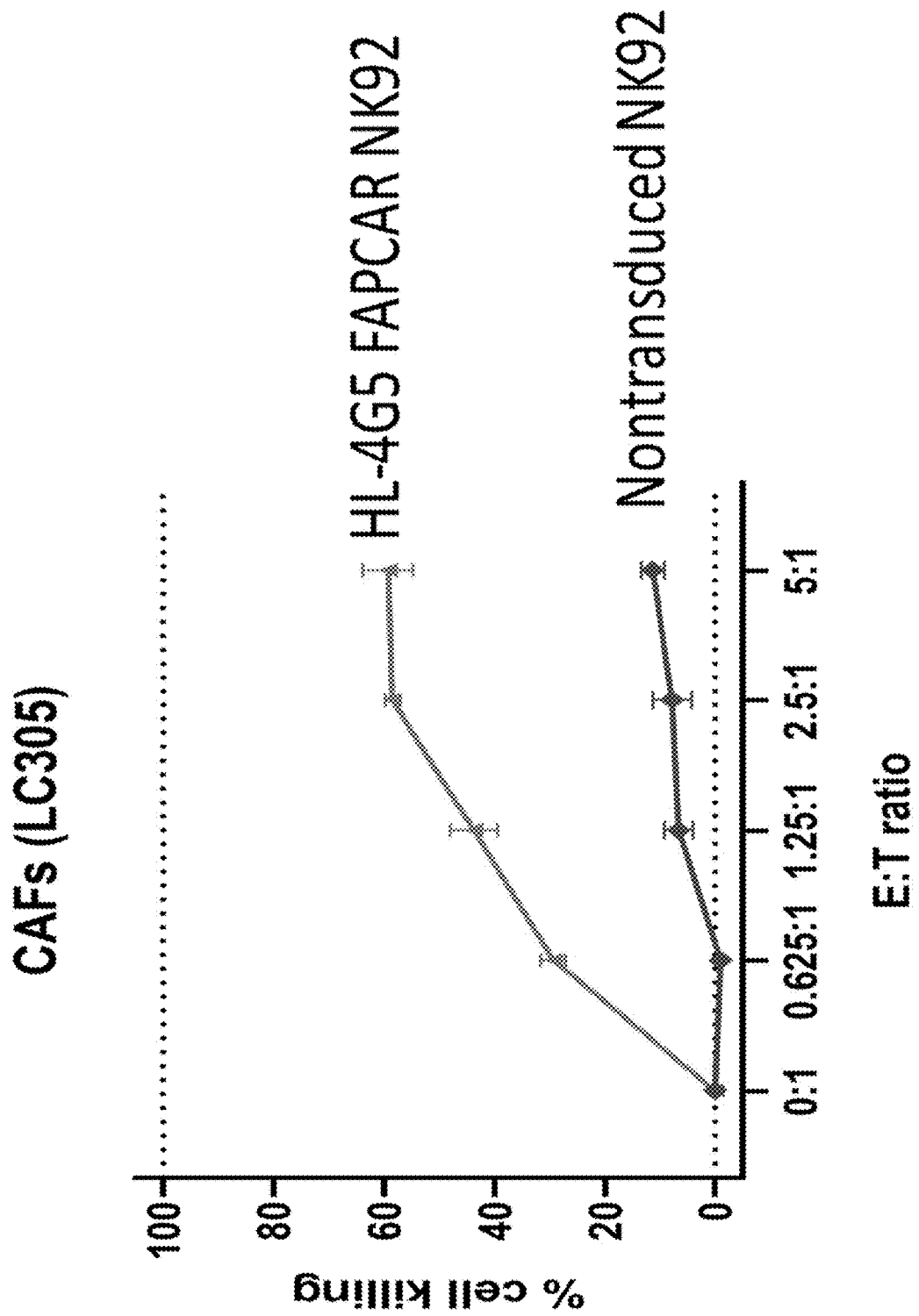
FIG. 12 is a graph showing the cytotoxic ability of HL-4G5 CAR expressing NK cells in vitro. Cells of the NK-92 NK cell line were transduced to express the 4G5FAP CAR before use in in vitro killing assays by co-culture with labeled human cancer-associated fibroblasts. Non-transduced NK92 cells were used as control cells. Engineered and control NK92 cells were incubated with target fibroblast cells at the indicated effector to target ratios. Error bars indicate standard deviation between replicate wells for each experimental group at each time point.

In addition to expression in CD4+ and CD8+ T cells, CAR expression in NK cells has also been found to result in anti-tumor cytotoxicity. In order to observe the effect of expressing the 4G5-based FAP CAR in NK cells, the construct was transduced into an NK cell line called NK-92. Following in vitro transduction and expansion, engineered NK-92 cells were then used in in vitro co-culture assays with cancer associated fibroblasts isolated from human tumors (FIG. 12). Results showed NK92-4G5FAP CAR cells demonstrated significant cytotoxic activity as compared to non-transduced NK92 cells at every effector to target ratio assayed.

Figure 13:
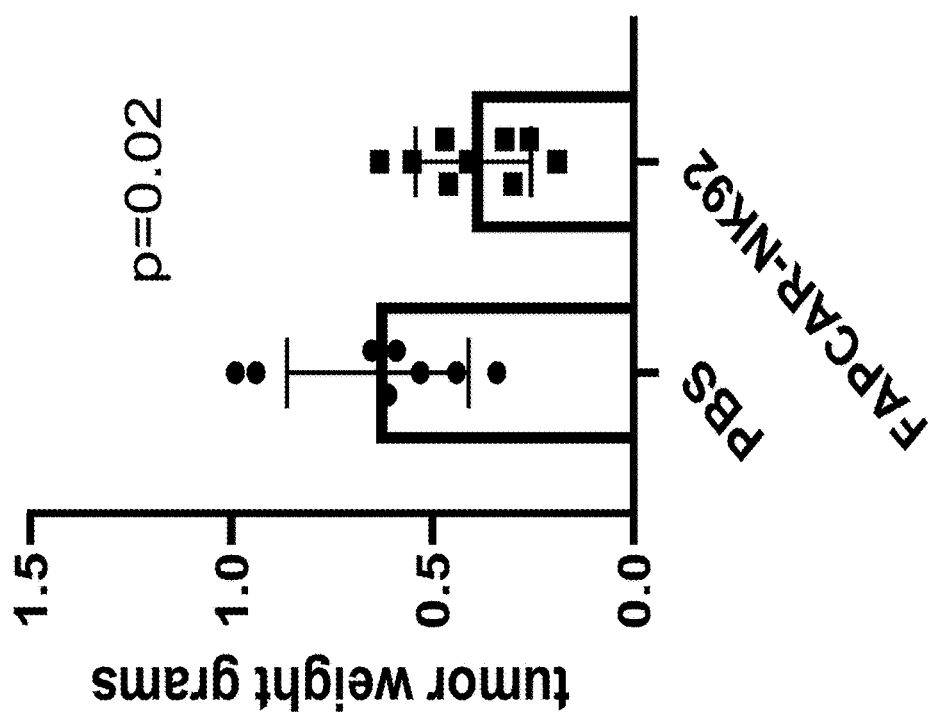
FIG. 13 is a graph showing results from an animal experiment illustrating activity of the HL-4G5 CAR expressing NK cells. Mice bearing established human SSC15 (head and neck cancer) tumors were injected with 20 million FAPCAR-NK92 cells on Day 1 and boosted with 10 million cells on days 4, 8, 11, and 14. Mice were sacrificed on day 18 and tumors weighed. Tumors from the mice injected with FAPCAR-NK92 cells were significantly smaller than untreated tumors.

Immunodeficient mice bearing established human SSC15 (head and neck cancer) tumors were injected with 20 million HL-4G5 CAR expressing NK92 cells (FAPCAR-NK92) cells on Day 1 and boosted with 10 million cells on days 4, 8, 11, and 14. Mice were sacrificed on day 18 and tumors weighed. Tumors from the mice injected with FAPCAR-NK92 cells were significantly smaller than untreated tumors (FIG. 13).These results demonstrate that cytotoxic NK cell populations would also make efficient effectors for anti-FAP CAR-based therapy.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments 5 and variations of this invention may be devised by others skilled in the art without departing from the true spirit and scope of the invention. The appended claims are intended to be construed to include all such embodiments and equivalent variations.

What is claimed is:

1. A nucleic acid comprising a polynucleotide sequence encoding a chimeric antigen receptor (CAR) capable of binding FAP, comprising an antigen-binding domain, a transmembrane domain, and an intracellular domain, wherein the antigen-binding domain comprises:
   a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and
   a light chain variable region that comprises three light chain complementarity determining regions (LCDRs), wherein LCDR1 comprises the amino acid sequence TASSSVSYMY (SEQ ID NO: 4), LCDR2 comprises the amino acid sequence LTSNLA (SEQ ID NO: 5), and LCDR3 comprises the amino acid sequence QQWSGYPPIT (SEQ ID NO: 6).

2. The nucleic acid of claim 1, wherein the CAR comprises a polypeptide selected from the group consisting of:
   (a) a heavy chain variable region encoded by a polynucleotide sequence at least 80% identical to SEQ ID NO: 8;
   (b) a light chain variable region encoded by a polynucleotide sequence at least 80% identical to SEQ ID NO: 10;
   (c) a heavy chain variable region encoded by a polynucleotide sequence at least 80% identical to SEQ ID NO: 8; and a light chain variable region encoded by a polynucleotide sequence at least 80% identical to SEQ ID NO: 10;
   (d) a single-chain variable fragment (scFv) encoded by a polynucleotide sequence at least 80% identical to SEQ ID NO: 12; and
   (e) a single-chain variable fragment (scFv) encoded by a polynucleotide sequence at least 80% identical to SEQ ID NO: 14.

3. The nucleic acid of claim 1, wherein:
   (a) the transmembrane domain comprises a transmembrane domain of CD8 alpha; and/or
   (b) the intracellular domain comprises one or more domains selected from the group consisting of:
      (i) a costimulatory signaling domain and an intracellular signaling domain;
      (ii) a costimulatory signaling domain comprising a costimulatory domain of 4-1BB;
      (iii) a costimulatory domain of DAP12;
      (iv) a costimulatory domain of CD28;
      (v) a costimulatory domain of 4-1BB and a costimulatory domain of CD28;
      (vi) a costimulatory domain of DAP12 and a costimulatory domain of CD28; and
      (vii) an intracellular domain of CD34.

4. A nucleic acid comprising a polynucleotide sequence at least 80% identical to the sequence selected from the group consisting of SEQ ID NO: 22 and 24.

5. A vector comprising the nucleic acid of claim 1.

6. The vector of claim 5, wherein the vector is an expression vector and/or the vector is selected from the group consisting of a DNA vector, an RNA vector, a plasmid, a lentiviral vector, an adenoviral vector, an adeno-associated viral vector, and a retroviral vector.

7. A modified cell comprising the nucleic acid of claim 1, wherein the modified cell is selected from the group consisting of an immune cell and a precursor cell thereof.

8. A modified cell comprising a chimeric antigen receptor (CAR) capable of binding fibroblast activation protein (FAP), wherein the modified cell is selected from the group consisting of an immune cell and a precursor cell thereof, and wherein the CAR comprises:
   a heavy chain variable region that comprises three heavy chain complementarity determining regions (HCDRs), wherein HCDR1 comprises the amino acid sequence YTITSYSLH (SEQ ID NO: 1), HCDR2 comprises the amino acid sequence EINPANGDHNFSEKFEIK (SEQ ID NO: 2), and HCDR3 comprises the amino acid sequence LDDSRFHWYFDV (SEQ ID NO: 3); and
   a light chain variable region that comprises three light chain complementarity determining regions (LCDRs), wherein LCDR1 comprises the amino acid sequence TASSSVSYMY (SEQ ID NO: 4), a LCDR2 comprises the amino acid sequence LTSNLA (SEQ ID NO: 5), and LCDR3 comprises the amino acid sequence QQWSGYPPIT (SEQ ID NO: 6).

9. The modified cell of claim 8, wherein the CAR is selected from the group consisting of:
   (a) a CAR comprising a heavy chain variable region comprising an amino acid sequence at least 80% identical to SEQ ID NO: 7; and a light chain variable region comprising an amino acid sequence at least 80% identical to SEQ ID NO: 9;
   (b) a CAR comprising a single-chain variable fragment (scFv) comprising an amino acid sequence at least 80% identical to SEQ ID NO: 11;
   (c) a CAR comprising a single-chain variable fragment (scFv) comprising an amino acid sequence at least 80% identical to SEQ ID NO: 13;
   (d) a CAR comprising an amino acid sequence at least 80%, identical to SEQ ID NO: 23; and
   (e) a CAR comprising an amino acid sequence at least 80% identical to SEQ ID NO: 25.

10. The modified cell of claim 8, wherein the CAR is capable of binding human FAP.

11. The modified cell of claim 8, wherein the modified cell is selected from the group consisting of:
   (a) a modified T cell;
   (b) a modified NK cell;
   (c) an autologous cell;
   (d) an autologous cell obtained from a human subject;
   (e) an autologous cell obtained from a canine subject; and
   (f) an allogeneic cell.

12. A pharmaceutical composition comprising a therapeutically effective amount of the modified cell of claim 8, and a pharmaceutically acceptable excipient.

* * * * *

UNITED STATES PATENT AND TRADEMARK OFFICE
CERTIFICATE OF CORRECTION

PATENT NO. : 12,116,418 B2
APPLICATION NO. : 17/029702
DATED : October 15, 2024
INVENTOR(S) : Steven A. Albelda, Ellen Puré and Leslie Todd It is certified that error appears in the above-identified patent and that said Letters Patent is hereby corrected as shown below:

In the Claims

Column 129, Lines 39-54, Claim 3 should read:
3. The nucleic acid of claim 1, wherein:
(a) the transmembrane domain comprises a transmembrane domain of CD8 alpha; and/or
(b) the intracellular domain comprises one or more domains selected from the group consisting of:
(i) a costimulatory signaling domain and an intracellular signaling domain;
(ii) a costimulatory signaling domain comprising a costimulatory domain of 4-1BB;
(iii) a costimulatory domain of DAP12;
(iv) a costimulatory domain of CD28;
(v) a costimulatory domain of 4-1BB and a costimulatory domain of CD28;
(vi) a costimulatory domain of DAP12 and a costimulatory domain of CD28; and
(vii) an intracellular domain of CD3ζ.

Signed and Sealed this
First Day of April, 2025

Coke Morgan Stewart
*Acting Director of the United States Patent and Trademark Office*